United States Patent
Caberoy

(10) Patent No.: US 11,034,739 B2
(45) Date of Patent: Jun. 15, 2021

(54) LIGAND-GUIDED PHAGOCYTOSIS BASED THERAPY FOR TREATMENT OF ALZHEIMER'S DISEASE AND OTHER NEURODEGENERATIVE DISEASES

(71) Applicant: The Board Of Regents Of The Nevada System Of Higher Education On Behalf Of The University of Nevada, Las Vegas, NV (US)

(72) Inventor: Nora Blanca Caberoy, Henderson, NV (US)

(73) Assignee: The Board Of Regents Of The Nevada System Of Higher Education On Behalf Of The University of Nevada, Las Vegas, NV (US)

(*) Notice: Subject to any disclaimer, the term of this patent is extended or adjusted under 35 U.S.C. 154(b) by 0 days.

(21) Appl. No.: 15/774,935

(22) PCT Filed: Nov. 11, 2016

(86) PCT No.: PCT/US2016/061605
§ 371 (c)(1),
(2) Date: May 9, 2018

(87) PCT Pub. No.: WO2017/083700
PCT Pub. Date: May 18, 2017

(65) Prior Publication Data
US 2018/0327465 A1 Nov. 15, 2018

Related U.S. Application Data

(60) Provisional application No. 62/254,846, filed on Nov. 13, 2015.

(51) Int. Cl.
| | | |
|---|---|---|
| *C07K 14/47* | (2006.01) |
| *A61K 38/00* | (2006.01) |
| *A61P 25/28* | (2006.01) |
| *C07K 14/745* | (2006.01) |
| *C07K 16/24* | (2006.01) |
| *C07K 16/28* | (2006.01) |

(52) U.S. Cl.
CPC .......... *C07K 14/4702* (2013.01); *A61K 38/00* (2013.01); *A61P 25/28* (2018.01); *C07K 14/4711* (2013.01); *C07K 14/745* (2013.01); *C07K 16/248* (2013.01); *C07K 16/2896* (2013.01); *C07K 2319/70* (2013.01); *C07K 2319/75* (2013.01)

(58) Field of Classification Search
CPC combination set(s) only.
See application file for complete search history.

(56) References Cited

U.S. PATENT DOCUMENTS

| | | | |
|---|---|---|---|
| 5,391,377 A | 2/1995 | Barnwell | |
| 5,579,250 A | 11/1996 | Balaji et al. | |
| 5,612,895 A | 3/1997 | Balaji et al. | |
| 5,631,280 A | 5/1997 | Ciccarone et al. | |
| 6,787,523 B1 * | 9/2004 | Schenk | A61K 38/1709 424/1.57 |
| 2002/0082385 A1 | 6/2002 | Terrett et al. | |
| 2011/0300141 A1 | 12/2011 | Chakravarthy | |

FOREIGN PATENT DOCUMENTS

| | | |
|---|---|---|
| EP | 0045665 A1 | 2/1982 |
| WO | WO-2007/145589 A8 | 12/2007 |
| WO | WO-2005/075507 A1 | 8/2015 |
| WO | WO-2016/137947 A1 | 9/2016 |

OTHER PUBLICATIONS

Caberoy et al., The EMBO Journal (2010) 29, 3898-3910, published online Oct. 2010.*
Xie et al., J Neurosci., 22: RC221, (Year: 2002).*
Aldinger, K.A. et al., Genetic variation and population substructure in outbred CD-1 mice: implications for genome-wide association studies. PLoS One. 2009; 4(3):e4729 (10 pages).
Almquist et al., Synthesis and Biological Activity of a Ketomethylene Analogue of a Tripeptide Inhibitor of Angiotensin Converting Enzyme. J Med Chem. 1980; 23(12):1392-8.
Alzheimer's Association, 2011 Alzheimer's disease facts and figures. Alzheimers Dement. 2011; 7(2):208-44.
Barile, G.R. and Schmidt, A.M., RAGE and its ligands in retinal disease. Curr Mol Med. 2007; 7(8):758-65.
Bolton, M.M. et al., Postnatal alterations in GABAB receptor tone produce sensorimotor gating deficits and protein level differences in adulthood. Int J Devl Neurosci. 2015; 41:17-27.
Borchelt, D.R. et al., Familial Alzheimer's disease-linked presenilin 1 variants elevate Aβ1-42/1-40 ratio in vitro and in vivo. Neuron. 1996; 17(5):1005-13.
Caberoy, N.B. et al., Can phage display be used as a tool to functionally identify endogenous eat-me signals in phagocytosis? J Biomol Screen. 2009; 14(6):653-61.
Caberoy, N.B. et al., Efficient identification of phosphatidylserine-binding proteins by ORF phage display. Biochem Biophys Res Commun. 2009; 386(1):197-201.
Caberoy, N.B. et al., Efficient identification of tubby-binding proteins by an improved system of T7 phage display. J Mol Recognit. 2010; 23(1):74-83.

(Continued)

*Primary Examiner* — Kimberly Ballard
*Assistant Examiner* — Stacey N Macfarlane
(74) *Attorney, Agent, or Firm* — Ballard Spahr LLP

(57) ABSTRACT

Disclosed are conjugates and compositions comprising an amyloid beta binding protein conjugated to a MerTK ligand. Disclosed are methods of clearing amyloid beta aggregates from a subject comprising administering a therapeutically effective amount of the conjugates and compositions comprising an amyloid beta binding protein conjugated to a MerTK ligand. Disclosed are methods of treating Alzheimer's Disease comprising administering to a subject in need thereof a therapeutically effective amount of conjugates and compositions comprising an amyloid beta binding protein conjugated to a MerTK ligand.

15 Claims, 17 Drawing Sheets

Specification includes a Sequence Listing.

(56) References Cited

OTHER PUBLICATIONS

Caberoy, N.B. et al., Galectin-3 is a new MerTK-specific eat-me signal. J Cell Physiol. 2012; 227(2):401-7.
Caberoy, N.B. et al., Identification of tubby and tubby-like protein 1 as eat-me signals by phage display. Exp Cell Res. 2010; 316(2):245-57.
Caberoy, N.B. et al., Tubby and tubby-like protein 1 are new MerTK ligands for phagocytosis. EMBO J. 2010; 29(23):3898-910.
Caberoy, N.B. et al., Tubby regulates microglial phagocytosis through MerTK. J Neuroimmunol. 2012; 252(1-2):40-8.
Caberoy, N.B., Synergistic interaction of tubby and tubby-like protein 1 (tulp1). Adv Exp Med Biol. 2014; 801:503-9.
Chen, J. et al., Recombinant adenovirus coexpressing covalent peptide/MHC class II complex and B7-1: in vitro and in vivo activation of myelin basic protein-specific T cells. J Immunol. 2001; 167(3):1297-305.
Chia, R. et al., The origins and uses of mouse outbred stocks. Nat Genet. 2005; 37(11):1181-6.
Cramer, P.E. et al., ApoE-directed therapeutics rapidly clear β-amyloid and reverse deficits in AD mouse models. Science. 2012; 335(6075):1503-6.
Cui, S. et al., Genetic variation within and between strains of outbred Swiss mice. Lab Anim. 1993; 27(2):116-23.
Doens, D. and Fernández, P.L., Microglia receptors and their implications in the response to amyloid β for Alzheimer's disease pathogenesis. J Neuroinflammation. 2014; 11:48 (14 pages).
Eckman, C.B. et al., A new pathogenic mutation in the APP gene (I716V) increases the relative proportion of Aβ42(43). Hum Mol Genet. 1997; 6(12):2087-9.
Evans, C.G. et al., Heat shock proteins 70 and 90 inhibit early stages of amyloid β-(1-42) aggregation in Vitro. J Biol Chem. 2006; 281(44):33182-91.
Fang, X. et al., The Synergistic Beneficial Effects of Ginkgo Flavonoid and Coriolus versicolor Polysaccharide for Memory Improvements in a Mouse Model of Dementia. Evid Based Complement Alternat Med. 2015; 2015:128394 (9 pages).
Garcia-Alloza, M. et al., Characterization of amyloid deposition in the APPswe/PS1dE9 mouse model of Alzheimer disease. Neurobiol Dis. 2006; 24(3):516-24.
Giustarini, D. et al., Nitrite and nitrate measurement by Griess reagent in human plasma: evaluation of interferences and standardization. Methods Enzymol. 2008; 440:361-80.
Glenn, J.V. and Stitt, A.W., The role of advanced glycation end products in retinal ageing and disease. Biochim Biophys Acta. 2009; 1790(10):1109-16.
Goure, W.F. et al., Targeting the proper amyloid-beta neuronal toxins: a path forward for Alzheimer's disease immunotherapeutics. Alzheimers Res Ther. 2014; 6(4):42.
Graeber, M.B. et al., The third glial cell type, the microglia: cellular markers of activation in situ. Acta Histochem Suppl. 1990; 38:157-60.
Guo, H.B. et al., Donepezil improves learning and memory deficits in APP/PS1 mice by inhibition of microglial activation. Neuroscience. 2015; 290:530-42.
Hann, M.M., On the Double Bond Isotere of the Peptide Bond: Preparation of an Enkephalin Analogue. J ChemSoc Perkin Trans 1. 1982; 307-14.
Henson, P.M. and Hume, D.A., Apoptotic cell removal in development and tissue homeostasis. Trends Immunol. 2006; 27(5):244-50.
Herbert, P. et al., A Large-Scale Process to Produce Microencapsulated Proteins. Pharm Res. 1998; 15(2):357-61.
Hochreiter-Hufford, A. and Ravichandran, K.S., Clearing the dead: apoptotic cell sensing, recognition, engulfment, and digestion. Cold Spring Harb Perspect Biol. 2013; 5(1):a008748 (19 pages).
Holladay, M.W. and D.H. Rich, Synthesis of Hydroxyethylene and Ketomethylene Dipeptide Isoteres. Tetrahedron Lett. 1983; 24(41):4401-4.
Hollyfield, J.G. et al., Oxidative damage-induced inflammation initiates age-related macular degeneration. Nat Med. 2008; 14(2):194-8.
Hong-Qi, Y. et al., Current advances in the treatment of Alzheimer's disease: focused on considerations targeting Aβ and tau. Transl Neurodegener. 2012; 1:21 (12 pages).
Hruby, V.J., Conformational Restrictions of Biologically Active Peptides via Amino Acid Side Chain Groups. Life Sci. 1982; 31(3):189-99.
Hudson, D. et al., Methionine Enkephalin and Isoteric Analogues I. Synthesis on a Phenolic Resin Support. Int J Pept Prot Res. 1979; 14(3):177-85.
Iida, Y. et al., β2 microglobulin modified with advanced glycation end products induces interleukin-6 from human macrophages: role in the pathogenesis of hemodialysis-associated amyloidosis. Biochem Biophys Res Commun. 1994; 201(3):1235-41.
Iwatsubo, T. et al., Full-length amyloid-β(1-42(43)) and amino-terminally modified and truncated amyloid-β42(43) deposit in diffuse plaques. Am J Pathol. 1996; 149(6):1823-30.
Jankowsky, J.L. et al., Mutant presenilins specifically elevate the levels of the 42 residue β-amyloid peptide in vivo: evidence for augmentation of a 42-specific γ secretase. Hum Mol Genet. 2004; 13(2):159-70.
Jankowsky, J.L. et al., APP processing and amyloid deposition in mice haplo-insufficient for presenilin 1. Neurobiol Aging. 2004; 25(7):885-92.
Jarrett, J.T. et al., The carboxy terminus of the β amyloid protein is critical for the seeding of amyloid formation: implications for the pathogenesis of Alzheimer's disease. Biochemistry. 1993; 32(18):4693-7.
Jennings-White, C. and R.G. Almquist, Synthesis of Ketomethylene Analogs of Dipeptides. Tetra Lett. 1982; 23(25):2533-4.
Jensen, C.J. et al., Immune players in the CNS: the astrocyte. J Neuroimmune Pharmacol. 2013; 8(4):824-39.
Johnson, O.L. et al., A Month-Long Effect from a Single Injection of Microencapsulated Human Growth Hormone. Nature Med. 1996; 2(7):795-9.
Kingham, P.J. et al., Apoptotic pathways mobilized in microglia and neurones as a consequence of chromogranin A-induced microglial activation. J Neurochem. 1999; 73(2):538-47.
Kinney, J.W. et al., Impairment of memory consolidation by galanin correlates with in-Vivo inhibition of both LTP and CREB phosphorylation. Neurobiol Learn Mem. 2009; 92(3):429-38.
Kleiger, G. et al., Rapid E2-E3 assembly and disassembly enable processive ubiquitylation of cullin-RING ubiquitin ligase substrates. Cell. 2009; 139(5):957-68.
Kooi, E.-J. et al., Abundant extracellular myelin in the meninges of patients with multiple sclerosis. Neuropathol Appl Neurobiol. 2009; 35(3):283-95.
Kumar, A. et al., A review on Alzheimer's disease pathophysiology and its management: an update. Pharmacol Rep. 2015; 67(2):195-203.
Landers, M.R. et al., Forced exercise before or after induction of 6-OHDA-mediated nigrostriatal insult does not mitigate behavioral asymmetry in a hemiparkinsonian rat model. Brain Res. 2014; 1543:263-70.
LeBlanc, M.E. et al., Hepatoma-derived growth factor-related protein-3 is a novel angiogenic factor. PLoS One; 2015. 10(5):e0127904 (16 pages).
Lee, C.Y.D. and Landreth, G.E., The role of microglia in amyloid clearance from the AD brain. J Neural Transm. 2010; 117(8):949-60.
Lemke, G. and Rothlin, C.V., Immunobiology of the TAM receptors. Nat Rev Immunol. 2008; 8(5):327-36.
Li, W., Synergistic antibody induction by antigen-CD40 ligand fusion protein as improved immunogen. Immunology. 2005; 115(2):215-22.
Lipovsek, D. and Pluckthun, A., In-vitro protein evolution by ribosome display and mRNA display. J Immunol Methods. 2004; 290(1-2):51-67.

(56) References Cited

OTHER PUBLICATIONS

Lyck, L. et al., An empirical analysis of the precision of estimating the numbers of neurons and glia in human neocortex using a fractionator-design with sub-sampling. J Neurosci Methods. 2009; 182(2):143-56.
Mangialasche, F. et al., Alzheimer's disease: clinical trials and drug development. Lancet Neurol. 2010; 9(7):702-16.
Mayeux, R. et al., Plasma amyloid beta peptide 1-42 and incipient Alzheimer's disease. Ann Neurol. 1999; 46(3):412-6.
McKinnon, S.J., Glaucoma: ocular Alzheimer's disease? Front Biosci. 2003; 8:s1140-56.
Moreira, P.I. et al., An integrative view of the role of oxidative stress, mitochondria and insulin in Alzheimer's disease. J Alzheimers Dis. 2009; 16(4):741-61.
Morley, J.S., Modulation of the Action of Regulatory Peptides by Structural Modification. Trends Pharm Sci. 1(2):463-8 (1980) (general review).
Murtishaw, A.S. et al., Effect of acute lipopolysaccharide-induced inflammation in intracerebroventricular streptozotocin injected rats. Neuropharmacology. 2015; 101:110-22.
Neumann, A. et al., High molecular weight hyaluronic acid inhibits advanced glycation endproduct-induced NF-κβ activation and cytokine expression. FEBS Lett, 1999; 453(3):283-7.
Palop, J.J. and Mucke, L., Amyloid-beta-induced neuronal dysfunction in Alzheimer's disease: from synapses toward neural networks. Nat Neurosci. 2010; 13(7):812-8.
Pan, X.-D. et al., Microglial phagocytosis induced by fibrillar β-amyloid is attenuated by oligomeric β-amyloid: implications for Alzheimer's disease. Mol Neurodegener. 2011; 6:45 (17 pages).
Papadopoulos, J.S. and Agarwala, R., COBALT: constraint-based alignment tool for multiple protein sequences. Bioinformatics. 2007; 23(9):1073-9.
Park, D. et al., Continued clearance of apoptotic cells critically depends on the phagocyte Ucp2 protein. Nature. 2011; 477(7363):220-4.
Radde, R. et al., Aβ42-driven cerebral amyloidosis in transgenic mice reveals early and robust pathology. EMBO Rep. 2006; 7(9):940-6.
Ravichandran, K.S. and Lorenz, U., Engulfment of apoptotic cells: signals for a good meal. Nat Rev Immunol. 2007; 7(12):964-74.
Reddy, V.P. et al., Oxidative stress in diabetes and Alzheimer's disease. J Alzheimers Dis. 2009; 16(4):763-74.
Rice, M.C. and O'Brien, S.J., Genetic variance of laboratory outbred Swiss mice. Nature. 1980; 283(5743):157-61.
Riss, T.L. et al., Cell Viability Assays, in Assay Guidance Manual, In G.S. Sittampalam, et al., Eds. Assay Guidance Manual [Internet]. Bethesda (MD): Eli Lilly & Co. and the National Center for Advancing Translational Sciences. 2004 (37 pages).
Robinson, S. et al., A European pharmaceutical company initiative challenging the regulatory requirement for acute toxicity studies in pharmaceutical drug development. Regul Toxicol Pharmacol. 2008; 50(3):345-52.
Roher, A.E. et al., β-Amyloid-(1-42) is a major component of cerebrovascular amyloid deposits: implications for the pathology of Alzheimer disease. Proc Natl Acad Sci USA. 1993; 90(22):10836-40.
Sabbagh, J.J. et al., Administration of donepezil does not rescue galanin-induced spatial learning deficits. Int J Neurosci. 2012; 122(12):742-7.
Sastre, M. et al., Interactions between APP secretases and inflammatory mediators. J Neuroinflam. 2008; 5:25 (11 pages).
Sather, S. et al., A soluble form of the Mer receptor tyrosine kinase inhibits macrophage clearance of apoptotic cells and platelet aggregation. Blood. 2007; 109(3):1026-33.
Schrijvers, D.M. et al., Phagocytosis of apoptotic cells by macrophages is impaired in atherosclerosis. Arterioscler Thromb Vasc Biol. 2005; 25(6):1256-61.
Scott, C.C. et al., Phagosome maturation: a few bugs in the system. J Membr Biol. 2003; 193(3):137-52.
Shafikhani, S. et al., Generation of large libraries of random mutants in Bacillus subtilis by PCR-based plasmid multimerization. Biotechniques; 1997; 23(2):304-10.
Slepko, N. and Levi, G., Progressive activation of adult microglial cells in vitro. Glia. 1996; 16(3):241-6.
Spatola Vega Data 1(3) Peptide Backbone Modifications (1982) (general review).
Spatola, A.F., Structure-Activity Relationships of Enkephalins Containing Serially Replaced Thiomethylene Amide Bond Surrogates. Life Sci. 1986; 38(14):1243-9.
Strick, D.J. et al., Mertk drives myosin II redistribution during retinal pigment epithelial phagocytosis. Invest Ophthalmol Vis Sci. 2009; 50(5):2427-35.
Tampellini, D. et al., Internalized antibodies to the Abeta domain of APP reduce neuronal Abeta and protect against synaptic alterations. J Biol Chem. 2007; 282(26):18895-906.
Tracy, M.A., Development and Scale-up of a Microsphere Protein Delivery System. Biotechnol Prog. 1998; 14(1):108-15.
Tsai, Y. et al., Ocular changes in TgF344-AD rat model of Alzheimer's disease. Invest Ophthalmol Vis Sci. 2014; 55(1):523-34.
Ubhi, K. and Masliah, E., Alzheimer's disease: recent advances and future perspectives. J Alzheimers Dis. 2013; 33 Suppl 1:S185-94.
Westwood, M.E. and Thornalley, P.J., Induction of synthesis and secretion of interleukin 1β in the human monocytic THP-1 cells by human serum albumins modified with methylglyoxal and advanced glycation end products. Immunol Lett. 1996; 50(1-2):17-21.
Wu, Y.C. et al., NUC-1, a *Caenorhabditis elegans* DNase II homolog, functions in an intermediate step of DNA degradation during apoptosis. Genes Dev. 2000; 14(5):536-48.
Zhang, Q. et al., Determination of Maximum Tolerated Dose and Toxicity of Inauhzin in Mice. Toxicol Rep. 2015; 2:546-554.
International Search Report and Written Opinion dated Feb. 3, 2017 by the International Searching Authority for Patent Application No. PCT/US2016/061605, which was filed on Nov. 11, 2016 and published as WO 2017/083700 on May 18, 2017 (Inventor—Nova Blanca Caberoy; Applicant—The Board of Regents of the Nevada System of Higher Education on behalf of the University of Nevada, Las Vegas) (8 pages).
International Preliminary Report on Patentability dated May 15, 2018 by the International Searching Authority for Patent Application No. PCT/US2016/061605, which was filed on Nov. 11, 2016 and published as WO 2017/083700 on May 18, 2017 (Inventor—Nova Blanca Caberoy; Applicant—The Board of Regents of the Nevada System of Higher Education on behalf of the University of Nevada, Las Vegas) (5 pages).
U.S. Appl. No. 62/254,846, filed Nov. 13, 2015, Nora Blanca Caberoy (University of Nevada, Las Vegas).
PCT, PCT/US2016/061605 (WO 2017/083700), Nov. 11, 2016 (May 18, 2017), Nora Blanca Caberoy (University of Nevada, Las Vegas).

\* cited by examiner

B1 protease cleavage

Capsid Items

Val Met Leu Gly Asp Pro | Leu Glu Val Leu Phe Gln Gly Pro | Gly Ser
GTG ATG CTC GGG GAT CCG CTG GAA GTG CTG TTT CAG GGC CCG GGC AGC
      BamH I

GS linker     Cloning sites     GS linker

| Gly Ser Gly Ser | Arg Pro Leu Asp Ile   *   Leu Glu | Gly Ser Gly Ser Gly
GGT TCA GGC TGG CGG CCG CTA GAT ATC TGA CTC GAG GGT AGT GGG AGC GGA
     Not I   EcoR V   Xho I

Biotinylation tag

| Leu Asn Asp Ile Phe Gln Ala Gln Lys Ile Gln | Trp His   *
TTA AAT GAT ATA TTT CAG GCA CAA AAA ATT CAA TGG CAT TAA CAATTC
                  EcoR I

TAGCTT TCGAG TAA....
Hind III

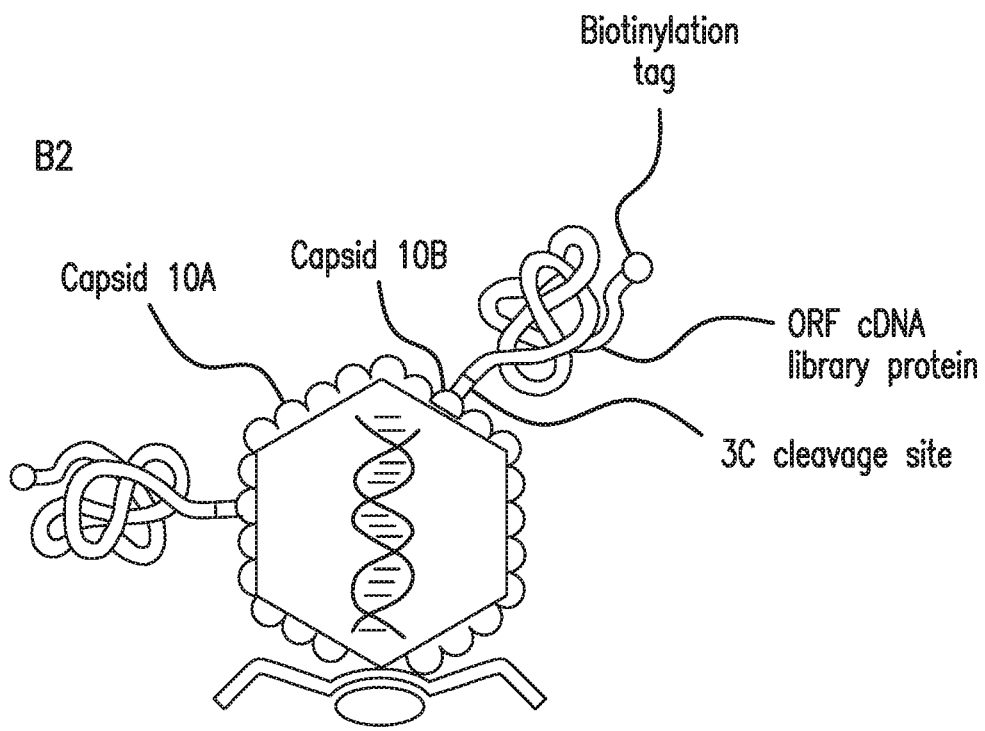

FIG. 3B

| Mutant peptides | Codon changes | Binding activity* against | |
|---|---|---|---|
| | | Aβ oligomer | Aβ fibril |
| 1 | E6R, L8S, L16S | 2.03 | 1.89 |
| 2 | E6R, L8S, L12S | 3.15 | 7.26 |
| 3 | L8S, L12S, N13S | 8.26 | 5.17 |
| 4 | L8R, L12S, L16S | 1.89 | 1.64 |
| 5 | 7GS, L8S, N13S, L16S | 10.82 | 6.67 |
| 6 | L12S, N13S, T15S, L16S | 18.78 | 5.39 |
| Ph–cAβBP | | $4.06 \times 10^4$ pfu | $3.12 \times 10^4$ pfu |
| Ph–VRAGE | | $4.77 \times 0^4$ pfu | $4.23 \times 10^4$ pfu |

*Binding activity was measured by phage plaque assay to verify the result of colorimetric assay. Data were normalized against Ph–cAβBP which contains the parental unevolved sequence.

FIG. 5

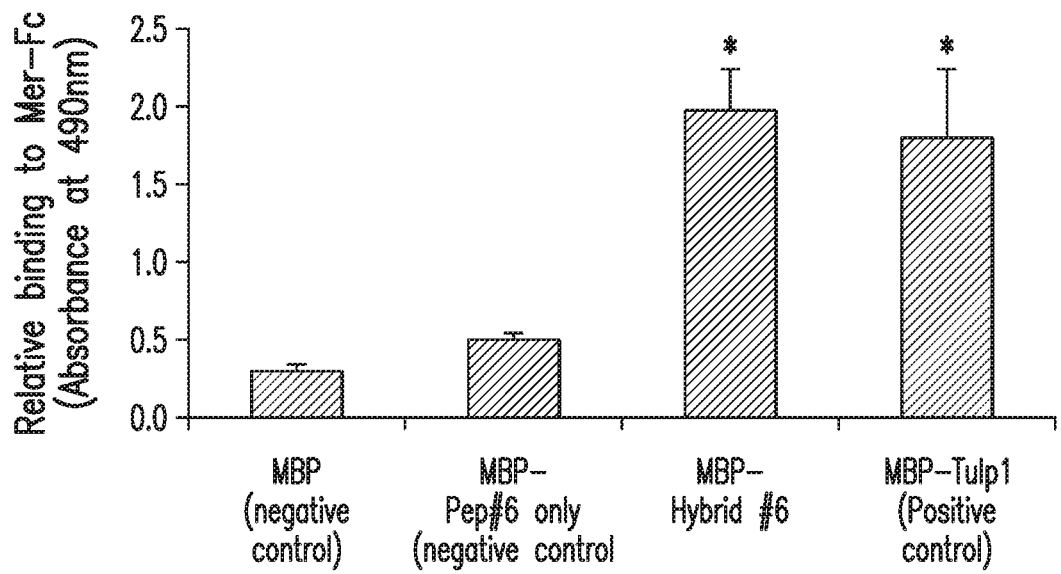

FIG. 6

| Animals | | Treatments | Sampling Time (months of treatment) 0 1 2 3 4 5 6 | # of mice (10/rep) |
|---|---|---|---|---|
| A. APP/ PS1 | Males | 1. Placebo (PBS) 2. Level 1 3. Level 2 | ↓ ↓ ↓ ↓ ↓ ↓ ↓ | 70 70 70 |
| | Females | 1. Placebo (PBS) 2. Level 1 3. Level 2 | ↓ ↓ ↓ ↓ ↓ ↓ ↓ | 70 70 70 |
| B. C57Bl/6 (no AD control) | Males Females | | ↓ ↓ ↓ ↓ ↓ ↓ ↓ | 70 70 |
| | | | Total: | 560 |

FIG. 12

LIGAND-GUIDED PHAGOCYTOSIS BASED THERAPY FOR TREATMENT OF ALZHEIMER'S DISEASE AND OTHER NEURODEGENERATIVE DISEASES

CROSS-REFERENCE TO RELATED APPLICATIONS

This application claims benefit of priority under 35 U.S.C. § 371 of International Application No. PCT/US2016/061605, filed on Nov. 11, 2016, which claims the benefit of U.S. Provisional Application No. 62/254,846, filed Nov. 13, 2015. The content of these earlier filed applications is hereby incorporated by reference herein in its entirety.

REFERENCE TO THE SEQUENCE LISTING

The sequence listing submitted May 9, 2018 as a text filed named "37474_00053 U2_Sequence_Listing," created on May 9, 2018, and having a size of 20,101 bytes is herein incorporated by reference in its entirety pursuant to 37 C.F.R. § 1..52(e)(5).

BACKGROUND

Alzheimer's disease is a progressive, neurodegenerative disease affecting approximately 5.3 million Americans and 44 million people worldwide. The exact cause of Alzheimer's disease is poorly understood and currently there is no cure; existing treatments produce modest cognitive enhancement addressing behavioral symptoms. Thus, effective disease-modifying pharmacological intervention for prevention and treatment are essential.

One of the major pathologic hallmarks of Alzheimer's is the buildup of amyloid beta aggregates and the formation of senile amyloid plaques in the brain. These small plaques disrupt cell-to-cell communication at synapses. Amyloid betas are primarily removed by the immunocompetent cells in the brain, called microglia, through the process of phagocytosis. Amyloid betas are recognized for engulfment primarily via microglial receptor for advanced glycation end products (RAGE). However, phagocytosis through RAGE results in the activation of an inflammatory pathologic cascade leading to sustained production of pro-inflammatory substances, exacerbation of neuro-inflammation, and the consequential death of neurons. The sustained inflammatory response has also been associated with accelerating amyloid beta pathology as well as the formation of neurofibrillary tangles.

There exists a need for a therapeutic strategy for clearing deleterious metabolic products to prevent Alzheimer's and other neurodegenerative diseases.

BRIEF SUMMARY

Disclosed herein is a therapeutic strategy for clearing deleterious metabolic products to prevent Alzheimer's and other neurodegenerative diseases.

Disclosed are compositions comprising an amyloid beta binding protein conjugated to a MerTK ligand. In some aspects, the MerTK ligand is Tubby, Tulp1, or a fragment thereof.

Disclosed are compositions comprising an amyloid beta binding protein conjugated to a MerTK ligand, the MerTK ligand is Tubby, Tulp1, or a fragment thereof, wherein the MerTK ligand comprises the amino acid sequence KRRKKK (SEQ ID NO:36) or KQKKK (SEQ ID NO:37).

In some aspects, the MerTK ligand consists of the amino acid sequence KRRKKK (SEQ ID NO:36) or KQKKK (SEQ ID NO:37).

Disclosed are compositions comprising an amyloid beta binding protein conjugated to a MerTK ligand, wherein the amyloid beta binding protein is mutated.

Disclosed are compositions comprising an amyloid beta binding protein conjugated to a MerTK ligand, wherein the amyloid beta binding protein comprises the amino acid sequence LDLSNEGLSGSLNGTLDKTLKQPL (SEQ ID NO:1).

Disclosed are compositions comprising an amyloid beta binding protein conjugated to a MerTK ligand, wherein the amyloid beta binding protein is mutated, wherein the mutated amyloid beta binding protein comprises the amino acid sequence LDLSNRGSSGSLNGTSDKTLKQPL (SEQ ID NO:28), LDLSNRGSSGSSNGTLDKTLKQPL (SEQ ID NO:29), LDLSNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), LDLSNEGLSGSSSGSSDKTLKQPL (SEQ ID NO:33), or any mutant shown in Table 1.

Disclosed are compositions comprising an amyloid beta binding protein conjugated to a MerTK ligand, wherein the amyloid beta binding protein is mutated, wherein the mutated amyloid beta binding protein consists of the amino acid sequence LDLSNRGSSGSLNGTSDKTLKQPL (SEQ ID NO:28), LDLSNRGSSGSSNGTLDKTLKQPL (SEQ ID NO:29), LDLSNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), LDLSNEGLSGSSSGSSDKTLKQPL (SEQ ID NO:33), or any mutant shown in Table 1.

Disclosed are compositions comprising an amyloid beta binding protein conjugated to a MerTK ligand, wherein the amyloid beta binding protein comprises the amino acid sequence PAECDWGKGGRWRLWPGASGKTEACGPPY (SEQ ID NO:2).

Disclosed are compositions comprising an amyloid beta binding protein conjugated to a MerTK ligand, wherein the amyloid beta binding protein is conjugated to a MerTK ligand with a linker. In some aspects, the linker is the amino acid sequence GSG.

Disclosed are compositions comprising an amyloid beta binding protein conjugated to a MerTK ligand, wherein the composition comprises more than one amyloid beta binding protein.

Disclosed are compositions comprising an amyloid beta binding protein conjugated to a MerTK ligand, wherein the composition comprises more than one MerTK ligand.

Disclosed are compositions comprising an amyloid beta binding protein conjugated to a MerTK ligand, wherein the composition comprises the amino acid sequence KRRKKKGSGKRRKKKGSGKRRKKKGSGLDL-SNEGLSGSLNGTLDKTLKQPLGSGLD LSNEGLSGSLNGTLDKTLKQPLGSGLDL-SNEGLSGSLNGTLDKTLKQPL (SEQ ID NO:34).

Disclosed are compositions comprising an amyloid beta binding protein conjugated to a MerTK ligand, wherein the composition comprises the amino acid sequence KRRKKKGSGKRRKKKGSGKRRKKKGSGLDL-SNEGLSGSSSGSSDKTLKQPLGSGLD LSNEGLSGSSSGSSDKTLKQPLGSGLDL-SNEGLSGSSSGSSDKTLKQPL (SEQ ID NO:35).

Disclosed are compositions comprising an amyloid beta binding protein conjugated to a MerTK ligand, further comprising a pharmaceutically acceptable carrier.

Disclosed are methods of clearing amyloid beta aggregates from a subject comprising administering a therapeutically effective amount of the compositions comprising an amyloid beta binding protein conjugated to a MerTK ligand.

Disclosed are methods of treating Alzheimer's Disease comprising administering to a subject in need thereof a therapeutically effective amount of the compositions comprising an amyloid beta binding protein conjugated to a MerTK ligand.

Disclosed are methods of treating Alzheimer's Disease comprising administering to a subject in need thereof a therapeutically effective amount of the compositions comprising an amyloid beta binding protein conjugated to a MerTK ligand in combination with an Alzheimer's disease therapeutic.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 5 is a Table showing the analysis of binding peptide mutant phage clones after IVE. Representative phage clones and their binding activity against Aβ are also shown.

FIG. 6 is a graph showing Hybrid #6 bound Mer-Fc at similar efficiency as Tulp1 (positive control). *p<0.05 compared to negative controls.

FIG. 12 is a Table of experimental treatments. Dosage can be based on the optimum dose established in the pilot study. As indicated, larger replications will be needed to accommodate the cognitive/behavioral tests and histopathological analyses (at least 10 mice per group). To ensure that sufficient peptide concentration will be delivered in the brain, and to eliminate the uncertainty of systemic pharmacokinetic variables we will perform a direct intracranial delivery of the peptide using iPRECIO implantable pump (SMP-300 specifically for mice; iPRECIO, Durect Corp). The pump works based on miniature peristaltic action and can be implanted subcutaneously. Because the pump is programmable, it can deliver an accurate controlled flow at constant rate as low as 1 ul/hour (0.1-Iul), and has been found to be more precise and consistent. Treatments can be done for 6 months. Downward arrows indicate sampling points for behavioral, histopathological and other assessments.

DETAILED DESCRIPTION

Figure 1:
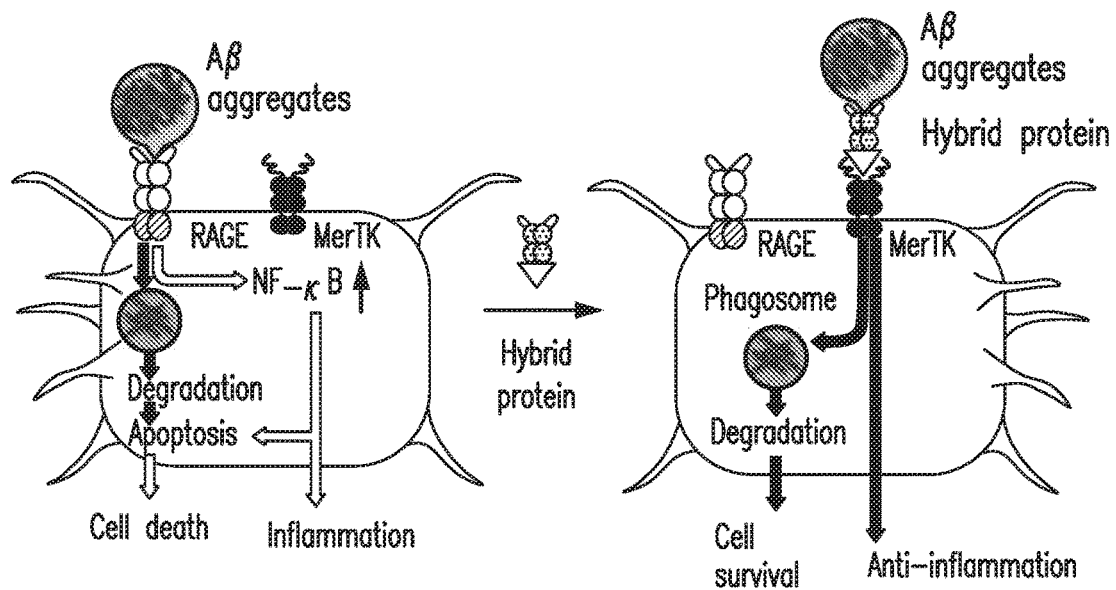
FIG. 1 is a schematic diagram for clearing amyloid beta through the MerTK pathway.
Figure 2:
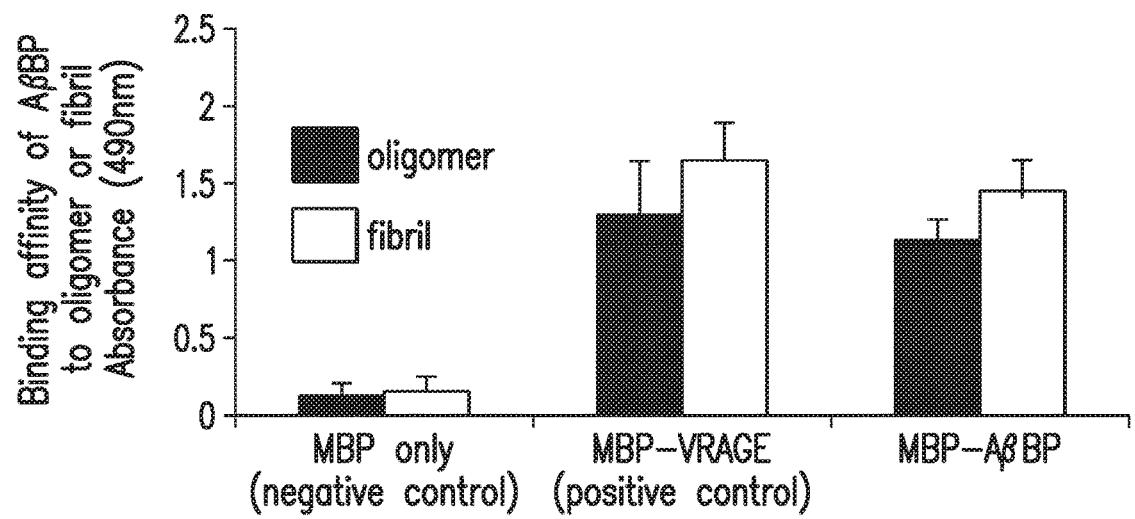
FIG. 2 is a graph showing the Aβ binding peptide (AβBP) containing a consensus sequence binds to Aβ oligomers or fibrils at similar efficiency with VRAGE.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a amyloid beta binding protein is disclosed and discussed and a number of modifications that can be made to a number of molecules including the amyloid beta binding protein are discussed, each and every combination and permutation of the amyloid beta binding protein and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed A. Definitions It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an amyloid beta binding protein" includes a plurality of such amyloid beta binding proteins, reference to "the MerTK ligand" is a reference to one or more MerTK ligands and equivalents thereof known to those skilled in the art, and so forth.

The phrase "amyloid beta binding protein" or "amyloid beta binding peptide" as used herein refers to a protein or peptide that is capable of binding amyloid beta.

A "MerTK ligand" as used herein refers to a protein, peptide, or fragment thereof, that is capable of binding MerTK. Examples of MerTK ligands include, but are not limited to, Tubby and Tulp1. Thus, fragments of Tubby and Tulp1 that retain the ability to bind to MerTK can also be MerTK ligands.

As used herein, "therapeutically effective amount" is meant to mean a sufficient amount of the composition to provide the desired effect. For example, an effective amount of an amyloid beta binding protein conjugated to a MerTK ligand can be an amount that provides a therapeutic affect and, in some aspects, can provide sustained therapeutic effects after withdrawal of the treatment. An therapeutically effective amount of an amyloid beta binding protein conjugated to a MerTK ligand is an amount that is able to cause a benefit illustrated by a decrease in amyloid beta aggregates or a decrease in Alzheimer's disease symptoms, or an amount that allows for a sustained therapeutic effect after withdrawal of the amyloid beta binding protein conjugated to a MerTK ligand. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "therapeutically effective amount." However, an appropriate "therapeutically effective amount" can be determined by one of ordinary skill in the art using only routine experimentation.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

As used herein, "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient".

As used herein, "treat" is meant to mean administer one of the disclosed compositions to a subject, such as a human or other mammal (for example, an animal model), that has a disease (e.g. Alzheimer's Disease), in order to prevent or delay a worsening of the effects of the disease or condition, or to partially or fully reverse the effects of the disease.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

B. Peptides and Conjugates

Disclosed are amyloid beta binding proteins and MerTK ligands. In some aspects, the amyloid beta binding proteins are conjugated to the MerTK ligands.

1. Amyloid Beta Binding Proteins

In some aspects, the amyloid beta binding protein can be wild type or can be mutated. The mutated amyloid beta protein can be a variant of wild type that has been modified or altered. In some aspects, wild type amyloid beta binding protein comprises the amino acid sequence LDLSNEGLSGSLNGTLDKTLKQPL (SEQ ID NO:1) or PAECDWGKGGRWRLWPGASGKTEACGPPY (SEQ ID NO:2). In some aspects, wild type amyloid beta binding protein comprises the amino acid sequence of any of those shown in table 1. In some aspects, mutated amyloid beta binding protein comprises the amino acid sequence LDLSNRGSSGSLNGTSDKTLKQPL (SEQ ID NO:28), LDLSNRGSSGSSNGTLDKTLKQPL (SEQ ID NO:29), LDLSNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), LDLSNEGLSGSSSGSSDKTLKQPL (SEQ ID NO:33), or any of the mutants shown in table 1. In some aspects, mutated amyloid beta binding protein consists of the amino acid sequence LDLSNRGSSGSLNGTSDKTLKQPL (SEQ ID NO:28), LDLSNRGSSGSSNGTLDKTLKQPL (SEQ ID NO:29), LDLSNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), LDLSNEGLSGSSSGSSDKTLKQPL (SEQ ID NO:33), or any of the mutants shown in table 1.

TABLE 1

Wild type (original) and mutant amyloid beta binding protein sequences.

| SEQ ID NO: | WILD TYPE |
|---|---|
| 1 | LDLSNEGLSGSLNGTLDKTLKQPL |
| 2 | PAECDWGKGGRWRLWPGASGKTEACGPPY |
| 3 | KIGKVVFPDCIASDPFKLVVDDTLSYVAEIRGILPRSD |
| 4 | MAVWAKVRSALAVEAVVGDKADKVALD |
| 5 | LGVQYAKGISQGELVVSSAPVQDFAPIAKLLI |

TABLE 1-continued

Wild type (original) and mutant amyloid beta binding protein sequences.

| SEQ ID NO: | |
|---|---|
| 6 | RLGRGLLAKLDLKWLKLERDGTAAEKLHEDLKKILREELRRELLL |
| 7 | MKIGIGKGEEIVPEEEKPSAKKLKLKKALGLVEGLF |
| 8 | PSFDQKLESRLQAELSPGLGHAIEAIFLFADDAKEGLAEDLLGEKA |
| 9 | KKGKLGEPFQLIGLLILARFIIQKKKLDALKEVLELATKRLLKFDLKLEERDLKKQELLELQELRKDVLLADLANQDDDEALLRADKEADILELENADK |
| 10 | VGGDVVEGTSHSGLITDLGVVNGGRALLSGPEPLNGTDLPALLAAGLLFELSEAPEILVGEYSTVSLVAVGAEVPLEDYLDEGDKHGEALSDYWDQLLELSILL |
| 11 | VGGEGISGTIFNIYGGFIPGKLRRLPDAEIWGGLSLGGDQRFGDGTAVIGLSVSLKSGGAELVAELYVDPGVSSQPEE |
| 12 | MLVDGGKLGVLAKQLKEYLAFDRDLDDLVFKAKIQVNDGALGVISNLLFGGGIVGQIL |
| 13 | SLALLVETNELDDAAVELIRKLGGTDAELKIILAGDGIDGISWPALGNEAGDLVGSSGIAGGKPVLPDEAFVRLSVNASGGFVDGIKEGPVVL |
| 14 | GDGPSDLEVVRLITPGQALAPFTNAGQAAAVPRSEGESMIAVSHNMLPQVSSEVVEGYATKNETENETLCMKIGPPIVGE |
| 15 | RPDEIVGVWSSYLGLGFVLSKAVILELLRNWFGKQSGAYLDYLHGSVALLGDKNMGRKLSQS |
| 16 | HLLIDKGVAGGPGFDTVASLAETEKARGPEVSTLAKEDFAKTIGELGAGPKTSKAVVGEGGKEIPLGPGKSYP |
| 17 | SSSLFQLPTDGKLVQALITNLYGSALDGYEVRDLELIMEKRLVISINGRIPAEFNQDLGLRLLLT |
| MUTANT | |
| 18 | PAECDWGKGGRWRLWPSASGKTEACGPPY |
| 19 | PAECDWGKGGRWRDWPGASGKTEACGPPY |
| 20 | PAECDWGKGGRWRLWPGSSGKTEACGPPY |
| 21 | PAECDWKKGGRWRLWPGASGKTEACGPPY |
| 22 | PAECDWGKGGLWRLWPGASGKTEACGPPY |
| 23 | PAECDWGKGRRWRSWPGASGKTEACGPPY |
| 24 | PAECDWGKGGRWRLWPGASGKTDACGPPY |
| 25 | PAECDWGKGGRWRLRPGASGKTEACGPPY |
| 26 | PAECDWGKGGRWRLWPGASLKTEACGPPY |
| 27 | PAECDWGKKGRWRLWPGASGKTEACGPPY |

2. MerTK Ligands

In some aspects, the MerTK ligands can be Tubby or Tulp1. In some aspects, the MerTK ligand can be KRRKKK (SEQ ID NO:36) or KQKKK (SEQ ID NO:37). In some aspects, the MerTK ligand can be Gas6 and Protein S.

3. Conjugates

Disclosed are amyloid beta binding proteins conjugated to MerTK ligands. The amyloid beta binding proteins conjugated to MerTK ligands can be any of the disclosed amyloid beta binding proteins conjugated to MerTK ligands. Disclosed are amyloid beta binding proteins conjugated to a MerTK ligand, wherein the amyloid beta binding protein can be conjugated to a MerTK ligand with a linker. In some aspects, the linker is the amino acid sequence GSG.

Disclosed are amyloid beta binding proteins conjugated to a MerTK ligand, wherein the amyloid beta binding protein can be conjugated to a MerTK ligand with a linker, wherein there can be more than one amyloid beta binding protein. Disclosed are amyloid beta binding proteins conjugated to a MerTK ligand, wherein the amyloid beta binding protein can be conjugated to a MerTK ligand with a linker, wherein there can be more than one MerTK ligand. Thus, in some aspects, there can be more than one MerTK ligand and more than one amyloid beta binding protein. In the scenario of multiple amyloid beta binding proteins or multiple MerTK ligands or a combination thereof, at least one amyloid beta binding protein is conjugated to a MerTK ligand. In some aspects, an amyloid beta binding protein can be conjugated to another amyloid beta binding protein. In some aspects, a MerTK ligand can be conjugated to another MerTK ligand. In some aspects, the amyloid beta binding protein and the MerTK ligands alternate throughout the peptide.

Disclosed are amyloid beta binding proteins conjugated to MerTK ligands wherein the conjugate comprises the amino acid sequence KRRKKKGSGKRRKKKGSGKRRKKKGSGLDL-SNEGLSGSLNGTLDKTLKQPLGSGLD LSNEGLSGSLNGTLDKTLKQPLGSGLDL-SNEGLSGSLNGTLDKTLKQPL (SEQ ID NO:34).

Disclosed are amyloid beta binding proteins conjugated to MerTK ligands wherein the conjugate comprises the amino acid sequence KRRKKKGSGKRRKKKGSGKRRKKKGSGLDL-SNEGLSGSSSGSSDKTLKQPLGSGLD LSNEGLSGSSSGSSDKTLKQPLGSGLDL-SNEGLSGSSSGSSDKTLKQPL. (SEQ ID NO:35)

Disclosed are amyloid beta binding proteins conjugated to MerTK ligands wherein a MerTK ligand can be conjugated to any of the disclosed amyloid binding proteins. In some aspects, multiple MerTK ligands are present. In some aspects, multiple amyloid binding proteins are present. In some aspects, multiple MerTK ligands and multiple amyloid binding proteins are present.

4. Linkers

Any suitable linker can be used with the disclosed compositions. For example, the linker, GSG, can be used. The peptide linkages can be selected from the group consisting of: —CH2NH—, —CH2S—, —CH2-CH2-, —CH═CH— (cis and trans), —COCH2-, —CH(OH)CH2-, —CH2SO—, etc. by methods known in the art and further described in the following references: Spatola (1983) p. 267 in Chemistry and Biochemistry of Amino Acids, Peptides, and Proteins, B. Weinstein, eds., Marcel Dekker, New York; Spatola (1983) Vega Data 1(3) Peptide Backbone Modifications. (general review); Morley (1980) Trends Pharm Sci. pp. 463-468 (general review); Hudson et al. (1979) Int. J. PeptProt Res. 14:177-185 (—CH2NH—, CH2CH2-); Spatola et al. (1986) Life Sci. 38:1243-1249 (—CH2-S); Hann, (1982) J. ChemSoc Perkin Trans I 307-314 (—CH—CH—, cis and trans); Almquist et al. (1980) J. Med. Chem. 23:1392-1398 (—COCH2-); Jennings-White et al. (1982) Tetrahedron Lett. 23:2533 (—COCH2-); Szelke et al., European Appln. EP 45665 (1982) CA: 97:39405 (1982) (—CH(OH)CH2-); Holladay et al. (1983) Tetrahedron Lett. 24:4401-4404 (—C(OH)CH2-); and Hruby (1982) Life Sci., 31:189-199 (—CH2-S—)).

One particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In one aspect, the linker is a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g., esterase cleavable linker), ultrasound-sensitive linkers, x-ray cleavable linkers, etc.

5. Variants

The amyloid beta binding protein and the MerTK ligand can be modified or altered. For example, the amyloid beta binding protein and the MerTK ligand can be mutated, scrambled, and/or reverse-oriented.

Numerous other variants or derivatives of the peptides disclosed herein are also contemplated. For example, scrambled peptides can also be reverse-oriented, or can be in a switched orientation. Additionally, reverse-oriented peptides can be in a switched orientation. All other combinations of the disclosed peptides are also contemplated. As used herein, the term "analog" is used interchangeably with "variant" and "derivative." Variants and derivatives are well understood to those of skill in the art and can involve amino acid sequence modifications. Such, amino acid sequence modifications typically fall into one or more of three classes: substantial; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog. Substitutional variants are those in which at least one residue has been removed and a different residue inserted in its place. Such substitutions generally are made in accordance with Tables 2 and 3 and are referred to as conservative substitutions.

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties are those in which: (a) the hydrophilic residue, e.g. seryl or threonyl, is substituted for (or by) a hydrophobic residue, e.g., leucyl, isoleucyl, phenylalanyl, valyl or alanyl; Tryptophan, Tyrosinyl (b) a cysteine or proline is substituted for (or by) any other residue; (c) a residue having an electropositive side chain, e.g., lysyl, arginyl, or hystidyl, is substituted for (or by) an electronegative residue, e.g. glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

TABLE 2

Table 2 - Amino Acid Substitutions

| Original Residue | Non-limiting Exemplary Conservative Substitutions |
|---|---|
| Ala | Ser |
| Arg | Gly; Gln; Lys |
| Asn | Gln; His |
| Asp | Glu |
| Cys | Ser |
| Gln | Asn; Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

TABLE 3

Amino Acid Abbreviations

| Amino Acid | Abbreviations |
|---|---|
| Alanine | Ala (A) |
| Allosoleucine | AIle |
| Arginine | Arg (R) |
| Asparagine | Asn (N) |
| Aspartic Acid | Asp (D) |
| Cysteine | Cys (C) |
| Glutamic Acid | Glu (E) |
| Glutamine | Gln (Q) |
| Glycine | Gly (G) |
| Histidine | His (H) |
| Isolelucine | Ile (I) |
| Leucine | Leu (L) |
| Lysine | Lys (K) |
| Phenylalanine | Phe (F) |
| Praline | Pro (P) |
| Pyroglutamic Acid | PGlu (U) |
| Serine | Ser (S) |
| Threonine | Thr (T) |
| Tyrosine | Tyr (Y) |
| Tryptophan | Trp (W) |
| Valine | Val (V) |

It is understood that one way to define the variants and derivatives of the disclosed proteins herein is to define them in terms of homology/identity to specific known sequences. Specifically disclosed are variants of amyloid beta binding protein and other proteins or peptides herein disclosed which have at least 70% or at least 75% or at least 80% or at least 85% or at least 90% or at least 95% homology to the amyloid beta binding protein specifically recited herein. Those of skill in the art readily understand how to determine the homology of two proteins.

The peptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. (See Proteins-Structure and Molecular Properties 2nd Ed., T.E. Creighton, W.H. Freeman and Company, New York (1993); Posttranslational Covalent Modification of Proteins, B.C. Johnson, Ed., Academic Press, New York, pp. 1-12 (1983)).

Variants can also include peptidomimetics. As used herein, "peptidomimetic" means a mimetic of a function of a protein which includes some alteration of the normal peptide chemistry. Peptidomimetics typically are short sequences of amino acids that in biological properties mimic one or more function(s) of a particular protein. Peptide analogs enhance some property of the original peptide, such as increases stability, increased efficacy, enhanced delivery, increased half-life, etc. Methods of making peptidomimetics based upon a known polypeptide sequence is described, for example, in U.S. Pat. Nos. 5,631,280; 5,612,895; and 5,579, 250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N—ε-Boc-N-α-CBZ-L-lysine, N—ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

C. Nucleic Acids

As this specification discusses various peptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

D. Compositions

Disclosed are compositions comprising an amyloid beta binding protein conjugated to a MerTK ligand.

In some aspects, the MerTK ligand can be, but is not limited to, Tubby, Tulp1, or a fragment thereof that binds to MerTK. In some aspects, the MerTK ligand comprises the amino acid sequence KRRKKK (SEQ ID NO:36) or KQKKK (SEQ ID NO:37). In some aspects, the MerTK ligand consists of the amino acid sequence KRRKKK (SEQ ID NO:36) or KQKKK (SEQ ID NO:37). In some aspects, there can be more than one MerTK ligand present in the conjugate.

In some aspects, the amyloid beta binding protein can be wild type or can be mutated. The mutated amyloid beta protein is variant of wild type that has been modified or altered. In some aspects, wild type amyloid beta binding protein comprises the amino acid sequence LDL-SNEGLSGSLNGTLDKTLKQPL (SEQ ID NO:1) or PAECDWGKGGRWRLWPGASGKTEACGPPY (SEQ ID NO:2). In some aspects, mutated amyloid beta binding protein comprises the amino acid sequence LDL-SNRGSSGSLNGTSDKTLKQPL (SEQ ID NO:28), LDL-SNRGSSGSSNGTLDKTLKQPL (SEQ ID NO:29), LDL-SNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), LDLSNEGLSGSSSGSSDKTLKQPL (SEQ ID NO:33). In some aspects, mutated amyloid beta binding protein consists of the amino acid sequence LDL-SNRGSSGSLNGTSDKTLKQPL (SEQ ID NO:28), LDL-SNRGSSGSSNGTLDKTLKQPL (SEQ ID NO:29), LDL-SNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), LDLSNEGLSGSSSGSSDKTLKQPL (SEQ ID NO:33).

Disclosed are compositions comprising an amyloid beta binding protein conjugated to a MerTK ligand, wherein the amyloid beta binding protein can be conjugated to a MerTK ligand with a linker. In some aspects, the linker is the amino acid sequence GSG.

Disclosed are compositions comprising an amyloid beta binding protein conjugated to a MerTK ligand, wherein the composition comprises more than one amyloid beta binding protein.

Disclosed are compositions comprising an amyloid beta binding protein conjugated to a MerTK ligand, wherein the composition comprises more than one MerTK ligand. Thus, in some aspects, the composition comprises more than one MerTK ligand and more than one amyloid beta binding protein. In the scenario of multiple amyloid beta binding proteins or multiple MerTK ligands or a combination thereof, at least one amyloid beta binding protein is conjugated to a MerTK ligand. In some aspects, an amyloid beta binding protein can be conjugated to another amyloid beta binding protein. In some aspects, a MerTK ligand can be conjugated to another MerTK ligand. In some aspects, the amyloid beta binding protein and the MerTK ligands alternate throughout the peptide.

Disclosed are compositions comprising an amyloid beta binding protein conjugated to a MerTK ligand, wherein the composition comprises the amino acid sequence KRRKKKGSGKRRKKKGSGKRRKKKGSGLDL-SNEGLSGSLNGTLDKTLKQPLGSGLD LSNEGLSGSLNGTLDKTLKQPLGSGLDL-SNEGLSGSLNGTLDKTLKQPL (SEQ ID NO:34). Disclosed are compositions comprising an amyloid beta binding protein conjugated to a MerTK ligand, wherein the composition comprises the amino acid sequence KRRKKKGSGKRRKKKGSGKRRKKKGSGLDL-SNEGLSGSSSGSSDKTLKQPLGSGLD LSNEGLSGSSSGSSDKTLKQPLGSGLDL-SNEGLSGSSSGSSDKTLKQPL (SEQ ID NO:35).

Disclosed are compositions comprising an amyloid beta binding protein conjugated to a MerTK ligand, further comprising a pharmaceutically acceptable carrier.

By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A.R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

E. Methods

1. Method of Clearing Amyloid Beta

A method of clearing amyloid beta aggregates from a subject comprising administering to a subject in need thereof a therapeutically effective amount of the disclosed compositions. Clearing amyloid beta aggregates refers to the removal, elimination, or degradation of amyloid beta aggregates. In some aspects, clearing amyloid beta aggregates means reducing the amount of amyloid beta aggregates in the subject compared to the amount of amyloid beta aggregates present prior to administering any of the disclosed compositions.

In some aspects, clearing amyloid beta aggregates from a subject comprises clearing amyloid beta aggregates from tissue or cells. For example, clearing amyloid beta aggregates can include removing the aggregates from the brain.

2. Methods of Treating Alzheimer's Disease

Disclosed are methods of treating Alzheimer's Disease comprising administering to a subject in need thereof a therapeutically effective amount of any one of the disclosed compositions.

Disclosed are methods of treating Alzheimer's Disease comprising administering to a subject in need thereof a therapeutically effective amount of any one of the disclosed compositions in combination with a known Alzheimer's disease therapeutic.

In one aspect of the disclosed methods, the Apo E mimetics can be administered alone or in combination with one or more additional therapeutic agents. The additional therapeutic agents can be selected based on the severity of the disease. A description of the various classes of suitable pharmacological agents and drugs may be found in Goodman and Gilman, The Pharmacological Basis of Therapeutics, (11th Ed., McGraw-Hill Publishing Co.) (2005). For example, pharmaceutical compositions containing amyloid beta binding proteins conjugated to MerTK ligands can be administered in combination with one or more known therapeutic agents for treating any amyloid beta related disease, such as but not limited to, Alzheimer's disease. Therapeutic agents for treating atherosclerosis include, but are not limited to, cholesterol-lowering agents, HDL elevating agents, blood pressure-lowering agents, blood thinning agents (i.e. medicines that prevent blood clots), anti-inflammatory agents, and anti-atherogenic agents. Examples of cholesterol-lowering agents include, but are not limited to, a cholesterol absorption inhibitor, a bile acid sequestrant, a fibrate, a PCSK9 inhibitor, a microsomal triglyceride transfer protein inhibitor, an apolipoprotein B synthesis inhibitor, or a CETP inhibitor.

The disclosed compositions can be administered prior to, in conjunction with, or after any known Alzheimer's therapeutics.

3. Administration/Delivery

In the methods described herein, administration or delivery of the compositions can be via a variety of mechanisms. As defined above, disclosed herein are methods of treating and methods of clearing amyloid beta aggregates from a subject. The methods include compositions containing any one or more of the polypeptides or nucleic acids described herein that can also include a carrier such as a pharmaceutically acceptable carrier. For example, disclosed are compositions comprising the conjugate comprising the amyloid beta binding protein linked to a MerTK ligand disclosed herein, and a pharmaceutically acceptable carrier.

The disclosed peptides and conjugates can be in solution or in suspension (for example, incorporated into microparticles, liposomes, or cells). These compositions can be targeted to a particular cell type via antibodies, receptors, or receptor ligands. One of skill in the art knows how to make and use such targeting agents with the disclosed compositions. A targeting agent can be a vehicle such as an antibody conjugated liposomes; receptor mediated targeting of DNA through cell specific ligands, and highly specific retroviral targeting of cells in vivo. Any such vehicles can be part of the compositions herein. For example, targeting agents that direct the compositions to the tissue containing the amyloid beta aggregates can be included in the compositions.

Any suitable route of administration can be used for the disclosed compositions. Suitable routes of administration can, for example, include topical, enteral, local, systemic, or parenteral. For example, administration can be epicutaneous, inhalational, enema, conjunctival, eye drops, ear drops, alveolar, nasal, intranasal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc. The disclosed compositions can be used in and with any other therapy.

Unlike typical peptide formulations, the disclosed peptides comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) Biotechnol. Prog., 14: 108; Johnson et al. (1996) Nature Med. 2: 795; Herbert et al. (1998), Pharmaceut. Res. 15, 357) a dry powder composed of biodegradable polymeric microspheres containing the active agent in a polymer matrix that can be compounded as a dry formulation with or without other agents.

The ProLease microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., $-40°$ C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

F. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for conjugating an amyloid beta binding protein to a MerTK ligand, the kit comprising amyloid beta binding proteins, MerTK ligands, and a linker. The kits also can contain solutions and buffers for making the conjugates.

The disclosed kits can also include instructions for how to make or use the disclosed conjugates.

Examples

A. Example 1: Generation of Aβ Binding Peptides (AβBPs) with the Highest Binding Affinity to A Engagement of RAGE with Aβ causes the activation of a cellular cascade that results in the nuclear translocation of NF-κB and sustained release of pro-inflammatory cytokines. In transgenic mouse AD animal models (e.g. APP), overexpression of RAGE in microglia increased the production of proinflammatory mediators such as IL-1(3 and TNF-α after stimulation of Aβ. These elevated levels of proinflammatory molecules due to microglia RAGE-Aβ interaction are believed to cause the neuronal damage or death that leads to deficits in learning and memory.

Evolved peptides highly specific to Aβ have been generated that can be used as decoys to prevent the interaction of Aβ with RAGE, and possibly to other Aβ natural receptors. Combining the Aβ binding peptide that will serve as the phagocytic prey binding domain with a receptor binding motif to create a chimeric protein that can specifically recognize MerTK on one end, and Aβ on another, will direct the clearance of Aβ from RAGE to MerTK pathway. The rationale for using a chimeric ligand rather than a natural ligand is to test the concept of phagocytosis-based therapy based on knowledge of phagocytosis-bridging molecules, which are more advantageous than natural bridging molecules. For example, since Aβ accumulation is the natural cause of neuronal toxicity in AD, the phagocytic prey-binding domain with Aβ binding activity is preferred for the chimeric ligand. The same concept can be applied to other diseases. For example, if CEP accumulation in retina causes AMD, a chimeric ligand with a CEP-binding peptide as the phagocytic prey binding domain could be designed. Moreover, the receptor binding domain can be conveniently selected according to pathogenesis. If tissue damage is coupled with inflammation, the MerTK-specific receptor binding domain can be chosen for chimeric ligand due to MerTK-mediated immunosuppression. However, if patients already have immunodeficiency syndrome, a chimeric ligand can be designed choosing a receptor-binding domain from other phagocytic receptors. Thus, phagocytic ligands can be designed, according to pathogenesis, with different combinations of receptor-binding domains and phagocytic prey-binding domains for therapy.

i. Generation of AβBP Peptide Consensus Sequence.

To be an effective decoy against RAGE, an Aβ-binding peptide should be able to bind Aβ with much higher affinity than RAGE. A bioinformatics approach was used to generate an AβBP-containing consensus by aligning sequences of Aβ-binding proteins in the literature and subsequently subjecting the consensus to in vitro protein evolution (IVE) and phage display screening to select for Aβ-binding peptides with high affinity to Aβ. An exhaustive search of the literature was conducted for known Aβ-binding proteins and aligned 128 sequences using NCBI COBALT software. COBALT is a protein multiple sequence alignment tool that finds a collection of pairwise constraints derived from a conserved domain database, a protein motif database, and sequence similarity, using RPS-BLAST, BLASTP, and PHI-BLAST. Using COBALT, a 24 amino acid AβBP was generated containing a consensus sequence. The capacity of the AβBP to bind Aβ was tested by cloning it to a maltose binding protein (MBP) fusion vector. The MBP-AβBP fusion protein was expressed in *E. coli* cells.

Studies have shown that the soluble Aβ oligomers are the most toxic form of Aβ, causing both acute memory-compromising synaptic toxicity and inducing chronic neurodegenerative processes. Because of the above characteristics, and because they exist at very low levels in the AD brain, soluble Aβ oligomers constitute an optimal immunotherapeutic target. However, none of the Aβ immunotherapies currently in clinical development selectively target soluble Aβ oligomers, and their lack of efficacy is not unexpected considering their selectivity for monomeric or fibrillar Aβ (or both) rather than soluble Aβ oligomers. Moreover, most of the studies on Aβ toxicity were done using the fibrillar form. Thus, this study tested the binding of the Aβ binding peptide against both oligomeric and fibrillar Aβ42. Aβ42 was chosen for this study because of its pathological significance. Aβ40 and Aβ42 peptides are the major species in Aβ production, but Aβ42 is predominant in neuritic plaques of AD patients and shows a higher propensity to aggregate and form amyloid fibrils in vitro. Familial AD mutations result in an increase in the Aβ42:Aβ40 ratio in cell culture and mouse models and elevated plasma levels of Aβ42 seem to be correlated with AD.

The different forms (oligomers, fibrils) of Aβ42 were prepared. Briefly, synthetic Aβ42 (Anaspec) was prepared by resuspending lyophilized Aβ42 in hexafluoroisopropanol (HFIP), dried under a nitrogen stream and stored as a film at −20° C. Immediately prior to use, Aβ was resuspended in DMSO and sonicated for 10 minutes. The oligomers were prepared by diluting the Aβ with phenol-red free DMEM-F12 and incubating for 24 hours at 4° C. without shaking. The fibrils were similarly prepared but incubated at 37° C. for 24 hours with vigorous shaking. Next, ELISA plates were coated with Aβ oligomers or fibrils, blocked with PVA. The MBP-AβBP, control MBP, or MBP-VRAGE (containing the V domain of RAGE as positive control) was incubated with immobilized Aβ in ELISA plates. After washing, bound proteins were incubated with anti-MBP monoclonal antibodies, followed by HRP-conjugated secondary antibodies and quantified by a colorimetric assay. The results showed that the AβBP binds both oligomeric and fibrillar Aβ at similar efficiency with VRAGE control (FIG. 2).

ii. In Vitro Protein Evolution and Phage Display Biopanning.

To be an effective RAGE competitor, an Aβ binding peptide that is able to bind Aβ with much higher affinity than RAGE was needed. To generate the highly competitive AP binding peptide, the consensus sequence was subjected to in vitro protein evolution by PCR mutagenesis and combined with phage display selection. Briefly, the 72 bp cDNA of the peptide that contains consensus (above) was used as the initial scaffold for IVE. The cDNA was amplified and randomly mutated by PCR. The random mutation rate was controlled to give a predicted average of ~3 bp mutations in the original template. PCR primers were embedded with restriction enzyme cleavage sites that anneal to T7 phage vector restriction sites. The mutated PCR products were digested with proper restriction enzymes, re-ligated in-frame into T7phage vector, and packaged to generate an "evolved" Aβ binding peptide phage library.

iii. In Vitro Phage Selection.

The newly "evolved" Aβ binding peptide phage library was screened against Aβ oligomers and fibrils to identify mutated peptides with high binding affinity to Aβ. Phage selection was carried out with a few modifications: Briefly, Aβ oligomers or fibrils were coated on ELISA plates for overnight at 4° C., washed and blocked with PVA. To minimize plate-binding phages, subtraction was performed by first incubating the library in mock coated wells (no Aβ) blocked with PVA. After 30 minutes, the subtracted phage library was incubated with Aβ oligomers or fibrils immobilized on ELISA plates. The wells were washed, and bound phages were eluted with 3C protease at 4° C. overnight. The eluted phages were quantified by plaque assay to determine the total phages (FIG. 3A). The first round of selection produced more Aβ-oligomer specific clones than fibril-specific phage clones (676 for oligomer vs. 163 for fibrils; total 839).

A dual phage display was previously developed to replace tedious plaque assays for quantification of T7 phage. The capsid/envelop of T7 phage consists of 415 copies of capsid 10A and/or 10B. Each engineered phage displays ~5-15 copies of library protein fused to the C-terminus of capsid 10B, with the remaining ~400 copies of capsid 10A provided by the host bacteria. Thus, a BLT7Bio bacterial strain expressing biotinylation tag in the C-terminus of capsid 10A was expressed. Growing the phages in BLT7Bio bacteria will produce phages co-displaying ~5-5-copies of capsid 10B-library fusion proteins and >400 copies of biotin-tagged capsid 10A on the same phage surface. This allows for the functional analysis of library proteins because the fusion protein can bind to its target, while those bound phages expressing >400 copies of biotin tag on their surface can be sensitively quantified using Streptavidin-conjugated HRP.

Figure 3A:
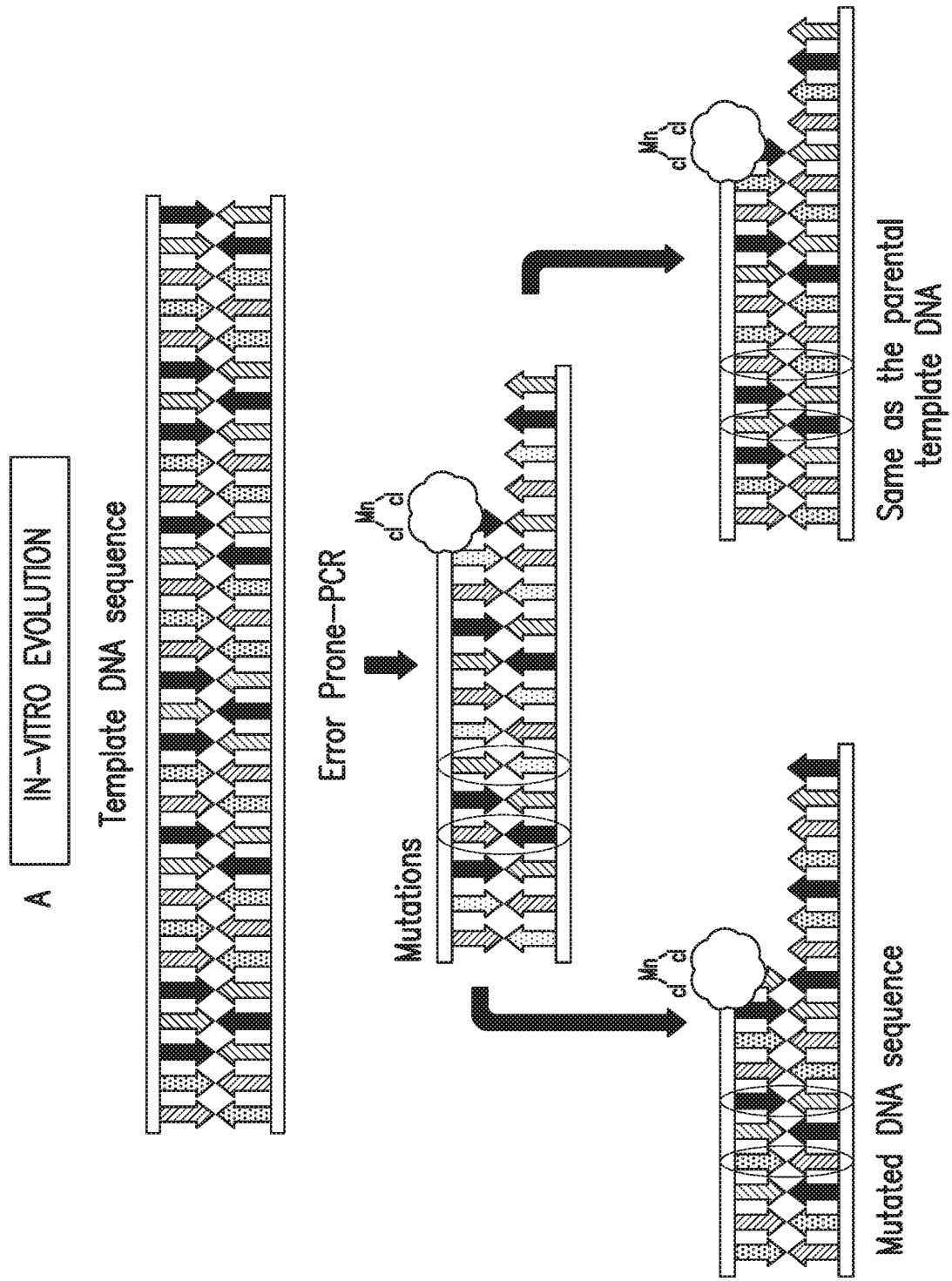
FIGS. 3A, 3B, and 3C show the generation of high affinity Aβ-binding peptides by in-vitro evolution and ORF phage display. (A) Error-prone PCR involves the addition of Mn, which inhibit the fidelity of DNA Pol by replacing its preferred co-factor, Mg. (B1) Sequence of T7Bio3C phage display vector. Mutant PCR fragments were ligated in-frame of capsid 10B of T7 phage. (B2) Features of T7 phage display (B3) Mutant AβBPs were litigated to T7Bio3C, packaged and plated in BLT5615 bacteria for plaque assay to determine titer. (B4) Individual phage clones with mutant AβBP were amplified in BLTBio bacteria and used for binding to immobilized Aβ oligomers (oAβ) or fibrils (faβ). Binding was detected through HRP-conjugated streptavidin. (C1) Bound phages quantified by colorimetric assay using streptavidin-conjugated HRP. (C2) Dual phage display. The capsid of T7 phage consists of 415 copies of capsid 10A and/or 10B. Each engineered phage displays ~5-15 copies of library protein fused to the C-terminus of capsid 10B, with the remaining ~400 copies of capsid 10A provided by the host bacteria. Growing the phages in BLT7Bio bacteria produce phages co-displaying ~5-5-copies of capsid 10B-library fusion proteins and >400 copies of biotin-tagged capsid 10A on the same phage surface. This allows for sensitive quantification of bound phages expressing >400 copies of biotin tag on their surface by colorimetric assay using Streptavidin-conjugated HRP.
Figure 3B:
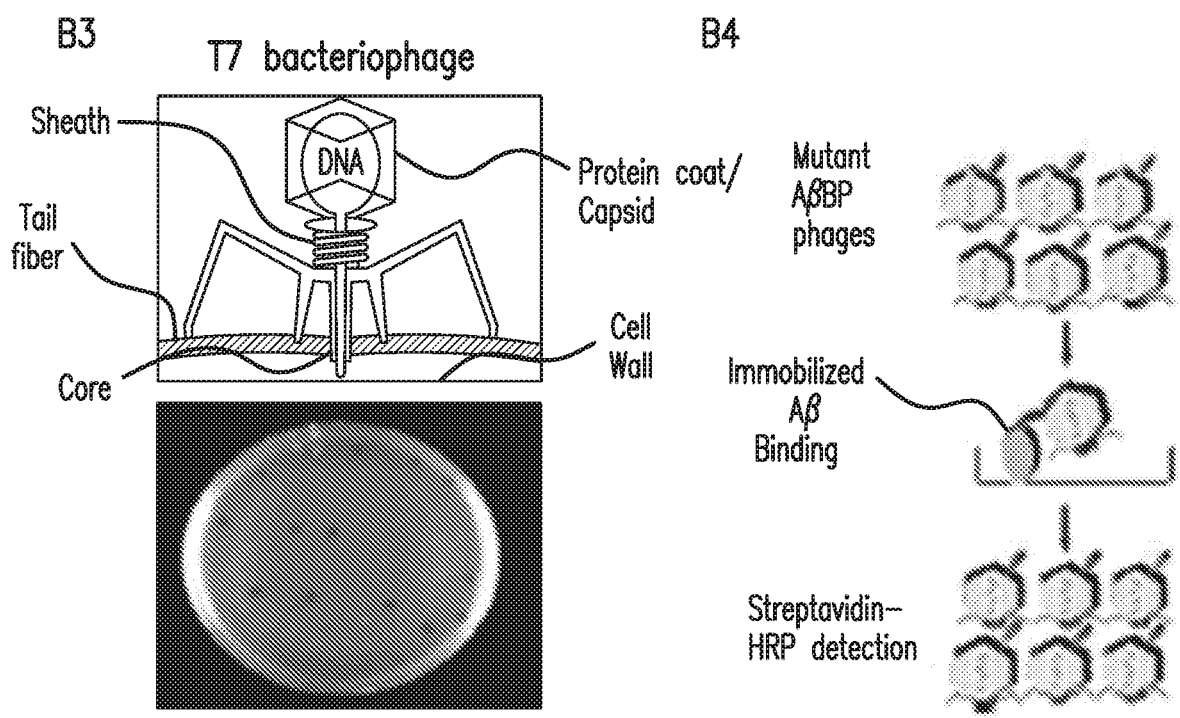
Figure 3C:
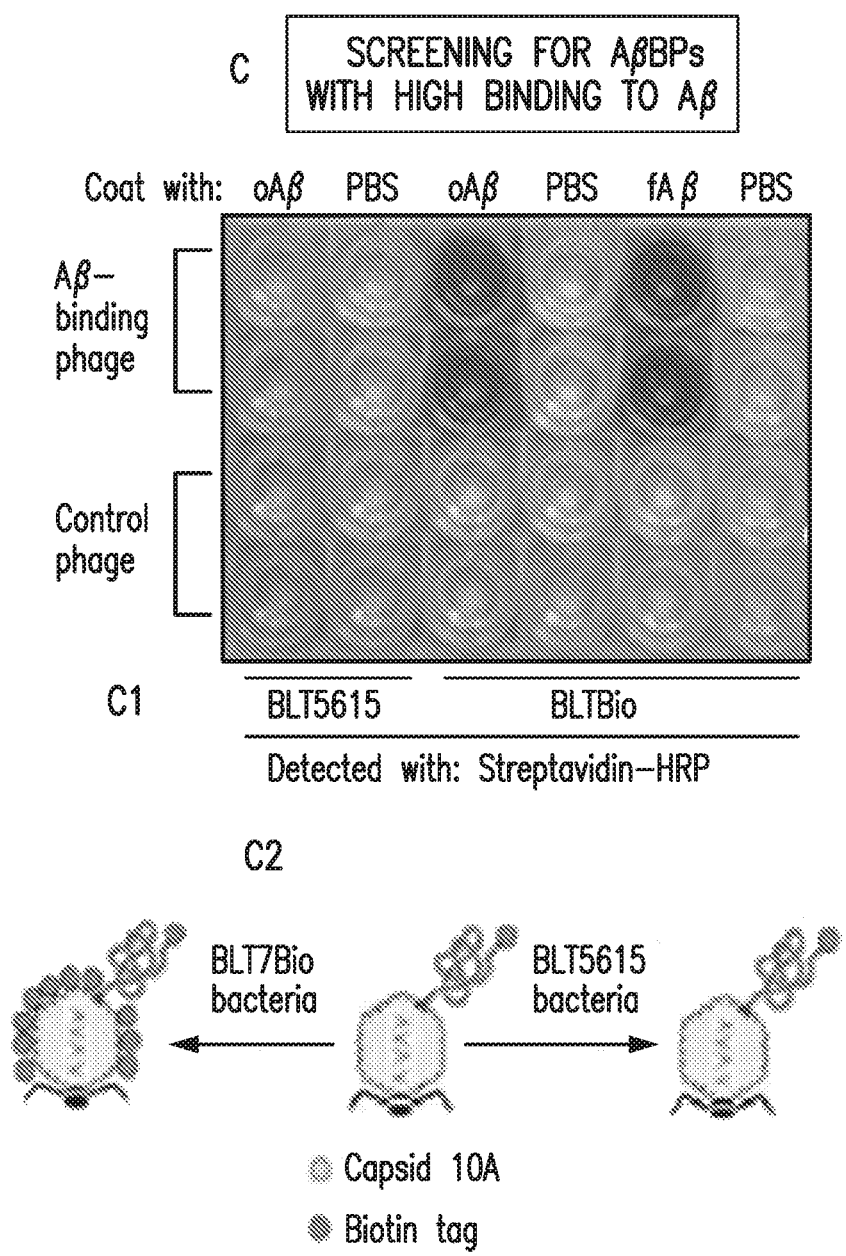
Figure 4:
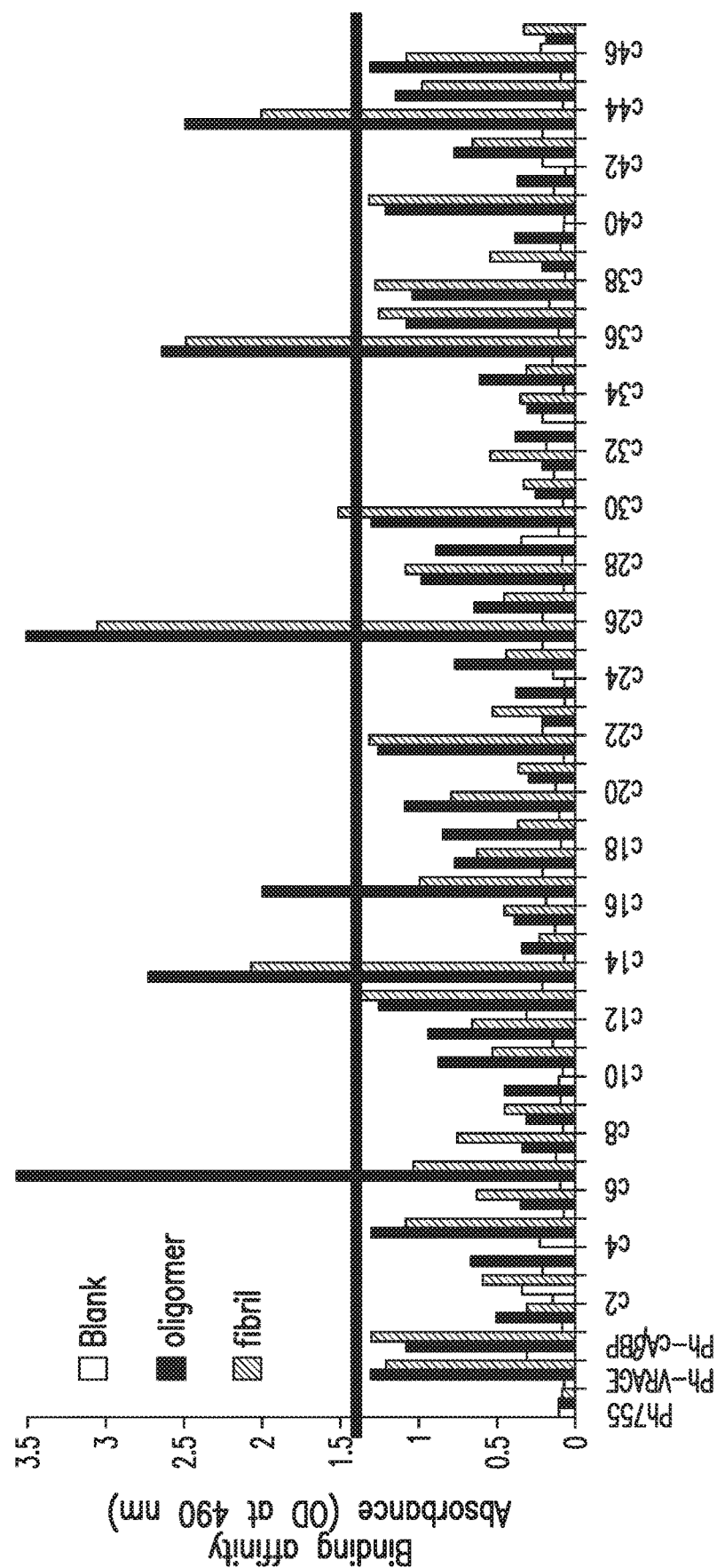
FIG. 4 shows the affinity screening against an Aβ oligomer or fibril of some individual phages carrying evolved Aβ binding peptides after IVE (B). Ph755 is the negative control phage without cDNA insert. Ph-VRAGE is the positive control. Ph-cAβBP is the unevolved parental consensus peptide. Phages with higher activities than Ph-VRAGE and Ph-cAβBP were sequenced to identify residues that were mutated after IVE.

Using dual phage display, 78 phage clones were identified with activities higher than the control unevolved parental Aβ binding peptide and VRAGE phages (FIG. 3B). Sequence analysis of these clones revealed point mutations producing changes in amino acid codons. Fifteen of the evolved peptides had higher binding affinity to either oligomeric or fibrillar Aβ compared to the parental unevolved peptide or VRAGE (FIG. 4). The peptides with the highest activities were fused to a tubby/Tulp1 minimum phagocytic domain to create K/R(X)1-2 KKK-AβBP hybrid proteins. Hybrid Protein #6 was the lead hybrid since Peptide #6 gave the highest binding to oligomeric Aβ (FIG. 4).

B. Example 2: Hybrid Proteins Facilitate Aβ Clearance Through MerTK and not RAGE-Mediated Phagocytosis Pathway Activation of MerTK triggers an intracellular signaling cascade that induces cytoskeletal rearrangement and uptake of apoptotic cells or cellular debris and their colocalization with the phagosomes. The hallmark of MerTK activation includes receptor autophosphorylation leading to myosin II (NMMIIA) redistribution in the phagocytes and co-localization with phagocytosed cargos.

These studies determine whether MerTK is autophosphorylated in the presence or absence of the hybrid proteins. The specificity of Aβ clearance to MerTK by blocking protein-guided phagocytosis with Mer-Fc (disulfide homodimer of MerTK extracellular domain fused to human IgG1 Fc domain), anti-MerTK, or RAGE antibodies can be tested. The role of MerTK in the clearance using microglia isolated from wild-type and MerTK−/− mice can be delineated by analyzing biomarkers for MerTK activation and downstream signaling such as colocalization of phagocytosed Aβ with NMMIA and phagosome markers.

1. Experimental Design i. Aβ Clearance can be MerTK-Dependent

Previous studies have shown that both tubby and Tulp1 activate MerTK by acting as bridging molecules with their N-terminal minimal phagocytic domain of K/R(X)1-2 KKK associating with MerTK and the C-terminal acting as phagocytic prey binding domain for apoptotic cells and cellular debris. Here, chimeric proteins were created with the K/R (X)1-2 KKK fused to evolved Aβ binding peptides to generate a K/R(X)1-2 KKK-AβBP hybrid proteins. The K/R(X)1-2 KKK part of the hybrid can trigger MerTK receptor activation while the AβBP part can sequester Aβ. Together, the two domains can facilitate Aβ clearance through MerTK-dependent phagocytosis and not through inflammatory RAGE.

Since Peptide #6 had the highest binding to Aβ oligomers (see FIG. 4) the initial hybrid construct was made with Peptide #6 fused to the K/R(X)1-2 KKK motif and expressed the protein as an MBP fusion. The initial construct was made up of three modules of K/R(X)1-2 KKK fused to two modules of evolved Peptide #6 to create Hybrid Protein #6. This is because mouse Tulp1, with the most vigorous activity for MerTK, contains five K/R(X)1-2 KKK motifs. Also, the AβBPs were tested in phage platform and typically a phage displays ~5-15 proteins on its capsid surface. Thus, the higher number of motifs can generate a much tighter binding with the targets. However, the most ideal permutation for copies of both K/R(X)1-2 KKK and AβBP protomers in the chimeric proteins can be refined further based on the binding kinetic analysis of several peptide constructs measured against Mer-Fc and Aβ oligomers, respectively.

The capacity of the Hybrid #6 to recognize the receptor MerTK was tested by binding to Mer-Fc (R&D Systems). The data shows that Hybrid #6 binds Mer-Fc at similar efficiency as the positive control Tulp1 (FIG. 5). Next, whether Hybrid #6 can facilitate uptake of Aβ in BV2 microglial cells was tested. Fluorescently labeled Aβ42 oligomers (Anaspec) were prepared. BV2 cells were incubated with Aβ42 oligomers for 3 hours in the presence or absence of Hybrid #6 or control proteins, washed and then imaged under a confocal microscope. The data shows that the hybrid protein was able to facilitate engulfment of Aβ oligomers (FIG. 6). To test for specificity to MerTK, an excessive amount of Mer-Fc (2.5 µg/ml) was added to Hybrid Protein #6 and Aβ, 30 minutes prior to incubation with BV2 cells. There was a significant decrease in the uptake of Aβ, indicating that Mer-Fc prevented association of the hybrid protein with the MerTK receptor.

ii. MerTK Autophosphorylation, NMMIIA Redistribution, and Cargo Trafficking Through the Phagocytic Pathway.

Ligand-induced MerTK activation results in the receptor autophosphorylation, followed by rearrangement of cytoskeletal proteins and extension of the plasma membrane for engulfment, leading to the redistribution and colocalization of nonmuscle myosin II (NMMIIA) with ingested cargo. Hybrid Protein #6 can facilitate engulfment of Aβ. To investigate whether the hybrid protein can induce MerTK activation, MerTK phosphorylation assay can be performed. Briefly, BV2 cells or primary microglia can be cultured in 293 SFM II medium for 2 hours prior to the assay to reduce the background of MerTK activation. The cells can be incubated with purified MBP-Hybrid #6 or control MBP for 30 minutes at 37° C. After washing, the cells can be lysed and lysates can be incubated with anti-MerTK antibodies, followed with protein A resin. The protein A resin can be precipitated by centrifugation, washed and analyzed by western blot using anti-phospho-MerTK or anti-MerTK antibodies, followed with HRP-conjugated secondary antibodies and chemiluminescence detection. Primary microglia can be prepared.

To determine whether Hybrid Protein #6 induces MerTK-dependent cytoskeletal reorganization, the redistribution of NMMII-A heavy chain can be characterized. Fluorescently labeled Aβ oligomers or fibrils can be prepared. Phagocytosis assay can be performed. Briefly, cells can be incubated with Aβ oligomers or fibrils in the presence or absence of chimeric ligands or control proteins (similar to FIG. 6). After 3 hours, cells can be washed to remove unphagocytosed Aβ. Microglia with phagocytosed cargos can be fixed with buffered formalin, permeabilized and immunostained with anti-NMMIIA antibodies, followed by Texas-Red-labeled secondary antibodies. The intracellular fluorescence signals can be analyzed by confocal microscopy.

Hybrid Protein #6 facilitates uptake of Aβ oligomers (FIG. 6). The question is whether it directs the internalization of Aβ to the phagocytic pathways or non-specifically via other internalization pathways? After recognition and engulfment, the process of cargo clearance is not complete. Recent studies suggest that events downstream from internalization, collectively called phagosome maturation, influence the phagocytic capacity of a cell to internalize additional targets. Maturation occurs by fusion of phagosomes with lysosomes and other organelles until the cargo is eventually fully digested. Phagosome maturation is a highly conserved biological process and has been well characterized with various biomarkers for early and late phagosomes. To test whether the hybrid protein directs ingested cargos to phagosomes, colocalization of ingested Aβ with subcellular distribution of Rab7, an early phagosome marker, and Lamp-1, a late phagosome marker, can be analyzed in both BV2 and primary microglia. Phagocytosis and immunohistochemical procedures can be performed.

iii. Blockade of Hybrid Protein-Mediated Phagocytosis to Determine the Specificity to MerTK.

The specificity of Aβ clearance to MerTK can be tested in the presence or absence of the hybrid proteins by blocking protein-guided phagocytosis. Briefly, hybrid proteins can be pre-incubated with excess Mer-Fc before the above phagocytosis assays. Presumably, the K/R(X)1-2 KKK motif on the hybrid protein can bind to Mer-Fc and can block the K/R(X)1-2 KKK-MerTK interaction during the phagocytosis assays. As a complementary approach, BV2 or primary microglia can be preincubated with antibodies against MerTK to block MerTK receptor binding sites before the phagocytosis assays to inhibit the interaction of hybrid proteins with MerTK. In a separate experiment, BV2 or primary microglia can be pre-incubated with RAGE antibodies to demonstrate that MerTK phagocytosis is not inhibited by blocking the receptor RAGE. Mock antibodies and Fc can be included as negative controls.

To further delineate the role of MerTK in the clearance, microglia isolated from wild-type and MerTK−/− mice can be used. Primary microglia can be prepared from the brain of postnatal Day 1 wild-type and MerTK−/− mice (Jackson Laboratories). The microglia can be used for a phagocytosis assay with Aβ in the presence or absence of hybrid protein as above. In addition, Aβ can be pre-incubated with the hybrid protein, washed to remove unbound proteins, then incubated with wild-type microglia in the presence or absence of excess Mer-Fc (to serve as dominant negative) or an Fc control to block MerTK-dependent phagocytosis. MerTK activation can also be blocked by antibodies against MerTK. Phagocytosed fluorescent Aβ can be analyzed by confocal microscopy and quantified as above. MerTK activation with receptor autophosphorylation induced by the hybrid proteins in the presence or absence of Mer-Fc can be further characterized by western blot using anti-phospho-MerTK and anti-MerTK antibodies. Alternatively, MerTK knockdown can be performed using shRNA in BV2 or wild-type primary microglia.

iv. Binding Kinetic Analyses.

It is ideal for the K/R(X)1-2 KKK-AβBP chimera to have both high affinity binding to MerTK and Aβ oligomers, as well as the ability to freely pass through the blood-brain barrier. To determine the most ideal permutation for copies of both K/R(X)1-2 KKK and AβBP protomers in the chimeric proteins, the affinities of several peptide constructs can be measured for Mer-Fc and Aβ oligomers, respectively. Specifically, peptides can be synthesized containing 1-5 copies of K/R(X)1-2 KKK that are separated by flexible glycine-serine linkages (note that the length of linkers can also be tested for their effect on high affinity binding). Similarly, peptides containing 1-3 copies of AβBP protomers can also be synthesized with flexible linkers and their affinities measured for binding to Aβ oligomers or fibrils. The equilibrium dissociation constants for binding using fluorescence polarization spectroscopy (FP) can be determined. FP is observed when a fluorescently labeled ligand binds to a much larger target, which significantly reduces the rotation of ligand with respect to time. This signal is easily captured in a spectrofluorimeter. This approach can be used for the following reasons: (1) FP has been successfully used to characterize the interactions of several ligands to the extracellular domains of receptor tyrosine kinases; (2) the molecular weight of Mer-Fc homodimer is 157.4 kDa, and the molecular weights of the largest proteins are less than 10 kDa, which should produce favorable signal-to-noise in a FP experiment for a variety of fluorescent dyes; and (3) the FP binding assay occurs in solution and is therefore not influenced by mass transfer effects that can confound results from chip-based binding methods. Several fluorescent dyes that are ideal for FP can be incorporated into the peptides during commercial synthesis. Binding assays can involve a constant concentration of labeled peptide and the titration of Mer-Fc for the K/R(X)1-2 KKK peptides or Aβ oligomers for the AβBP peptides. Binding curves can be fit to the data using non-linear regression and can also be optimized to the binding model that best fits the data. Critical negative controls, such as the titration of unlabeled peptide that is expected to outcompete the binding of labeled peptide to the target protein, can also be conducted. In the unlikely event that an FP signal is not observed, the binding affinities can be measured using isothermical calorimetry, which also has the advantage of estimating the thermodynamic parameters of binding in addition to affinity.

v. Data Analysis.

All data can be analyzed using the Students' t-test. Data for multiple groups can be subjected to a one-way ANOVA post-hoc test using IBM SPSS Software.

2. Results (a) The hybrid proteins can facilitate phagocytosis of Aβ42 and can induce MerTK autophosphorylation, resulting in the rearrangement of non-muscle myosisn and the colocalization of ingested cargos with phagosome biomarkers; (b) The hybrid protein-mediated phagocytosis can be blocked by Mer-Fc or antibodies against MerTK; (c) Phagocytosis can also be abolished in microglia from mice deficient in MerTK, and MerTK phagocytosis cannot be inhibited by blocking the RAGE pathway using anti-RAGE antibodies. The result can demonstrate that Aβ clearance can be re-routed into the MerTK phagocytic pathway using the guidance of specific ligands. These outcomes are important because the strategy of ligand-guided MerTK-dependent phagocytic clearance can be applicable to other deleterious metabolic products, such as CEP and drusen in AMD, AGEs in aged retina and diabetic retinopathy with hyperglycemia or myelin debris in Multiple Sclerosis.

C. Example 3: Hybrid Proteins Facilitate Aβ Clearance without Inducing Inflammatory Responses Leading to Neuronal Death Aβ accumulation elicits an acute microglial response through two signaling pathways: NF-κB and ERK-2/AP. These pathways converge at the transcriptional level to induce expression of pro-inflammatory cytokines such as IL-1β, IL-6 and tumor necrosis factor alpha (TNF-α). NF-κB is an important upstream modulator of pro-inflammatory cytokines and iNOS (inducible Nitric Oxide Synthase) expression. Both pro-inflammatory cytokines and oxidative damage are observed early in the progression of AD and can be detected prior to fibrillar Aβ deposition in the AD brain. Microglial activation can also be detected in vivo in around half of patients with mild cognitive impairment.

1. Experimental Design i. Inflammatory Mediators and Oxidative Activity.

NF-κB activation can be analyzed in microglia incubated with Aβ oligomers or fibrils in the presence or absence of the hybrid proteins, or controls (as indicated above for MerTK-dependence). Microglial activation can be determined by quantifying the release of pro-inflammatory and anti-inflammatory cytokines using a Multi-Analyte ELISArray Kit (Qiagen). Complementary to ELISA assay, the expression of some of the most common inflammatory (iNOS, IL-1β, IL-6, TNF-α, IFNγ) and anti-inflammatory factors (IL-4, IL-10, IL-receptor agonists, TGF-β) can be determined using real time RT-PCR. The expression of superoxide dismutase and catalase (CAT) can also be investigated to evaluate the oxidative activity in the cells. SOD and CAT are important for the elimination of reactive oxygen species.

Figure 7:
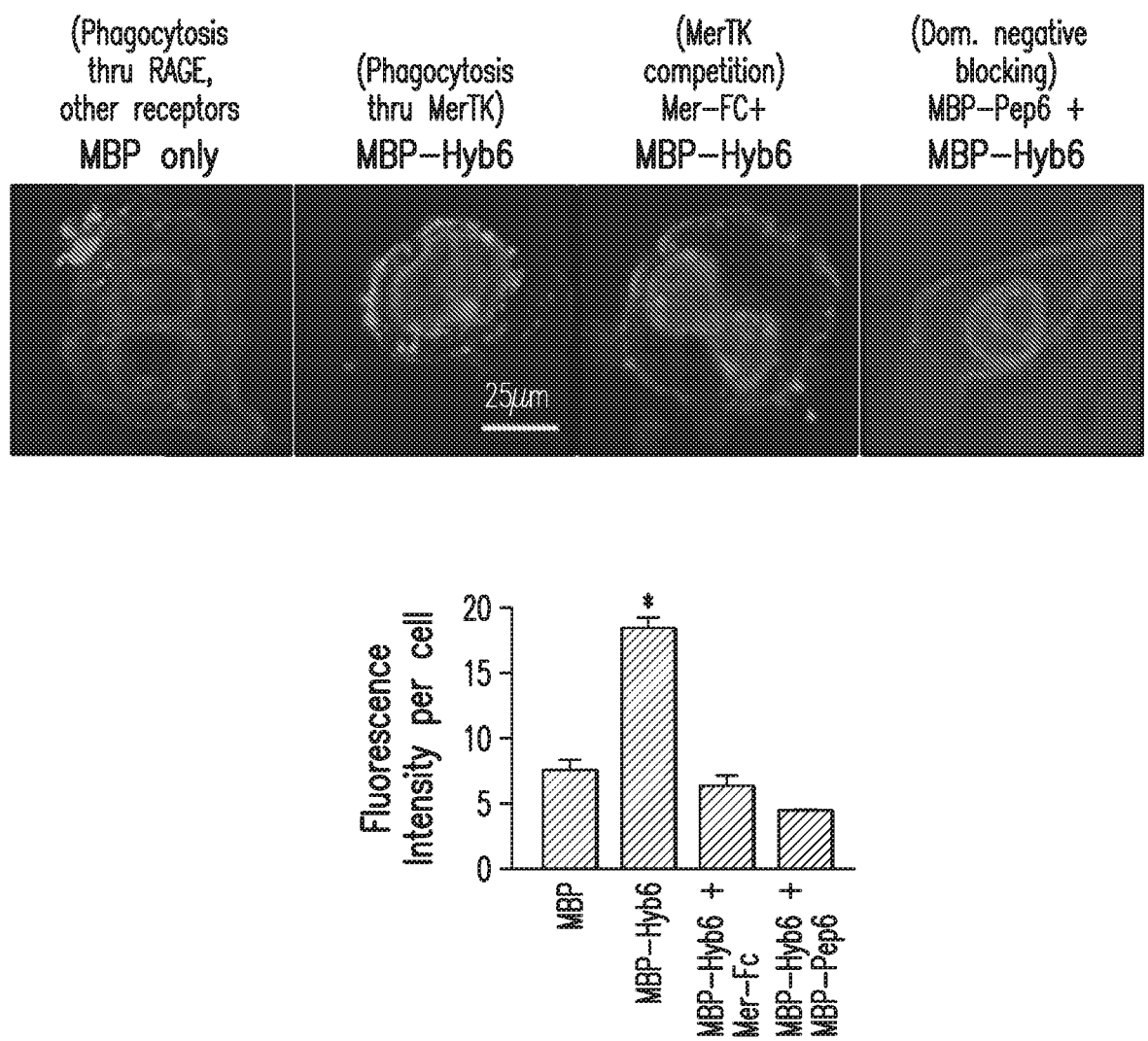
FIG. 7 shows Hybrid #6 facilitated phagocytosis of Aβ oligomers. Engulfment was inhibited by Mer-Fc or Peptide #6 (Pep6). Red is phalloidin staining for actin filaments. Blue is DAPI nuclear staining. Relative fluorescence intensity per cell was determined using ImageJ by manually tracing the outline of individual phagocytes with the corresponding green fluorescence quantified. More than 50 cells per group were quantified. *P<0.05.
Figure 8:
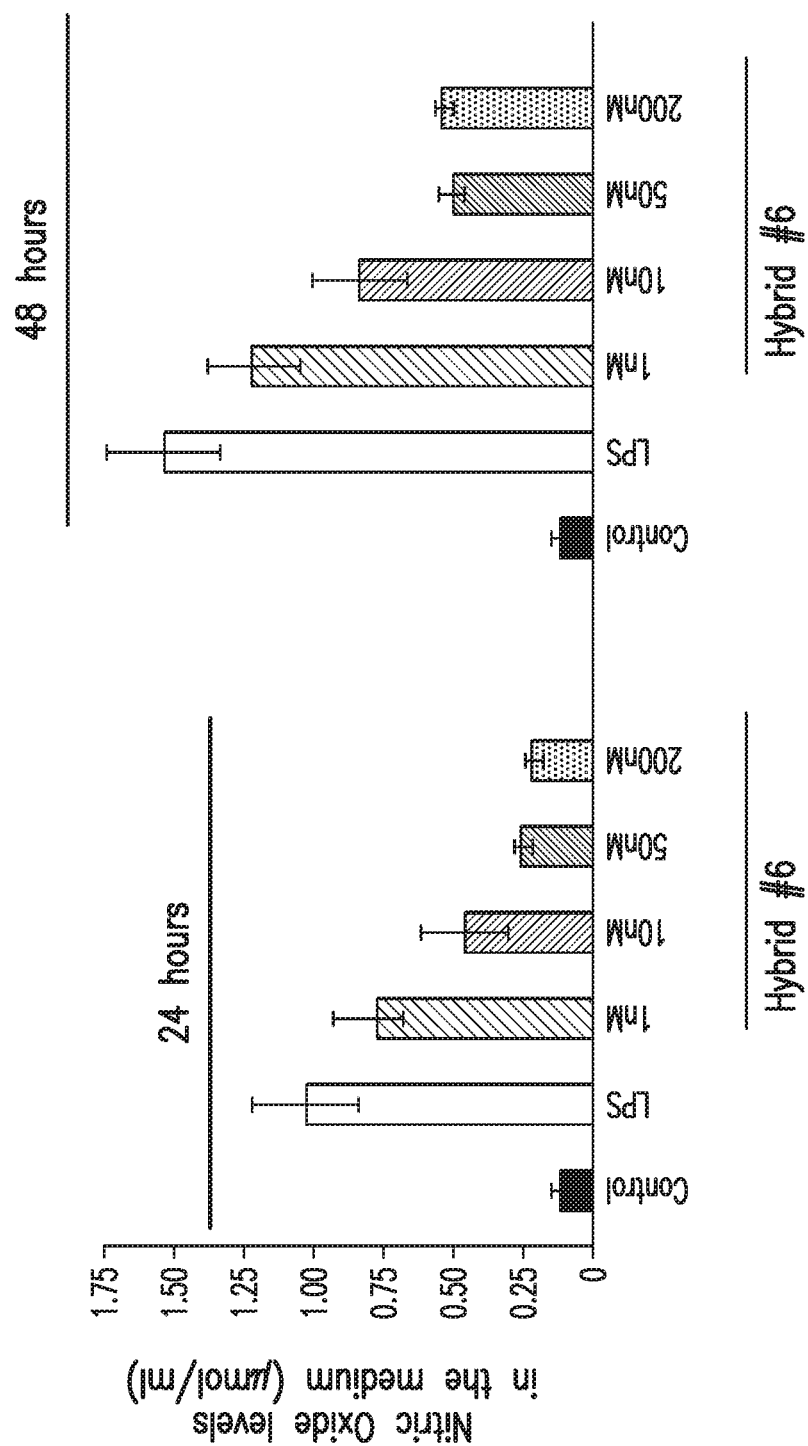
FIG. 8 is a graph showing dose dependent reduction on nitric oxide produced by LPS (1 µg/ml) stimulated BV2 cell line treated with Hybrid #6.
Figure 9:
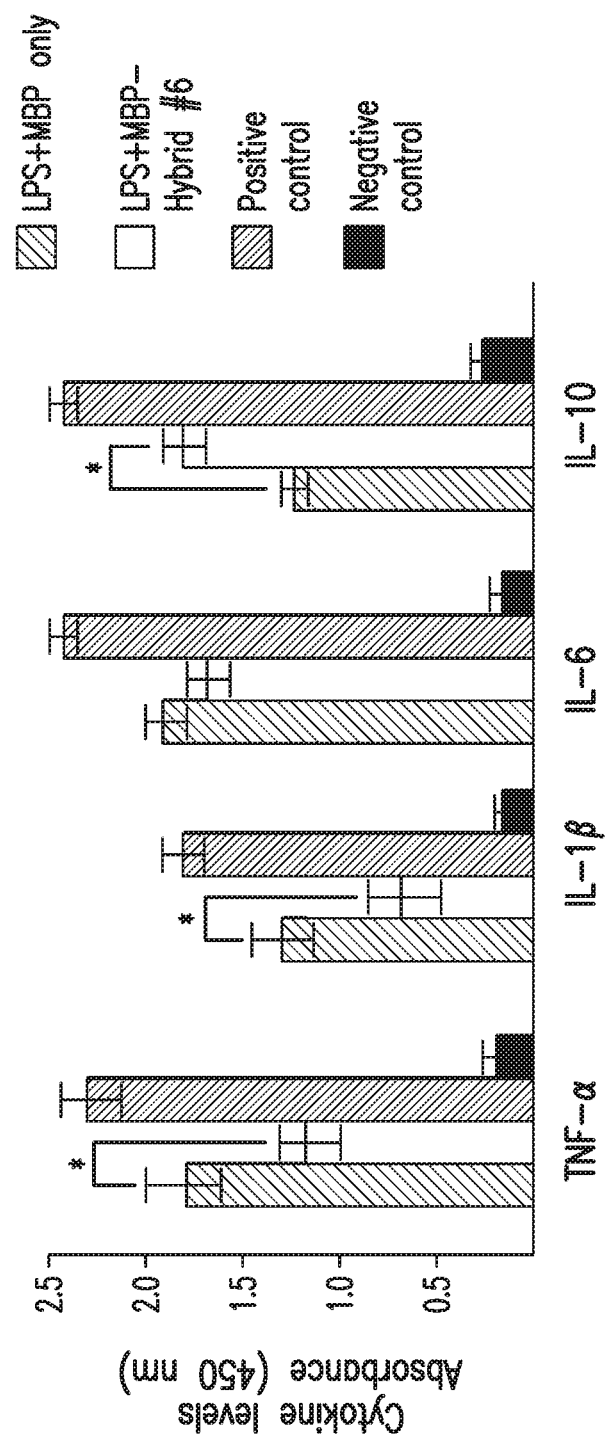
FIG. 9 is a graph showing reduction in production of pro-inflammatory cytokines in BV2 microglial cells treated with 50 nm Hybrid #6. Cytokine levels were assayed by ELISA 24 hours post-LPS stimulation. Positive and negative controls were provided by QIAGEN. *p<0.05.

BV2 microglia were treated with LPS (1 µg/ml) to induce a pro-inflammatory environment in the presence or absence of Hybrid Protein #6 and determined the release of nitric oxide by the formation and accumulation of its stable metabolic product, nitrite, using the Griess test. The result indicates that nitrite accumulation (thus nitric oxide production) is reduced in LPS-treated BV2 cells supplemented with 10-200 nM hybrid protein (FIG. 7). A marked reduction in nitrite was obtained at 50-200 nM with the highest reduction at 50 nM. Moreover, the addition of 50 nM hybrid protein significantly reduced the production of pro-inflammatory mediators such as TNF-α and IL-1β while enhancing production of anti-inflammatory IL-10 (FIG. 8). These experiments can be repeated in the presence or absence of oligomers or fibrils, to determine whether the hybrid protein can reduce nitric oxide production and inflammatory mediators during phagocytosis. Whether the hybrid proteins can prevent Aβ-induced pro-inflammatory responses can be tested by analyzing NF-κB activation and by determining the levels of other pro- and anti-inflammatory cytokines in treated vs. control cells.

The production of reactive oxygen species (ROS) can be further examined as a function of superoxide dismutase (SOD) in the cell. SODs are metalloenzymes that catalyze the dismutation of the superoxide radical into hydrogen peroxide and molecular oxygen, providing an important defense against oxidative damage. ROS can be measured following the modified method of Pan et al. Briefly, NBT (nitroblue tetrazolium) can be added to the media at specific times after commencement of phagocytosis. As negative controls, BV2 or primary microglial cells can be pretreated with NAC (N-acety 1-L-cysteine, a free radical exchanger) one hour prior to oligomeric or fibrillar Aβ treatment. As a positive control, BV2 or primary microglial cells can be treated with t-BHP (tert-butyl-hydroperoxide, a strong oxidant) for 60 minutes. The cells can be further incubated for 45 minutes at 37° C., washed with warm PBS and then methanol, and then air-dried. The NBT deposited inside the cells can be dissolved with KOH and DMSO with gentle shaking and the dissolved NBT solution can be transferred to a 96-well plate and the absorbance read on a microplate reader.

ii. Cell Viability

Cell viability can be determined by 2,5-diphenyl tetrazolium bromide (MTT) assay. In living cells, MTT is converted into purple-colored formazan, which has a specific absorption maximum at 570 nm. When cells die, they lose the ability to convert MTT into formazan; thus, color formation serves as a useful and convenient marker of only the viable cells. The quantity of formazan should be directly proportional to the number of viable cells. Cells can be treated with Aβ and the medium changed at specific times after phagocytosis commences. The cells can be further incubated for 4 hours after the culture medium is changed to one containing MTT. Then, solubilization solution can be added and cells can be incubated at 37° C. in humidified chamber for overnight. The absorbance of the supernatant can be measured at 570 nm. Data can be expressed as the mean percentage of viable cell in treated versus untreated control.

iii. Intracellular Clearance of Aβ.

Intracellular Aβ clearance over a time course can be determined. Briefly, BV2 or primary mouse microglia can be incubated with Aβ oligomers or fibrils in serum-free DMEM-F12 in the presence of hybrid proteins or a control protein. Intracellular Aβ peptide levels can be determined at different intervals post phagocytosis initiation by ELISA following lysis of the cells in SDS and normalized to total protein. To complement this lysis strategy, live confocal time-lapse imaging of cells fed with fluorescently labeled AP oligomers or fibrils can be conducted to determine Aβ clearance in the phagosome. Fluorescence intensity corresponding to the ingested Aβ can be quantified over the course of the experiment.

iv. Data Analysis.

All data can be analyzed by Student's t-test. Data for multiple groups can be analyzed by one-way ANOVA Post-hoc test using IBM SPSS Software.

2. Results

The following can occur: (a) The hybrid proteins can reduce the levels of pro-inflammatory factors and stimulate the production of anti-inflammatory factors, reduce NO and ROS levels, and increase production of SOD and CAT. (b) Cell viability and clearance of Aβ can be enhanced.

D. Example 4: Hybrid Proteins can be Deployed to Remove and Prevent Aβ Accumulation in the APP/PS1 Mouse Model of Alzheimer's Disease One of the key characteristics of AD is the buildup of Aβ protein aggregates or clumps and the formation of Aβ plaques in the brain, accompanied by inflammation. The hybrid protein can facilitate clearance of Aβ in the brain and reduce inflammation that can consequently result in improvements to learning and memory in a mouse model of AD. The primary outcomes can be the efficient clearance and prevention of the accumulation of Aβ and reduction in inflammatory and oxidative markers in the brain. The secondary outcomes include improvements in learning and memory in a mouse model of AD.

Clearance of Aβ in vivo can be determined by histopathologic examination and immunohistochemical studies of the brain. Inflammatory and oxidative responses can be determined by measuring the expression levels of IL-1β, IL-6, and TNF-α and some anti-inflammatory factors and oxidative markers such as INOS, SOD and CAT, using real-time RT-PCR. Behavioral studies can be conducted to assess any improvements in learning and memory in AD mice.

Figure 11:
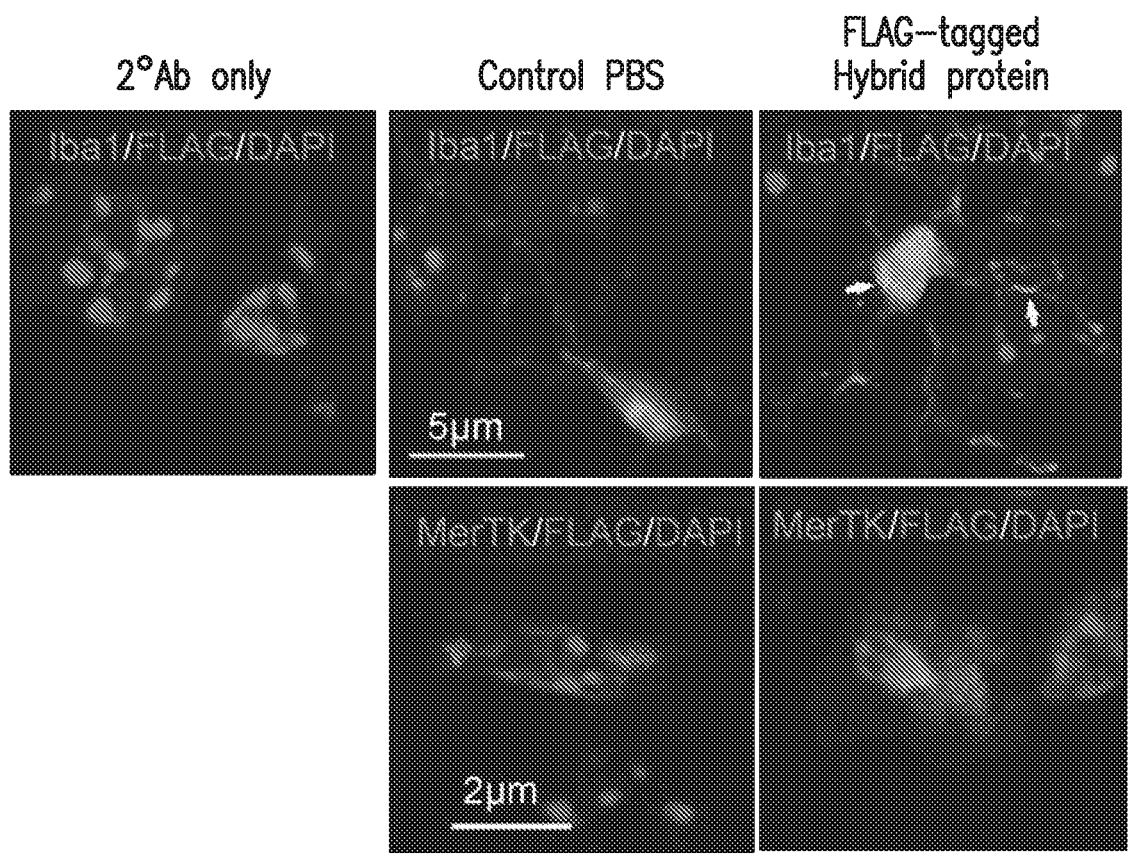
FIG. 11 shows Hybrid #6 crosses the blood brain barrier. Immunohistolocalization of FLAG-tagged Hybrid 6 in the brain of mouse injected intra-peritoneally (IP) with 50 mg/kg BW protein after 30 min of IP. Brain sections were stained with α-Iba1 (microglia) or α-MerTK and Alexafluor 488 a-rabbit Abs (Invitrogen; green). FLAG-tagged hybrid was stained with mouse α-FLAG mAb and Alexa-fluor 568 α-mouse 2° Abs (Invitrogen; red). Colocalization of the hybrid proteins after 30 minutes of IP injection showed that the hybrid (FLAG-labeled: red) is taken up by the microglia (Iba1-labeled; green) in the brain (shown in yellow). Consistent with our hypothesis that the hybrid will direct clearance through MerTK, our co-localization studies also confirmed that the hybrid protein co-localizes with the MerTK receptor (lower panel).

In order to address the question of whether or not the chimeric protein can cross the blood-brain barrier, 50 mg/kg of Hybrid #6 was administered by intraperitoneal injection in wild-type C57BL/6J mice. The chimeric protein has been FLAG-tagged at the N-terminal. The fusion protein was purified and the protein cleaved from MBP to generate the pure FLAG-Hybrid Protein #6. Thirty minutes and one hour after injection, the brain and other organs were harvested for immunohistochemistry. The result shows that after 30 minutes of IP injection the hybrid (FLAG-labeled: red) is taken up and colocalizes with the microglia (Iba1-labeled; green) in the brain (shown in yellow). Consistent with our hypothesis that the hybrid will direct clearance through MerTK, our co-localization studies also confirmed that the hybrid protein co-localizes with the MerTK receptor (FIG. 11, lower panel).

Intraperitoneal injection is the most commonly used route in small laboratory animals, as it is difficult to trace the vein of small animals (vs. intravenous). It is most useful for substances that are easily degraded in the gastrointestinal tract and insufficiently absorbed. However, other routes, such as subcutaneous or intracranial can be used to eliminate the uncertainty of systemic pharmacokinetic variables.

1. Experimental Design
  i. Animal Model of AD.

APP/PS1 mice (APPswe, PS1dE9) can be purchased from Jackson Laboratory (Bar Harbor, Me.) and housed under standard conditions with a 12-hour light/dark cycle at room temperature (22° C.). APP/PS1 is one of the most widely used AD models. This double transgenic expresses a chimeric mouse/human amyloid precursor protein (Mo/HuAPP695swe) and a mutant human presenilin 1 (PS1-dE9), both of which are controlled by independent mouse prion promoter elements, with both proteins directed to CNS neurons. Both mutations are associated with early-onset Alzheimer's disease. The mice exhibit sparse Aβ deposits as early as 6 months and abundant plaques in the hippocampus and cortex by 9 months of age, with occasional deposits as young as 6 months old. Senile plaques are detectable by thioflavin S or anti-amyloid antibody as early as 4 months old, with plaques restricted to the cortex and hippocampus at intervals up to 1 year old. This model exhibits progressive increase in cerebral amyloid angiopathy as early as 6 months and an overall increase in soluble and insoluble Aβ40 and Aβ42 between 4 and 12 months. These animals also present progressive learning and memory deficits.

ii. Choosing the Age/Stage of Mice to Administer the Treatment.

Figure 10:
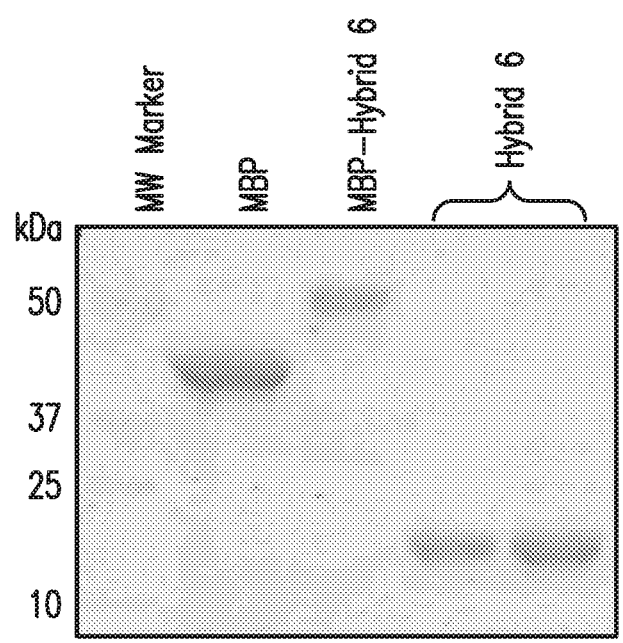
FIG. 10 shows purification of FLAG-Hybrid #6. Hybrid #6 was expressed as MBP-fusion protein engineered with a 3C-protease cleavage site between the MBP and the FLAG tag. After 3C digestion, the solution was run through a maltose resin and an α-FLAG resin, then eluted with FLAG peptides.
Figure 13A:
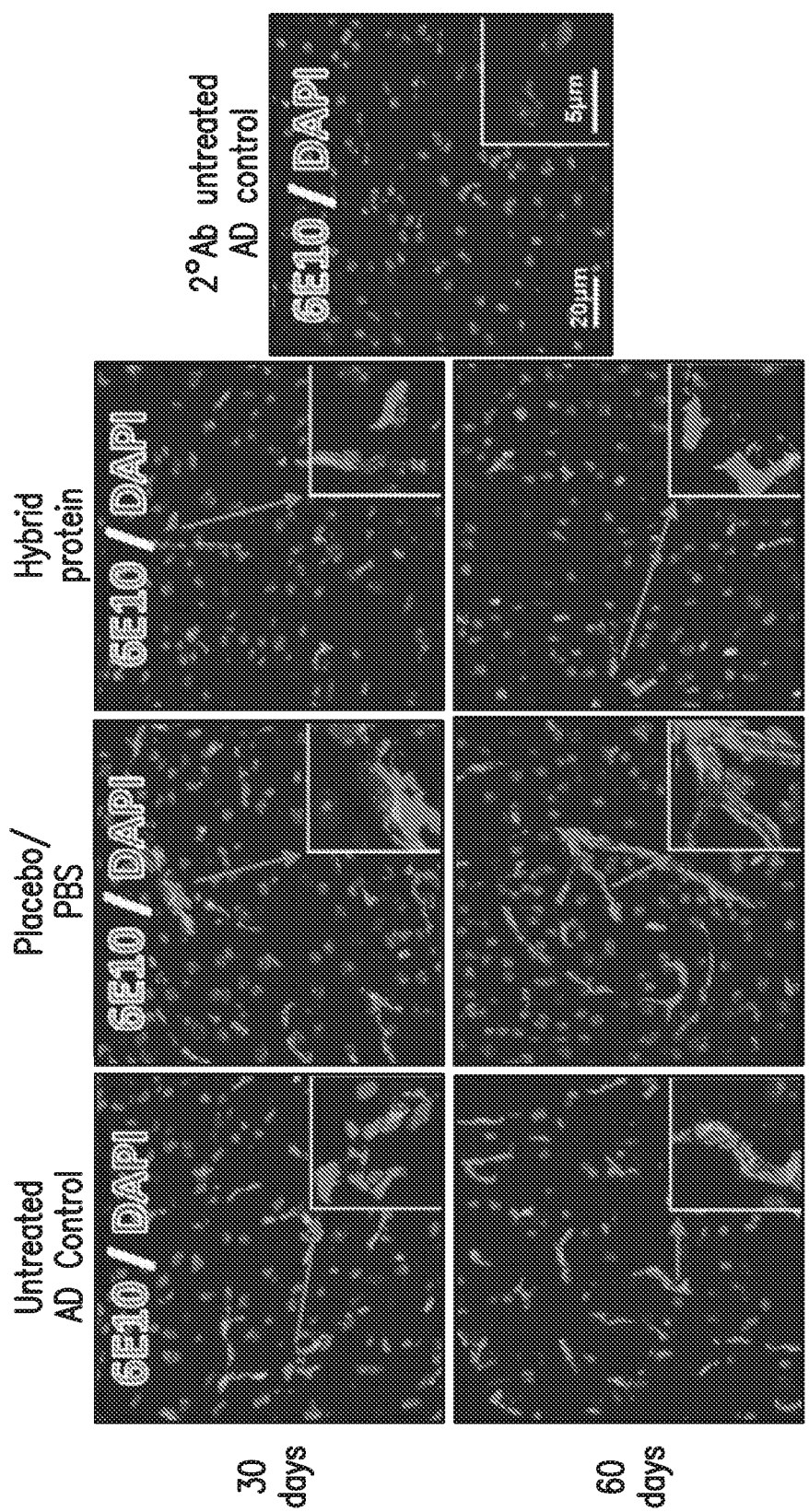
FIG. 13A shows that Hybrid protein significantly reduces Aβ burden in 3×Tg mice model of AD. Immunohistochemical (IHC) localization of Aβ in female mice. Males had a slightly delayed response (not shown). 2° Abs staining was included as a negative control.
Figures 13B, 13C:
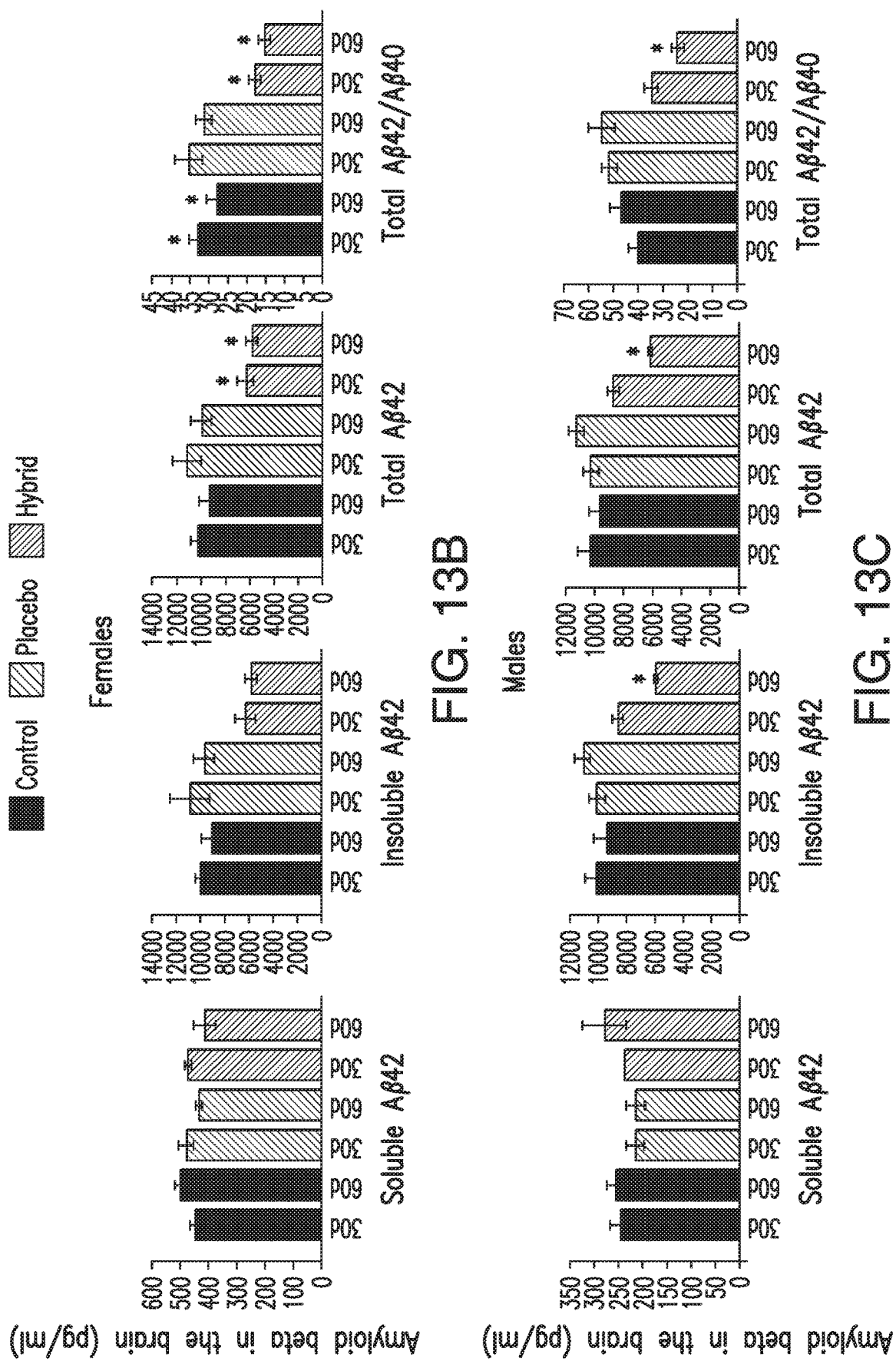
FIGS. 13B and 13C show the quantitative analysis of Aβ in brain lysates of female (B) and male (C) 3×Tg mice using a Millipore ELISA Kit (EZbrain42 and EZbrain40). Aβ40 levels are similar for all groups (not shown). Data are means+/−SD of 3 mice per treatment. **Significantly different at $P<0.05$. Control=age–matched AD untreated control. Placebo=PBS injected.

Treatment is commenced when APP/PS1 mice are 6 months of age. At this stage, the animals already exhibit sparse Aβ deposits and amyloid plaques with progressive increases in cerebral amyloid angiopathy and soluble and insoluble Aβ40 and Aβ42. Learning and memory deficits are also present by 6 months of age in this model. Since the treatment is based on the ability of the hybrid protein to direct the clearance of Aβ through the MerTK phagocytic pathway, the most efficient clearance can be obtained during the stage of early deposition of plaques beginning at 6 months, rather than the latter AD stages where plaque burden is high and neuronal damage is irreversible.

a. Preliminary Studies:

In order to determine if the hybrid protein can reduce Aβ burden in the brain of AD mice, the hybrid protein (FIG. 10) was purified and administered in 6-months old AD mice. Two treatment groups were considered: Placebo (vehicle-PBS) and hybrid at 50 mg/kg BW (=31.25 mg per 25 g mouse). To anticipate possible sex-specific differences in response to treatments, both male and female mice were used for each of the above treatments. Female mice (25.6-29.3 g BW) and male mice (30.1-35.9 g BW) were randomly assigned to the treatments. Intraperitoneal (IP) injection of the hybrid protein or PBS was done once daily for 60 days on alternating sides on progressive days of administration. At day 30 and day 60, 3 mice were sacrificed in each group. Sera were collected from the blood and analyzed for cytokine levels. Brain and other relevant tissues were either snap frozen in liquid nitrogen for biochemical analyses or processed for immunohistochemistry (IHC). For IHC to determine Aβ burden in the brain, the left hemisphere of the brain was sectioned at 7 uM thickness, where a series of 10 equally spaced tissue sections spanning the entire left hemisphere were selected and stained using mouse α-Aβ6E10 Abs (Biolegends; 1:1000 dilution) and Alexa fluor 488 2° Abs (Invitrogen). The region of the neocortex was manually selected for analysis of Aβ plaques. Specifically, images were collected first at 10×, then 5 random regions within the 10× were further magnified at 40×. Representative brain sections of treated and untreated mice are shown in FIG. 12A. Complementary to confocal analysis, Aβ in the brain homogenates were quantified using an ELISA kit (Millipore EZBRAIN-SET) specific for Aβ40 and Aβ42. The data by confocal microscopy and ELISA were consistent with each other showing a significant reduction in the Aβ burden of mice treated with the hybrid protein compared to control untreated and vehicle/placebo (PBS) treated mice. There were slight differences in the response to treatment between males and females. After 1 month, female mice that received the hybrid protein had a significant reduction (~45%) in their Aβ load in the brain. This response is maintained even after 2 months of treatment. In contrast, males did not show a significant compared to the controls at 1 month. However, at 2 months of treatment the males had 60-65% reduction of Aβ load compared to controls. It appears that males had a delayed response to treatment than females. Cytokine analysis of sera from female mice showed no increase for IL-1 or TNFα, a slight reduction in the levels of IL6, a slight increase in IL12 and IL17A at two months (FIG. 13A). IFNγ was barely detectable in all groups. In contrast, in males, a more remarkable reduction in levels of inflammatory factors such as IL6, IL12, IL17A, IFNγ and GM-CSF were observed after 2 months of treatment (FIG. 13B). The long-term implications of the changes in the levels of these cytokines in our preliminary data remains to be further investigated, taking into account that it only reflects the first two months of treatment. The interplay of these different cytokines in inflammation in response to the hybrid treatment can become more apparent or definitive as treatment progresses.

Moreover, colocalization of the hybrid proteins after 30 minutes of IP injection showed that the hybrid (FLAG-labeled: red) is taken up by the microglia (Iba1-labeled; green) in the brain (shown in yellow) (FIG. 11). Consistent with the hybrid directing clearance through MerTK, the co-localization studies also confirmed that the hybrid protein co-localizes with the MerTK receptor (FIG. 11, lower panel).

iii. Refinement of the Dosage for Optimum Protection by the Hybrid.

Figure 14A:
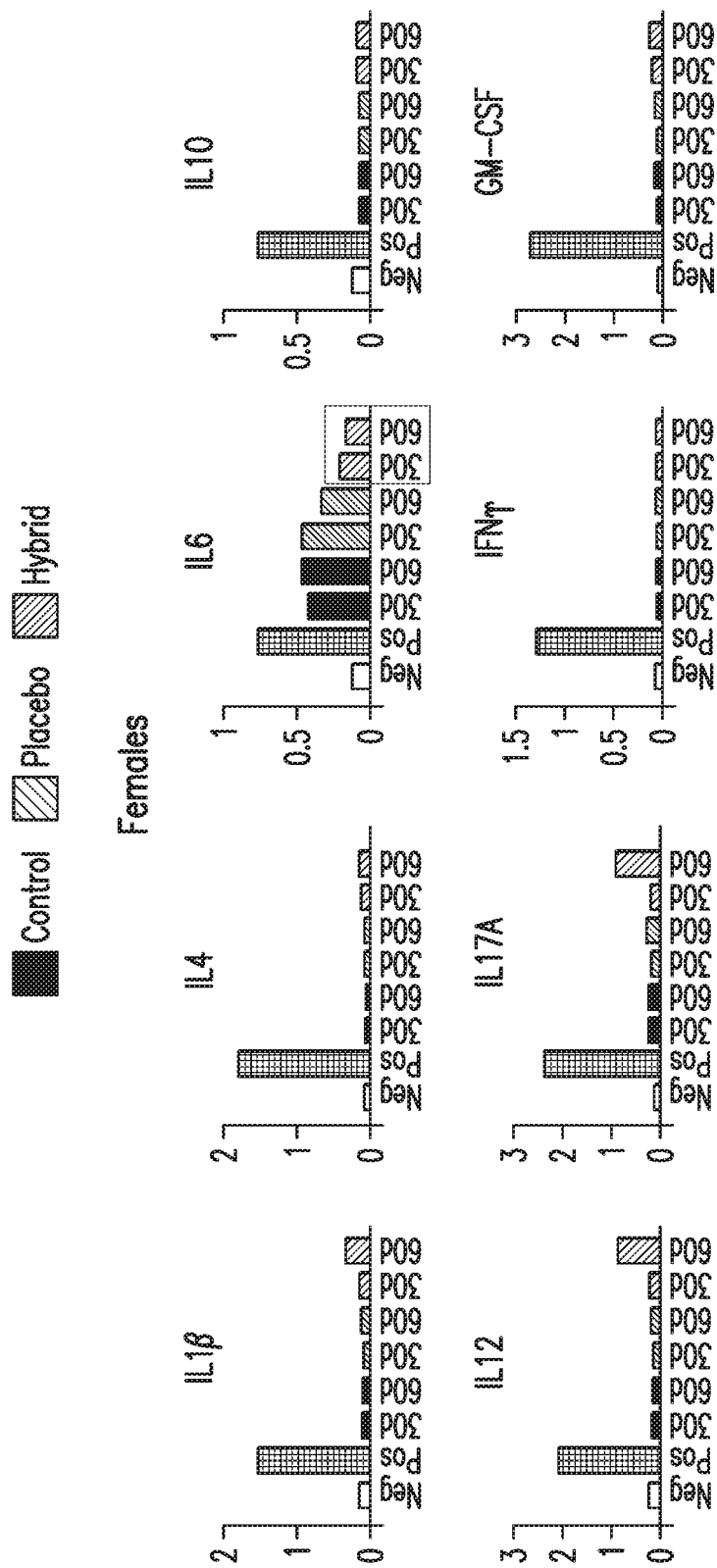
FIGS. 14A and 14B show the cytokine production in 3×Tg mice treated with the hybrid protein. Sera were collected from mice at 30 and 60 days after treatment. Cytokine levels were assayed using Multi-analyte ELISA array kit from Qiagen. Positive and negative controls for each cytokine were provided by the manufacturer. Control=age–matched AD untreated control. Placebo=PBS injected. Hybrid=hybrid injected.
Figure 14B:
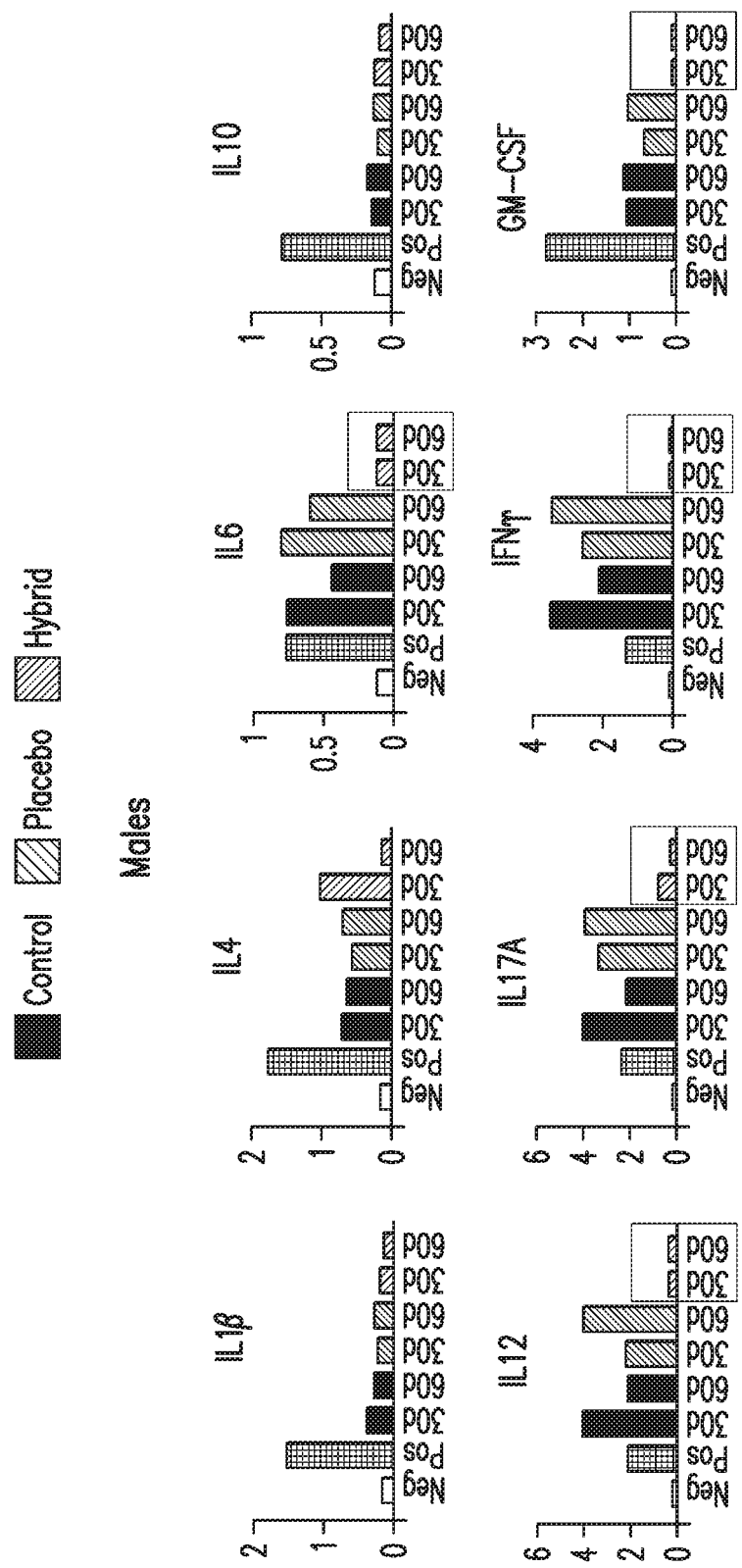
Figure 15:
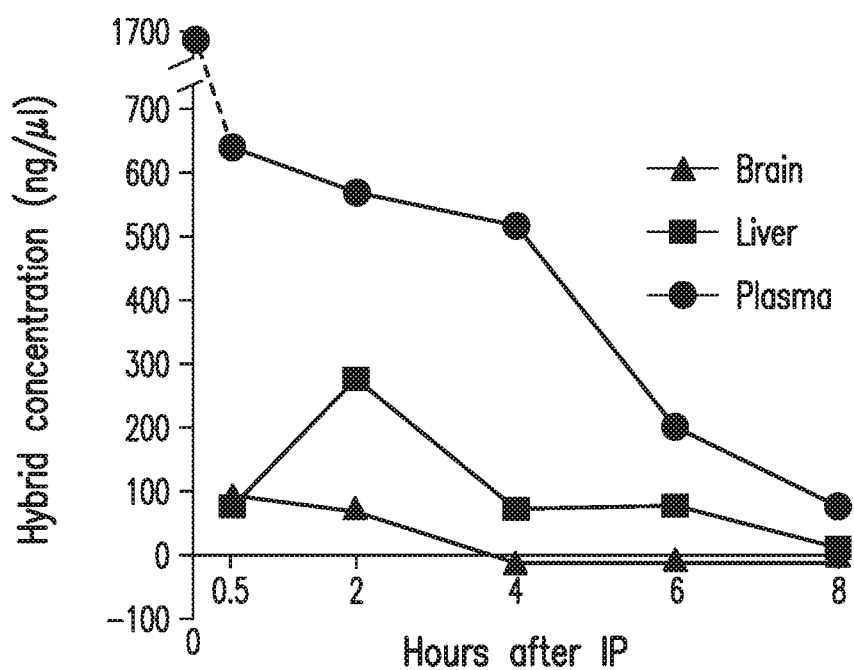
FIG. 15 shows the distribution/clearance of the hybrid peptide. Mice were dosed with 1250 μg hybrid peptide (equivalent 50 mg/kg BW). Blood and tissue samples were collected at indicated times after IP injection. Plasma or homogenized tissues were assayed for the level of hybrid peptide using ELISA with α-FLAG mAbs, then HRP-conjugated 2° Abs followed by colorimetric assay. Since we performed IP (which is equivalent to intravenous), we expect that the peptide went into systemic circulation right away and did not go through first pass metabolism in the liver. Thus we can assume that right after injection, the concentration in the blood would have been ~1712 ng/μl (1250 μg/0.73 ml=1712 μg/ml). After 30 minutes, the highest concentration we observed in the plasma was 642 ng/μl which accounts for ~37.5% of the input protein. At 8 hours, plasma peptide concentration was ~4%. Interestingly, brain concentration was highest at 30 minutes (~100 ng/μl) and persisted only until ~2 h after IP.

IP injection of 50 mg/kg gives a significant reduction (45-65%) in Aβ burden in the brain of AD mice. However, does this reduction results to neuroprotection and amelioration of memory deficits in mice? There is a need to refine the dosage to get an optimum result. It is important to note that over the course of two months treatment, no mortality was observed. Although the mice in all treatments lost an average of 10% of their weight during the first two weeks of injection, they gained weight thereafter. The initial weight loss could be attributed to handling stress. This might indicate that the hybrid is not chronically toxic to the mice. The other question is whether this dose can be immunogenic. The hybrid can cross the blood brain barrier (FIG. 11). When the distribution and clearance of the peptide was examined over a time course, a dose of 1250 μg in 25 g mouse (=50 mgs/kg BW) resulted to ~100 ng/μl of hybrid in the brain (FIG. 14). To make sure that sufficient peptide concentration is delivered in the brain, and to eliminate the uncertainty of systemic pharmacokinetic variables a direct intracranial delivery of the peptide using iPRECIO implantable pump (SMP-300 specifically for mice; iPRECIO, Durect Corp) can be used. The pump works based on miniature peristaltic action and can be implanted subcutaneously. Reservoir is also refillable via a percutaneously accessible port. Because the pump is programmable, it can deliver an accurate controlled flow at constant rate as low as 1 ul/hour (0.1-1 ul), and has been found to be more precise and consistent (as opposed to Alzet pumps).

iv. Pilot Study to Establish the Optimum Dose.

A positive response of almost 45% clearance of Aβ was observed in female mice as early as one month of treatment. And this is only based on ~100 ng of the hybrid that was able to cross the blood brain barrier. In this study, only females will be used and their response after one month determined. The reason for this is because females showed a faster positive response to treatment than males in just one month. Initially, five treatments can be done: Placebo (PBS only), 10 ng/day, 100 ng/day, 1 ug/day, and 10 ug/day. Each treatment can have five replicates and 6-month old mice can be randomly assigned to each treatment.

The animals can have individual weights within 20% of the mean weight. The iPRECIO pumps can be implanted on the mice and the flow rate of the hybrid can be programmed to give the specific dosage as indicated above. Other than the Aβ clearance in the brain, the following parameters and endpoints can be established: mortality, clinical signs, body weights, food consumption, hematology and serum biochemistry parameters, and post-mortem evaluation including gross examination for all the animals at the terminal necropsy. Evaluation of the above parameters and necropsy and peripheral tissue evaluations can be performed.

Evaluation of pharmacokinetics, pharmacodynamics, toxicity, and immunogenicity. The long-term goal of this project is to qualify for a clinical trial to test the hybrid protein in humans diagnosed with AD. For effective therapeutic management of the drugs in patients, controlled animal studies will be done first to make sure that the hybrid protein is safe at high multiples of expected human trial dosages. Thus, toxicity, the toxicokinetic time course of drug absorption, distribution, metabolism and excretion, including immunogenicity of the hybrid will have to be established in mice.

v. Peptide Pharmacokinetics and Pharmacodynamics:

Mice were dosed with the hybrid peptides at 50 mgs/kg BW (=1250 μg for 25 g mice). Blood and tissue samples were collected at 30 min, 2, 4, 6 and 8 hours after IP injection. Plasma or homogenized tissues were assayed for the level of hybrid peptide using ELISA with α-FLAG mAbs, then HRP-conjugated 2° Abs followed by colorimetric assay (FIG. 14). Mice have ~58.5 ml of blood/kg BW. A 25 g mouse has ~1.46 ml blood and ~0.73 ml of which is plasma (50%). Since IP (which is equivalent to intravenous) was performed, it is expected that the peptide went into systemic circulation right away and did not go through first pass metabolism in the liver. Thus right after injection, the concentration in the blood would have been ~1712 ng/μl (1250 μg/0.73 ml=1712 μg/ml). After 30 minutes, the highest concentration observed in the plasma was 642 ng/μl which accounts for ~37.5% of the input protein. At 8 hours, plasma peptide concentration was ~4%. Interestingly, brain concentration was highest at 30 minutes (~100 ng/μl) and persisted only until ~2 h. ELISA may not be the most suitable technique to quantify the rate of clearance for the hybrid. For a more accurate quantification of peptide clearance, radioactive labeling of the hybrid proteins can be employed. Briefly, hybrid proteins can be labeled with 125-Iodine. $^{125}$Iodine is commonly used for labeling proteins, usually at Tyrosine residues. Once the optimum dose has been established, the hybrids can be labeled with $^{125}$I and infused into the brain of mice. Blood can be drawn at 15 min, 30 min, 1, 2, 4, 6, 12, 18 and 24 hours post infusion. After the bloods are drawn, mice can be sacrificed and tissues (brain, liver, and other major tissues/organs that are involved in clearance) can be processed for quantitative analysis of labeled hybrids. Specifically, tissues can be homogenized and aliquots can be subjected to a liquid scintillation assay (LSA). Complementary to LSA, semi-quantitative analysis can be done by running the different sample lysates on a gel and placed on a phosphor screen that can be subsequently imaged in a phosphorimager. Based on the distribution of total radioactivity, the sum total of the parent compound and/or labeled metabolites in the different tissues or plasma can be determined. In addition to serum and tissues, CSF sampling can be done to determine free peptide concentration in the brain. CSF concentrations have been shown to correlate with both brain interstitial concentrations and behavioral changes. For each sampling time point above, 3 replicate mice can be used for analysis and experiments can be repeated 3 times to ensure reproducibility of results.

vi. Long-Term Treatment to Determine Aβ Clearance, Neuroprotection and Amelioration of Memory Deficits by Behavioral Tests and Histopathological Endpoints in APP/PS1 Model of AD After the optimum range of dose is established, the next step can be to repeat the experiments using the two doses that showed the most promising effects. This time, larger replications can be needed to accommodate the cognitive/behavioral tests and histopathological analyses (at least 10 per group). Another consideration is to extend the treatment up to 6 months (see FIG. 12).

Treatments can be done in males and females to account for any sex-specific effects over the long-term. Animals that can be used should be within 20% of the mean body weights. Animals can be randomly assigned to either placebo or treatment groups. To ensure reproducibility of the results, hybrid peptides can be produced in large quantities, combined, aliquoted and frozen so that each mouse can receive the same mix/batch of the peptides. To check the activity of the peptides after thawing, circular dichroism (CD) can be used to measure absorption of the peptides as the CD phenomenon is exhibited in absorption bands of any optically active biological molecules because of their dextrorotary and levorotary components. Even more important is that a secondary structure can also impart a distinct CD to its respective molecules, hence active peptides can have a distinct CD profile. To avoid bias during analyses, blood and tissue samples can be assigned a barcode during collection. Research participants who can be responsible for analyses can be blinded with the treatment and can only be supplied with a barcode. The master code sheet can be secured.

a. Cognitive/Behavioral Analysis.

There is strong evidence that the cognitive and behavioral deficits characteristic of AD arose from impaired synaptic function. It can be determined whether treatment with the hybrid protein can ameliorate learning and memory deficits and improve hippocampal function in the APP/PS1 mice.

Behavioral testing can consist of two distinct behavioral tasks: (1) novel object recognition (NOR) and; (2) the Morris water maze (MWM). Based on previous investigations, no carryover effect has been observed when running animals in more than one task; furthermore, each task examines distinct behaviors and has not been demonstrated to alter the results of the other. Therefore, all cohorts can be run in both tasks in an effort to minimize the number of animals needed for the proposed studies. The detailed procedures for each task are provided in the vertebrate animal section of this grant. MWM is a well-established spatial learning and memory task in which several AD model systems exhibit learning and memory deficits. In addition, the non-spatial visual component serves as a good control to ensure any deficits are not associated with visual or motor impairments. Spatial learning and memory can be assessed in the Morris water task. Mice can be evaluated for their ability to initially learn the location of a hidden platform (latency and path length), as well as evaluated in a probe trial to assess the accuracy of spatial learning. A novel object recognition test (NOR) can also be performed. A highly validated test for recognition and memory that's complementary to the MWM, this test consists of two stages: the training, and the test stages. The basic idea is to expose the mouse to two or more objects and allow it to explore them for a while during the training stage. Then, at the test stage, one of the objects is replaced by a different one. If its memory functions normally, the mouse spends more time exploring the novel object than the familiar one. If the time spent exploring both objects is equal, this can be interpreted as a memory deficit. Both NOR stages can be recorded by a tracking system (Smart, San Diego Instruments, San Diego, Calif.) and the obtained data can include total time spent investigating objects and novel object preference. Multiple observers can also manually score the object investigation time in order to ensure accurate data. Object investigation can be defined as direct contact with the object or sniffing of the object within 2 cm of the animal's head. For both MWM and NOR, observers can be blinded to the treatments to minimize any recording bias. Similarly, the biostatistician analyzing the data can also be blinded to treatments to minimize bias in result interpretation.

b. Histopathologic, Immunohistochemical, and Inflammatory Responses.

Following behavioral analyses, mice can be sacrificed from each group and relevant tissues harvested for histopathologic, immunohistochemical, and inflammatory studies. Amyloid plaque staining of the brain can be performed and detected with the monoclonal antibody against human Aβ42 (6E10, BioLegend), which recognizes amino acids 1-16 of human Aβ42. Parallel to immunohistochemical studies, H&E staining can be done to detect for shrinkage, necrosis, or hyperchromatic nuclei in the brain. In addition, brain samples can be processed for western blotting to detect levels of oligomeric Aβ. Complementary to immunohistochemical and H&E studies, classic approaches to detect Aβ can also be undertaken by staining with Congo red or Thioflavin S. Congo red can stain very small Aβ spots while Thioflavin S labels both neuritic plaques (but not diffuse type) and tangles or threads which may be helpful in detecting neuronal loss. In all cases, plaque burdens/stained plaques can be counted on at least 5 fields throughout the entire hippocampus and cortex and subjected to statistical analysis.

Vision disturbances have been reported in early-stage AD, long before diagnosis is clearly established. Thus, changes in Aβ ocular load can be examined using histology and immunohistochemistry in parallel with the brain studies.

Whether the hybrid protein can alleviate inflammation and enhance antioxidation activity in the CNS of AD mice can be determined. Expression levels of iNOS, IL-1β, IL-6, and TNF-α and some anti-inflammatory factors (IL-10) can be measured using real time RT-PCR. The expression of SOD and CAT can be determined to evaluate the oxidative activity in the brain. Furthermore, GFAP, a specific biomarker of activated astrocytes whose activation is usually accompanied by inflammation, can be determined. Microglial activation can be analyzed by staining for Iba1-positive microglia and CD68 in the mouse brains. High levels of CD68 expression are associated with activated microglia; low levels with quiescent ramified microglia.

vii. Sample Size and Statistical Analysis Plan.

A minimum of 10 mice per group/treatment is required to obtain sufficient power to observe significant differences in treatment response. In addition, 10 animals per group are necessary to allow for the tissue work outlined above. Thus, for behavioral studies, 10 mice can be utilized for each group (APP/PS1 treated, APP/PS1 untreated, and wild-type untreated for each gender) for each of the two intervals. The statistical analysis can include two-way (genotype×treatment) repeated measures analysis of variance with Tukey post-hoc comparisons for MWM latency, distance, speed of swimming, and perimeter time. Two-way ANOVAs can be performed for the probe trial and all other behavioral data with Tukey post-hoc comparisons. Similar, two-way ANOVAs and t-tests can be performed in the analyses of NOR and AD pathological features and inflammatory markers. Redcap can be used for data management.

2. Results

At the conclusion of these experiments, a therapeutic strategy for phagocytic clearance of Aβ in a mouse model of AD. Specifically, treatment of hybrid proteins can prevent plaque accumulation in mice or reduce plaque burden in treated animals. There can be improvement in cognitive and behavioral functions. At the cellular level, reduction of inflammatory and oxidative activity is expected. This project defines the first protein-guided phagocytosis-based therapy as a novel strategy for the clearance of deleterious metabolic products such as Aβ.

E. Example 5: Chimeric Protein-Guided Phagocytic Removal of Aβ Aggregates Thru MerTK Engagement of RAGE with Aβ aggregates or fibrils causes activation of a cellular cascade that results to nuclear translocation of NF-kB and sustained release of pro-inflammatory cytokines that eventually leads to cell death. In a mouse model of Alzheimer's disease, administration of the soluble RAGE (sRAGE) has been shown to reduce development of cerebral amyloidosis. In other animal models, recombinant sRAGE has been shown to reduce inflammatory responses in collagen-type-II-induced arthritis, delayed-type hypersensitivity, experimental autoimmune encephalomyelitis, and diabetic atherosclerosis. Taken together, these data indicate that sRAGE can act as a decoy to prevent interaction of Aβ with cell surface RAGE, thus blocking the activation of a neurotoxic cascade.

Exploiting the above principle, a 36 amino acid consensus sequence has been generated that has been optimized to have higher binding affinity to Aβ. This is an AP binding protein (AβBP). Combined with previous work on Tubby and Tulp1, the first protein-guided phagocytosis-based therapy for the removal of deleterious metabolic products by combining the Aβ binding protein with Tubby or Tulp1 N-terminals was designed. TubbyN-AβBP or Tulp1 N-AβBP chimera can hijack Aβ aggregates towards anti-inflammatory MerTK. Data shows that Tulp1 N-AβBP binds and facilitates phagocytosis of Aβ fibrils in BV2 cells (FIG. 11). In this project, the ability of Tulp1 N-AβBP, TubbyN-AβBP, Gas6-AβBP, MFG-E8-AβBP (Gas6 and MFG-E8 are other known phagocytosis binding proteins for MerTK) and Tulp3-AβBP (Tulp3 protein is a member of the Tubby family that does not bind to MerTK), can be compared in facilitating phagocytosis of fluorescently labeled Aβ aggregates in both BV2 and primary microglia.

Activation of MerTK triggers an intracellular signaling cascade that induces cytoskeletal rearrangement and uptake of the cells/cellular debris and their colocalization with the phagosomes. Colocalization of phagocytosed Aβ can be analyzed with biomarkers specific for MerTK activation and downstream signaling. To determine MerTK dependence, phagocytosis can be performed in the presence or absence of excess Mer-Fc (Mer extracellular domain fused to IgG1).

F. Example 6: Chimeric Protein-Guided Phagocytosis and Inflammatory Mediators Aβ accumulation elicits an acute microglial response through two signaling pathways: NF-κB and ERK-2/AP. These pathways converge at the transcriptional level to induce expression of pro-inflammatory cytokines such as IL-1(3, IL-6 and tumor necrosis factor alpha (TNF-α). NF-κB is an important upstream modulator of pro-inflammatory cytokines and iNOS (inducible Nitric Oxide Synthase) expression. Both pro-inflammatory cytokines and oxidative damage are observed early in the progression of AD and can be detected prior to fibrillar Aβ deposition in the AD brain. Microglial activation can also be detected in vivo in around half of patients with mild cognitive impairment.

To analyze whether internalized Aβ are degraded and cleared, live confocal imaging of cells fed with fluorescently labeled Aβ aggregates can be done. Fluorescence intensity corresponding to the ingested Aβ can be quantified over a time course. In parallel, immunocytochemical detection of Aβ inside the microglial cells can be done using antibody against Aβ. Alternatively, biotin or radioactive labeling of Aβ can be made and biotin or radioactive signals can be quantified over a time course to determine degradation of internalized Aβ.

G. Example 7: A Protein-Guided Phagocytosis Strategy to Clear Amyloid Beta Aggregates for the Treatment of Alzheimer's Disease Alzheimer's disease (AD) is a progressive neurodegenerative disorder that is characterized by impairment in memory, complex cognition, language, and visual/spatial skills. The exact cause for Alzheimer's is poorly understood and currently there is no cure. One of the hallmarks of AD is the accumulation/aggregation of Amyloid beta (Aβ) proteins in the brain of patients with Alzheimer's disease. Aβ proteins are normally removed by specialized cells in the brain called microglia. However, the removal of these aggregates leads to activation of the inflammatory pathway via RAGE-signaling that eventually results to death of the brain cells.

The Tubby protein was recently identified as a ligand that mediates phagocytosis (engulfment of cellular debris) through MerTK, a receptor whose activation is known to not cause an inflammatory response.

Aβ can be removed in a less deleterious manner by diverting its clearance to a non-inflammatory pathway. This strategy involves creating a hybrid protein by linking Tubby to the consensus Aβ binding peptide (cAβBP) that has been generated. Tubby can activate MerTK while cAβBP can bind Aβ. The TubbyN-cAβBP hybrid can act as a decoy to divert clearance of Aβ proteins to MerTK non-inflammatory phagocytosis instead of the inflammatory RAGE pathway.

The AβBP consensus binds to different forms (oligomers, fibrils) of Aβ at a slightly lower efficiency compared to RAGE.

H. Example 8: Generation of High Affinity Amyloid Beta Binding Peptides (AβBPs) by In-Vitro Protein Evolution (IVE) and Phage Display for Treatment of Alzheimer's Disease The Tubby protein has been identified as a ligand that facilitates eating and degradation of cellular debris through MerTK, a receptor whose activation is known to not cause an inflammatory response. A new therapy to prevent the build-up of Aβ in Alzheimer's disease is being developed. One step towards this therapy is the development of peptides that have high binding affinity towards Aβ. For this study, PCR mutagenesis and phage display selection was performed to screen for peptides with high binding to Aβ. The peptides were then fused to TubbyN-terminal to create hybrids. The way the hybrid works is that the AβBP part sequesters Aβ and the TubbyN part activates MerTK to facilitate removal of Aβ. The hybrid proteins can "snatch" harmful Aβ and "re-channel" them to an alternative degradation route that does not instigate a toxic response (FIG. 1).

Mutant-AβBPs have been generated that bind to different forms of Aβ (oligomers, fibrils) with varying binding efficiencies.

Sequencing of mutant-AβBPs confirmed the presence of mutations resulting in changes to the amino acid residues.

A hybrid protein (Hybrid #6) was engineered that facilitated uptake of AP oligomers.

I. Example 9

TubN-AβBP hybrid was purified from *E. coli* and intraperitoneal injection of the hybrid protein was performed in 6-months old 3×Tg Alzheimer's disease mice at a dose of 50 mg/kg body weight. The injection was done once daily for 60 days. Three mice per group were sacrificed at day 30 and day 60. Sera were collected from the blood and analyzed for cytokine levels. Brain and other relevant tissues were either snap frozen in liquid nitrogen for biochemical analyses or processed for immunohistochemistry (IHC). For IHC to determine Aβ burden in the brain, the left hemisphere of the brain was sectioned at 7 uM thickness, where a series of 10 equally spaced tissue sections spanning the entire left hemisphere were selected and stained using mouse α-Ab 6E10 Abs (Biolegends; 1:1000 dilution) and Alexa fluor 488 2° Abs (Invitrogen). The region of the neocortex was manually selected for analysis of Aβ plaques. Complementary to confocal IHC, Aβ in the brain homogenates were quantified using an ELISA kit (Millipore EZBRAIN42 and EZBRAIN 40). The data showed a significant reduction in the Aβ burden of mice treated with the hybrid protein compared to control untreated and vehicle (PBS) treated mice (FIG. 12A). There were slight differences in the response to treatment between males and females. Specifically, there was no difference in the soluble Aβ42 in the brain of female mice regardless of treatments. However, the insoluble form was significantly reduced (~45%) in mice treated with 50 mg/kg hybrid at one month of treatment. This trend persisted even after two months of treatment. Total Aβ40 levels were not different in treated and untreated groups. Similar to females, soluble Aβ in the brain of male mice were similar regardless of treatments. Aβ burden was slightly lower (75%) but not statistically significant compared to the controls after one month. However, at 2 months of treatment the males had 60-65% reduction of Aβ load compared to controls. Males showed a delayed response to treatment when compared females.

Cytokine analysis (FIGS. 12B and 12C) of sera showed relatively low levels of inflammatory cytokines in both treated and untreated groups for female mice. The results showed a large reduction (~two-fold) in inflammatory IL6 in hybrid treated compared to untreated controls. In contrast, the levels of IL4, IL6, IL12, IL17A, IFN and GM-CSF were elevated in control untreated or vehicle treated male mice. These cytokines were significantly lower in hybrid treated mice as early as one month of treatment, except for IL4 that was observed to be elevated after one month but the level decreased after two months of treatment.

The significant reduction in the total Aβ burden in the brain and the reduction in inflammatory cytokine production in mice treated with the hybrid protein demonstrates the therapeutic potential of the TubN-AβBP hybrid protein.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Palop, J. J. and L. Mucke, Amyloid-beta-induced neuronal dysfunction in Alzheimer's disease: from synapses toward neural networks. Nat. Neurosci., 2010. 13(7): p. 812-8.
2. Sastre, M., J. Walter, and S. M. Gentleman, Interactions between APP secretases and inflammatory mediators. J Neuroinflammation, 2008. 5: p. 25.
3. Caberoy, N. B., Y. Zhou, and W. Li, Tubby and tubby-like protein 1 are new MerTK ligands for phagocytosis. EMBO J., 2010. 29(23): p. 3898-910.
4. Caberoy, N. B. Maiguel, D. Kim, Y., Li, W. Identification of tubby and tubby-like protein 1 as eat-me signals by phage display. Exp Cell Res, 2010. 316(2): p. 245-57.
5. Caberoy, N. B. Zhou, Y. Jiang, X. Alvarado, G. Li, W. Efficient identification of tubby-binding proteins by an improved system of T7 phage display. J. Mol. Recognit., 2010. 23(1): p. 74-83.
6. Caberoy, N. B., G. Alvarado, and W. Li, Tubby regulates microglial phagocytosis through MerTK. J. Neuroimmunol., 2012. 252(1-2): p. 40-8.
7. Caberoy, N. B., Synergistic interaction of tubby and tubby-like protein 1 (tulp1). Adv. Exp. Med. Biol., 2014. 801: p. 503-9.
8. Henson, P. M. and D. A. Hume, Apoptotic cell removal in development and tissue homeostasis. Trends Immunol., 2006. 27(5): p. 244-50.
9. Hochreiter-Hufford, A. and K. S. Ravichandran, Clearing the dead: apoptotic cell sensing, recognition, engulfment, and digestion. Cold Spring Harb Perspect Biol., 2013. 5(1): p. a008748.
10. Ravichandran, K. S. and U. Lorenz, Engulfment of apoptotic cells: signals for a good meal. Nat. Rev. Immunol., 2007. 7(12): p. 964-74.
11. Alzheimer's, A., 2011 Alzheimer's disease facts and figures. Alzheimers Dement, 2011. 7(2): p. 208-44.
12. Hong-Qi, Y., S. Zhi-Kun, and C. Sheng-Di, Current advances in the treatment of Alzheimer's disease: focused on considerations targeting Abeta and tau. Transl Neurodegener., 2012. 1(1): p. 21.
13. Ubhi, K. and E. Masliah, Alzheimer's disease: recent advances and future perspectives. J Alzheimers Dis., 2013. 33 Suppl. 1: p. S185-94.
14. Kumar, A., A. Singh, and Ekavali, A review on Alzheimer's disease pathophysiology and its management: an update. Pharmacol. Rep., 2015. 67(2): p. 195-203.
15. Mangialasche, F., Solomon, A., Winblad, B. Mecocci, P., Kivipelto, M. Alzheimer's disease: clinical trials and drug development. Lancet Neurol., 20100. 9(7): p. 702-16.
16. Lyck, L., Santamaria, I. D., Pakkenberg, B., Chemnitz, J., Schroder, H. D., Finsen, B., Gundersen, H. J. An empirical analysis of the precision of estimating the numbers of neurons and glia in human neocortex using a fractionator-design with sub-sampling. J. Neurosci. Methods, 2009. 182(2): p. 143-56.
17. Lee, C. Y. and G. E. Landreth, The role of microglia in amyloid clearance from the AD brain. J. Neural Transm., 2010. 117(8): p. 949-60.
18. Barile, G. R. and A. M. Schmidt, RAGE and its ligands in retinal disease. Curr. Mol. Med., 2007. 7(8): p. 758-65.
19. Glenn, J. V. and A. W. Stitt, The role of advanced glycation end products in retinal ageing and disease. Biochim. Biophys. Acta, 2009. 1790(10): p. 1109-16.
20. Hollyfield, J. G., Bonilha, V. L., Rayborn, M. E., Yang, X., Shadrach, K. G., Lu, L., Ufret, R. L., Salomon, R. G., Perez, V. L, Oxidative damage-induced inflammation initiates age-related macular degeneration. Nat. Med., 2008. 14(2): p. 194-8.
21. McKinnon, S. J., Glaucoma: ocular Alzheimer's disease? Front Biosci., 2003. 8: p. s1140-56.
22. Kooi, E. J., van Horssen, J., Witte, M. E., Amor, S., Bo, L., Dijkstra, C. D., van der Valk, P., Geurts, J. J. Abundant extracellular myelin in the meninges of patients with multiple sclerosis. Neuropathol. Appl. Neurobiol., 2009. 35(3): p. 283-95.
23. Reddy, V. P., Zhu, X., Perry, G., Smith, M. A. Oxidative stress in diabetes and Alzheimer's disease. J. Alzheimers Dis., 2009. 16(4): p. 763-74.
24. Moreira, P. I., Duarte, A. I., Santos, M. S., Rego, A. C., Oliveira, C. R. An integrative view of the role of oxidative stress, mitochondria and insulin in Alzheimer's disease. J Alzheimers Dis., 2009. 16(4): p. 741-61.
25. Doens, D. and P. L. Fernandez, Microglia receptors and their implications in the response to amyloid beta for Alzheimer's disease pathogenesis. J. Neuroinflammation, 2014. 11: p. 48.
26. Lemke, G. and C. V. Rothlin, Immunobiology of the TAM receptors. Nat. Rev. Immunol., 2008. 8(5): p. 327-36.
27. Papadopoulos, J. S. and R. Agarwala, COBALT: constraint-based alignment tool for multiple protein sequences. Bioinformatics, 2007. 23(9): p. 1073-9.
28. Goure, W. F., Krafft, G. A., Jerecic, J., Hefti, F. Targeting the proper amyloid-beta neuronal toxins: a path forward for Alzheimer's disease immunotherapeutics. Alzheimers Res. Ther., 2014. 6(4): p. 42.
29. Jarrett, J. T., E. P. Berger, and P. T. Lansbury, Jr., The carboxy terminus of the beta amyloid protein is critical for the seeding of amyloid formation: implications for the pathogenesis of Alzheimer's disease. Biochemistry, 1993. 32(18): p. 4693-7.

30. Roher, A. E., Lowenson, J. D., Clarke, S., Woods, A. S., Cotter, R. J., Gowing, E., Ball, M. J.beta-Amyloid-(1-42) is a major component of cerebrovascular amyloid deposits: implications for the pathology of Alzheimer disease. Proc.Natl. Acad. Sci. USA, 1993. 90(22): p. 10836-40.

31. Iwatsubo, T., Saido, T. C., Mann, D. M., Lee, V. M., Trojanowski, J. Q. Full-length amyloid-beta (1-42(43)) and amino-terminally modified and truncated amyloid-beta 42(43) deposit in diffuse plaques. Am. J. Pathol., 1996. 149(6): p. 1823-30.

32. Borchelt, D. R., Thinakaran, G., Eckman, C. B. et al., Familial Alzheimer's disease-linked presenilin 1 variants elevate Abetal-42/1-40 ratio in vitro and in vivo. Neuron., 1996. 17(5): p. 1005-13.

33. Eckman, C. B., Mehta, N. D., Crook, R., et al., A new pathogenic mutation in the APP gene (I716V) increases the relative proportion of A beta 42(43). Hum Mol Genet, 1997. 6(12): p. 2087-9.

34. Mayeux, R., Tang, M. X., Jacobs, D. M., et al., Plasma amyloid beta-peptide 1-42 and incipient Alzheimer's disease. Ann. Neurol., 1999. 46(3): p. 412-6.

35. Evans, C. G., S. Wisen, and J. E. Gestwicki, Heat shock proteins 70 and 90 inhibit early stages of amyloid beta-(1-42) aggregation in vitro. J. Biol. Chem., 2006. 281(44): p. 33182-91.

36. Lipovsek, D. and A. Pluckthun, In-vitro protein evolution by ribosome display and mRNA display. J. Immunol. Methods, 2004. 290(1-2): p. 51-67.

37. Shafikhani, S., Siegel, R. A., Ferrari, E., Schellenberger, V. Generation of large libraries of random mutants in *Bacillus subtilis* by PCR-based plasmid multimerization. Biotechniques, 1997. 23(2): p. 304-10.

38. Caberoy, N. B., Zhou, Y., Alvarado, G., Fan, X., Li, W. Efficient identification of phosphatidylserine-binding proteins by ORF phage display. Biochem. Biophys. Res. Commun., 2009. 386(1): p. 197-201.

39. Caberoy, N. B., Alvarado, G., Bigcas, J. L., Li, W. Galectin-3 is a new MerTK-specific eat-me signal. J. Cell. Physiol., 2012. 227(2): p. 401-7.

40. Strick, D. J., W. Feng, and D. Vollrath, Mertk drives myosin II redistribution during retinal pigment epithelial phagocytosis. Invest. Ophthalmol. Vis. Sci., 2009. 50(5): p. 2427-35.

41. Sather, S., Kenyon, K. D., Lefkowitz, J. B., et al., A soluble form of the Mer receptor tyrosine kinase inhibits macrophage clearance of apoptotic cells and platelet aggregation. Blood, 2007. 109(3): p. 1026-33.

42. Wu, Y. C., G. M. Stanfield, and H. R. Horvitz, NUC-1, a *Caenorhabditis Elegans* DNase II homolog, functions in an intermediate step of DNA degradation during apoptosis. Genes Dev., 2000. 14(5): p. 536-48.

43. Schrijvers, D. M., De Meyer, G. R., Kockx, M. M., Herman, A. G., Martinet, W. Phagocytosis of apoptotic cells by macrophages is impaired in atherosclerosis. Arterioscler Thromb Vasc. Biol., 2005. 25(6): p. 1256-61.

44. Park, D., Han, C. Z., Elliott, M. R., et al., Continued clearance of apoptotic cells critically depends on the phagocyte Ucp2 protein. Nature, 2011. 477(7363): p. 220-4.

45. Scott, C. C., R. J. Botelho, and S. Grinstein, Phagosome maturation: a few bugs in the system. J. Membr. Biol., 2003. 193(3): p. 137-52.

46. Kleiger, G., Saha, A., Lewis, S., Kuhlman, B., Deshaies, R. J. Rapid E2-E3 assembly and disassembly enable processive ubiquitylation of cullin-RING ubiquitin ligase substrates. Cell, 2009. 139(5): p. 957-68.

47. Chen, J., Huber, B. T., Grand, R. J., Li, W. Recombinant adenovirus coexpressing covalent peptide/MHC class II complex and B7-1: in vitro and in vivo activation of myelin basic protein-specific T cells. J. Immunol., 2001. 167(3): p. 1297-305.

48. Li, W., Synergistic antibody induction by antigen-CD40 ligand fusion protein as improved immunogen. Immunology, 2005. 115(2): p. 215-22.

49. Caberoy, N. B., Y. Zhou, and W. Li, Can phage display be used as a tool to functionally identify endogenous eat-me signals in phagocytosis? J. Biomol. Screen, 2009. 14(6): p. 653-61.

50. Neumann, A., Schinzel, R., Palm, D., Riederer, P., Munch, G. High molecular weight hyaluronic acid inhibits advanced glycation endproduct-induced NF-kappaB activation and cytokine expression. FEBS Lett, 1999. 453(3): p. 283-7.

51. Iida, Y., Miyata, T., Inagi, R., Sugiyama, S., Maeda, K. Beta 2-microglobulin modified with advanced glycation end products induces interleukin-6 from human macrophages: role in the pathogenesis of hemodialysis-associated amyloidosis. Biochem. Biophys. Res. Commun., 1994. 201(3): p. 1235-41.

52. Westwood, M. E. and P. J. Thornalley, Induction of synthesis and secretion of interleukin 1 beta in the human monocytic THP-1 cells by human serum albumins modified with methylglyoxal and advanced glycation endproducts. Immunol. Lett., 1996. 50(1-2): p. 17-21.

53. Giustarini, D., Rossi, R., Milzani, A., Dalle-Donne, I. Nitrite and nitrate measurement by Griess reagent in human plasma: evaluation of interferences and standardization. Methods Enzymol, 2008. 440: p. 361-80.

54. Pan, X. D., Zhu, Y. G., Lin, N., Zhang, J., et al., Microglial phagocytosis induced by fibrillar beta-amyloid is attenuated by oligomeric beta-amyloid: implications for Alzheimer's disease. Mol. Neurodegen, 2011. 6: p. 45.

55. Riss, T. L., Moravec, R. A., Niles, A. L., Benink, H. A., Worzella, T. J., Minor, L. Cell Viability Assays, in Assay Guidance Manual, G. S. Sittampalam, et al., Editors. 2004: Bethesda (Md.).

56. Cramer, P. E., Cirrito, J. R., Wesson, D. W., et al., ApoE-directed therapeutics rapidly clear beta-amyloid and reverse deficits in AD mouse models. Science, 2012. 335(6075): p. 1503-6.

57. Zhang, Q., S. X. Zeng, and H. Lu, Determination of Maximum Tolerated Dose and Toxicity of Inauhzin in Mice. Toxicol Rep, 2015. 2: p. 546-554.

58. Jankowsky, J. L., Fadale, D. J., Anderson, J., et al., Mutant presenilins specifically elevate the levels of the 42 residue beta-amyloid peptide in vivo: evidence for augmentation of a 42-specific gamma secretase. Hum. Mol. Genet., 2004. 13(2): p. 159-70.

59. Jankowsky, J. L., Slunt, H. H., Gonzales, V., Jenkins, N. A., Copeland, N. G., Borchelt, D. R. APP processing and amyloid deposition in mice haplo-insufficient for presenilin 1. Neurobiol. Aging, 2004. 25(7): p. 885-92.

60. Garcia-Alloza, M., Robbins, E. M., Zhang-Nunes, S. X., et al., Characterization of amyloid deposition in the APPswe/PS1dE9 mouse model of Alzheimer disease. Neurobiol. Dis., 2006. 24(3): p. 516-24.

61. Robinson, S., Delongeas, J. L., Donald, E., et al., A European pharmaceutical company initiative challenging the regulatory requirement for acute toxicity studies in pharmaceutical drug development. Regul. Toxicol. Pharmacol., 2008. 50(3): p. 345-52.

62. Cui, S., C. Chesson, and R. Hope, Genetic variation within and between strains of outbred Swiss mice. Lab Anim., 1993. 27(2): p. 116-23.
63. Aldinger, K. A., Sokoloff, G., Rosenberg, D. M., Palmer, A. A., Millen, K. J. Genetic variation and population substructure in outbred CD-1 mice: implications for genome-wide association studies. PLoS One, 2009. 4(3): p. e4729.
64. Rice, M. C. and S. J. O'Brien, Genetic variance of laboratory outbred Swiss mice. Nature, 1980. 283(5743): p. 157-61.
65. Chia, R., Achilli, F., Festing, M. F., Fisher, E. M. The origins and uses of mouse outbred stocks. Nat. Genet., 2005. 37(11): p. 1181-6.
66. LeBlanc, M. E., Wang, W., Caberoy, N. B., et al., Hepatoma-derived growth factor-related protein-3 is a novel angiogenic factor. PLoS One, 2015. 10(5): p. e0127904.
67. Kinney, J. W., Sanchez-Alavez, M., Barr, A. M., et al., Impairment of memory consolidation by galanin correlates with in vivo inhibition of both LTP and CREB phosphorylation. Neurobiol. Learn Mem., 2009. 92(3): p. 429-38.
68. Sabbagh, J. J., Heaney, C. F., Bolton, M. M., et al., Administration of donepezil does not rescue galanin-induced spatial learning deficits. Int. J. Neurosci., 2012. 122(12): p. 742-7.
69. Murtishaw, A. S., Heaney, C. F., Bolton, M. M., et al., Effect of acute lipopolysaccharide-induced inflammation in intracerebroventricular-streptozotocin injected rats. Neuropharmacology, 2015.
70. Radde, R., Bolmont, T., Kaeser, S. A., et al., Abeta42-driven cerebral amyloidosis in transgenic mice reveals early and robust pathology. EMBO Rep., 2006. 7(9): p. 940-6.
71. Bolton, M. M., Heaney, C. F., Murtishaw, A. S., Sabbagh, J. J., Magcalas, C. M., Kinney, J. W. Postnatal alterations in GABAB receptor tone produce sensorimotor gating deficits and protein level differences in adulthood. Int. J. Dev. Neurosci., 2015. 41: p. 17-27.
72. Landers, M. R., J. W. Kinney, and F. van Breukelen, Forced exercise before or after induction of 6-OHDA-mediated nigrostriatal insult does not mitigate behavioral asymmetry in a hemiparkinsonian rat model. Brain Res., 2014. 1543: p. 263-70.
73. Kinney, J. W., Sanchez-Alavez, M., Barr, A. M., et al., Impairment of memory consolidation by galanin correlates with in vivo inhibition of both LTP and CREB phosphorylation. Neurobiol. Learn Mem., 2009. 92(3): p. 429-38.
74. Tampellini, D., Magrane, J., Takahashi, R. H., et al., Internalized antibodies to the Abeta domain of APP reduce neuronal Abeta and protect against synaptic alterations. J. Biol. Chem., 2007. 282(26): p. 18895-906.
75. Tsai, Y., Lu, B., Ljubimov, A. V., et al., Ocular changes in TgF344-AD rat model of Alzheimer's disease. Invest. Ophthalmol. Vis. Sci., 2014. 55(1): p. 523-34.
76. Jensen, C. J., A. Massie, and J. De Keyser, Immune players in the CNS: the astrocyte. J. Neuroimmune Pharmacol., 2013. 8(4): p. 824-39.
77. Graeber, M. B., W. J. Streit, and G. W. Kreutzberg, The third glial cell type, the microglia: cellular markers of activation in situ. Acta Histochem. Suppl., 1990. 38: p. 157-60.
78. Slepko, N. and G. Levi, Progressive activation of adult microglial cells in vitro. Glia, 1996. 16(3): p. 241-46.
79. Kingham, P. J., M. L. Cuzner, and J. M. Pocock, Apoptotic pathways mobilized in microglia and neurones as a consequence of chromogranin A-induced microglial activation. J. Neurochem., 1999. 73(2): p. 538-47.
80. Fang, X., Jiang, Y., Ji, H., et al., The Synergistic Beneficial Effects of Ginkgo Flavonoid and *Coriolus versicolor* Polysaccharide for Memory Improvements in a Mouse Model of Dementia. Evid Based Complement Alternat. Med., 2015. 2015: p. 128394.
81. Guo, H. B., Cheng, Y. F., Wu, J. G., et al., Donepezil improves learning and memory deficits in APP/PS1 mice by inhibition of microglial activation. Neuroscience, 2015. 290: p. 530-42.

I claim:

1. A composition comprising one or more amyloid beta binding proteins conjugated to one or more MerTK ligands, wherein the one or more amyloid beta binding proteins comprises the amino acid sequence of LDLSNEGLSGSLNGTLDKTLKQPL (SEQ ID NO:1), LDLSNRGSSGSLNGTSDKTLKQPL (SEQ ID NO:28), LDLSNRGSSGSSNGTLDKTLKQPL (SEQ ID NO:29), LDLSNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), or LDLSNEGLSGSSSGSSDKTLKQPL (SEQ ID NO:33), wherein the one or more MerTK ligands comprises the sequence K/R(X)$_{1-2}$KKK.

2. The composition of claim 1, wherein the MerTK ligand is Tubby, Tulp1, or a fragment thereof.

3. The composition of claim 2, wherein the MerTK ligand comprises the amino acid sequence KRRKKK (SEQ ID NO:36) or KQKKK (SEQ ID NO:37).

4. The composition of claim 2, wherein the MerTK ligand consists of the amino acid sequence KRRKKK (SEQ ID NO:36) or KQKKK (SEQ ID NO:37).

5. The composition of claim 1, wherein the amyloid beta binding protein is mutated.

6. The composition of claim 5, wherein the mutated amyloid beta binding protein consists of the amino acid sequence LDLSNRGSSGSLNGTSDKTLKQPL (SEQ ID NO:28), LDLSNRGSSGSSNGTLDKTLKQPL (SEQ ID NO:29), LDLSNEGSSGSSSGTLDKTLKQPL (SEQ ID NO:30), LDLSNEGRSGSSNGTSDKTLKQPL (SEQ ID NO:31), LDLSNESSSGSLSGTSDKTLKQPL (SEQ ID NO:32), or LDLSNEGLSGSSSGSSDKTLKQPL (SEQ ID NO:33).

7. The composition of claim 1 wherein the amyloid beta binding protein is conjugated to a MerTK ligand with a linker.

8. The composition of claim 7, wherein the linker is the amino acid sequence GSG.

9. The composition of claim 1, wherein the composition comprises two or more amyloid beta binding proteins.

10. The composition of claim 1, wherein the composition comprises two or more MerTK ligands.

11. The composition of claim 1, wherein the composition comprises the amino acid sequence KRRKKKGSGKRRKKKGSGKRRKKKGSGLDL-SNEGLSGSLNGTLDKTLKQPL GSGLDL-SNEGLSGSLNGTLDKTLKQPLGSGLDL-SNEGLSGSLNGTLDKTLKQP L (SEQ ID NO:34).

12. The composition of claim 1, wherein the composition comprises the amino acid sequence KRRKKKGSGKRRKKKGSGKRRKKKGSGLDL-SNEGLSGSSSGSSDKTLKQPL GSGLDL-SNEGLSGSSSGSSDKTLKQPLGSGLDL-SNEGLSGSSSGSSDKTLKQPL (SEQ ID NO:35).

13. The composition of claim 1, further comprising a pharmaceutically acceptable carrier.

14. A method of clearing amyloid beta aggregates from a subject comprising administering a therapeutically effective amount of the composition of claim 1.

15. A method of treating Alzheimer's Disease comprising administering to a subject in need thereof a therapeutically effective amount of the composition of claim 1.

* * * * *

```
SEQUENCE LISTING

<160> NUMBER OF SEQ ID NOS: 37

<210> SEQ ID NO 1
<211> LENGTH: 24
<212> TYPE: PRT
<213> ORGANISM: Artificial Sequence
<220> FEATURE:
<223> OTHER INFORMATION: synthetic construct; amyloid beta binding
      protein

<400> SEQUENCE: 1

Leu Asp Leu Ser Asn Glu Gly Leu Ser Gly Ser Leu Asn Gly Thr Leu
1               5                   10                  15

Asp Lys Thr Leu Lys Gln Pro Leu
            20

<210> SEQ ID NO 2
<211> LENGTH: 29
<212> TYPE: PRT
<213> ORGANISM: Artificial Sequence
<220> FEATURE:
<223> OTHER INFORMATION: synthetic construct; amyloid beta binding
      protein
```

```
<400> SEQUENCE: 2

Pro Ala Glu Cys Asp Trp Gly Lys Gly Arg Trp Arg Leu Trp Pro
1               5                   10                  15

Gly Ala Ser Gly Lys Thr Glu Ala Cys Gly Pro Pro Tyr
            20                  25

<210> SEQ ID NO 3
<211> LENGTH: 38
<212> TYPE: PRT
<213> ORGANISM: Artificial Sequence
<220> FEATURE:
<223> OTHER INFORMATION: synthetic construct; amyloid beta binding
      protein

<400> SEQUENCE: 3

Lys Ile Gly Lys Val Val Phe Pro Asp Cys Ile Ala Ser Asp Pro Phe
1               5                   10                  15

Lys Leu Val Val Asp Asp Thr Leu Ser Tyr Val Ala Glu Ile Arg Gly
            20                  25                  30

Ile Leu Pro Arg Ser Asp
            35

<210> SEQ ID NO 4
<211> LENGTH: 27
<212> TYPE: PRT
<213> ORGANISM: Artificial Sequence
<220> FEATURE:
<223> OTHER INFORMATION: synthetic construct; amyloid beta binding
      protein

<400> SEQUENCE: 4

Met Ala Val Trp Ala Lys Val Arg Ser Ala Leu Ala Val Glu Ala Val
1               5                   10                  15

Val Gly Asp Lys Ala Asp Lys Val Ala Leu Asp
            20                  25

<210> SEQ ID NO 5
<211> LENGTH: 32
<212> TYPE: PRT
<213> ORGANISM: Artificial Sequence
<220> FEATURE:
<223> OTHER INFORMATION: synthetic construct; amyloid beta binding
      protein

<400> SEQUENCE: 5

Leu Gly Val Gln Tyr Ala Lys Gly Ile Ser Gln Gly Glu Leu Val Val
1               5                   10                  15

Ser Ser Ala Pro Val Gln Asp Phe Ala Pro Ile Ala Lys Leu Leu Ile
            20                  25                  30

<210> SEQ ID NO 6
<211> LENGTH: 45
<212> TYPE: PRT
<213> ORGANISM: Artificial Sequence
<220> FEATURE:
<223> OTHER INFORMATION: synthetic construct; amyloid beta binding
      protein

<400> SEQUENCE: 6

Arg Leu Gly Arg Gly Leu Leu Ala Lys Leu Asp Leu Lys Trp Leu Lys
1               5                   10                  15

Leu Glu Arg Asp Gly Thr Ala Ala Glu Lys Leu His Glu Asp Leu Lys
            20                  25                  30
```

```
Lys Ile Leu Arg Glu Glu Leu Arg Arg Glu Leu Leu Leu
            35                  40                  45

<210> SEQ ID NO 7
<211> LENGTH: 36
<212> TYPE: PRT
<213> ORGANISM: Artificial Sequence
<220> FEATURE:
<223> OTHER INFORMATION: synthetic construct; amyloid beta binding
      protein

<400> SEQUENCE: 7

Met Lys Ile Gly Ile Gly Lys Gly Glu Glu Ile Val Pro Glu Glu Glu
1               5                   10                  15

Lys Pro Ser Ala Lys Lys Leu Lys Leu Lys Lys Ala Leu Gly Leu Val
            20                  25                  30

Glu Gly Leu Phe
        35

<210> SEQ ID NO 8
<211> LENGTH: 46
<212> TYPE: PRT
<213> ORGANISM: Artificial Sequence
<220> FEATURE:
<223> OTHER INFORMATION: synthetic construct; amyloid beta binding
      protein

<400> SEQUENCE: 8

Pro Ser Phe Asp Gln Lys Leu Glu Ser Arg Leu Gln Ala Glu Leu Ser
1               5                   10                  15

Pro Gly Leu Gly His Ala Ile Glu Ala Ile Phe Leu Phe Ala Asp Asp
            20                  25                  30

Ala Lys Glu Gly Leu Ala Glu Asp Leu Leu Gly Glu Lys Ala
            35                  40                  45

<210> SEQ ID NO 9
<211> LENGTH: 99
<212> TYPE: PRT
<213> ORGANISM: Artificial Sequence
<220> FEATURE:
<223> OTHER INFORMATION: synthetic construct; amyloid beta binding
      protein

<400> SEQUENCE: 9

Lys Lys Gly Lys Leu Gly Glu Pro Phe Gln Leu Ile Gly Leu Leu Ile
1               5                   10                  15

Leu Ala Arg Phe Ile Ile Gln Lys Lys Leu Asp Ala Leu Lys Glu
            20                  25                  30

Val Leu Glu Leu Ala Thr Lys Arg Leu Leu Lys Phe Asp Leu Lys Leu
            35                  40                  45

Glu Glu Arg Asp Leu Lys Lys Gln Glu Leu Leu Glu Leu Gln Glu Leu
        50                  55                  60

Arg Lys Asp Val Leu Leu Ala Asp Leu Ala Asn Gln Asp Asp Glu
65                  70                  75                  80

Ala Leu Leu Arg Ala Asp Lys Glu Ala Asp Ile Leu Glu Leu Glu Asn
                85                  90                  95

Ala Asp Lys

<210> SEQ ID NO 10
<211> LENGTH: 104
<212> TYPE: PRT
<213> ORGANISM: Artificial Sequence
```

```
<220> FEATURE:
<223> OTHER INFORMATION: synthetic construct; amyloid beta binding
      protein

<400> SEQUENCE: 10

Val Gly Gly Asp Val Val Glu Gly Thr Ser His Ser Gly Leu Ile Thr
1               5                   10                  15

Asp Leu Gly Val Val Asn Gly Gly Arg Ala Leu Leu Ser Gly Pro Glu
                20                  25                  30

Pro Leu Asn Gly Thr Asp Leu Pro Ala Leu Leu Ala Ala Gly Leu Leu
            35                  40                  45

Phe Glu Leu Ser Glu Ala Pro Glu Ile Leu Val Gly Glu Tyr Ser Thr
50                  55                  60

Val Ser Leu Val Ala Val Gly Ala Glu Val Pro Leu Glu Asp Tyr Leu
65                  70                  75                  80

Asp Glu Gly Asp Lys His Gly Glu Ala Leu Ser Asp Tyr Trp Asp Gln
                85                  90                  95

Leu Leu Glu Leu Ser Ile Leu Leu
            100

<210> SEQ ID NO 11
<211> LENGTH: 78
<212> TYPE: PRT
<213> ORGANISM: Artificial Sequence
<220> FEATURE:
<223> OTHER INFORMATION: synthetic construct; amyloid beta binding
      protein

<400> SEQUENCE: 11

Val Gly Gly Glu Gly Ile Ser Gly Thr Ile Phe Asn Ile Tyr Gly Gly
1               5                   10                  15

Phe Ile Pro Gly Lys Leu Arg Arg Leu Pro Asp Ala Glu Ile Trp Gly
                20                  25                  30

Gly Leu Ser Leu Gly Gly Asp Gln Arg Phe Gly Asp Gly Thr Ala Val
            35                  40                  45

Ile Gly Leu Ser Val Ser Leu Lys Ser Gly Gly Ala Glu Leu Val Ala
50                  55                  60

Glu Leu Tyr Val Asp Pro Gly Val Ser Ser Gln Pro Glu Glu
65                  70                  75

<210> SEQ ID NO 12
<211> LENGTH: 58
<212> TYPE: PRT
<213> ORGANISM: Artificial Sequence
<220> FEATURE:
<223> OTHER INFORMATION: synthetic construct; amyloid beta binding
      protein

<400> SEQUENCE: 12

Met Leu Val Asp Gly Gly Lys Leu Gly Val Leu Ala Lys Gln Leu Lys
1               5                   10                  15

Glu Tyr Leu Ala Phe Asp Arg Asp Leu Asp Asp Leu Val Phe Lys Ala
                20                  25                  30

Lys Ile Gln Val Asn Asp Gly Ala Leu Gly Val Ile Ser Asn Leu Leu
            35                  40                  45

Phe Gly Gly Gly Ile Val Gly Gln Ile Leu
50                  55

<210> SEQ ID NO 13
<211> LENGTH: 93
```

```
<212> TYPE: PRT
<213> ORGANISM: Artificial Sequence
<220> FEATURE:
<223> OTHER INFORMATION: synthetic construct; amyloid beta binding
      protein

<400> SEQUENCE: 13

Ser Leu Ala Leu Leu Val Glu Thr Asn Glu Leu Asp Asp Ala Ala Val
1               5                   10                  15

Glu Leu Ile Arg Lys Leu Gly Gly Thr Asp Ala Glu Leu Lys Ile Ile
            20                  25                  30

Leu Ala Gly Asp Gly Ile Asp Gly Ile Ser Trp Pro Ala Leu Gly Asn
        35                  40                  45

Glu Ala Gly Asp Leu Val Gly Ser Ser Gly Ile Ala Gly Gly Lys Pro
    50                  55                  60

Val Leu Pro Asp Glu Ala Phe Val Arg Leu Ser Val Asn Ala Ser Gly
65                  70                  75                  80

Gly Phe Val Asp Gly Ile Lys Glu Gly Pro Val Val Leu
                85                  90

<210> SEQ ID NO 14
<211> LENGTH: 80
<212> TYPE: PRT
<213> ORGANISM: Artificial Sequence
<220> FEATURE:
<223> OTHER INFORMATION: synthetic construct; amyloid beta binding
      protein

<400> SEQUENCE: 14

Gly Asp Gly Pro Ser Asp Leu Glu Val Val Arg Leu Ile Thr Pro Gly
1               5                   10                  15

Gln Ala Leu Ala Pro Phe Thr Asn Ala Gly Gln Ala Ala Ala Val Pro
            20                  25                  30

Arg Ser Glu Gly Glu Ser Met Ile Ala Val Ser His Asn Met Leu Pro
        35                  40                  45

Gln Val Ser Ser Glu Val Val Glu Gly Tyr Ala Thr Lys Asn Glu Thr
    50                  55                  60

Glu Asn Glu Thr Leu Cys Met Lys Ile Gly Pro Pro Ile Val Gly Glu
65                  70                  75                  80

<210> SEQ ID NO 15
<211> LENGTH: 62
<212> TYPE: PRT
<213> ORGANISM: Artificial Sequence
<220> FEATURE:
<223> OTHER INFORMATION: synthetic construct; amyloid beta binding
      protein

<400> SEQUENCE: 15

Arg Pro Asp Glu Ile Val Gly Val Trp Ser Ser Tyr Leu Gly Leu Gly
1               5                   10                  15

Phe Val Leu Ser Lys Ala Val Ile Leu Glu Leu Arg Asn Trp Phe
            20                  25                  30

Gly Lys Gln Ser Gly Ala Tyr Leu Asp Tyr Leu His Gly Ser Val Ala
        35                  40                  45

Leu Leu Gly Asp Lys Asn Met Gly Arg Lys Leu Ser Gln Ser
    50                  55                  60

<210> SEQ ID NO 16
<211> LENGTH: 73
<212> TYPE: PRT
```

<213> ORGANISM: Artificial Sequence
<220> FEATURE:
<223> OTHER INFORMATION: synthetic construct; amyloid beta binding
      protein

<400> SEQUENCE: 16

His Leu Leu Ile Asp Lys Gly Val Ala Gly Gly Pro Gly Phe Asp Thr
1               5                   10                  15

Val Ala Ser Leu Ala Glu Thr Glu Lys Ala Arg Gly Pro Glu Val Ser
            20                  25                  30

Thr Leu Ala Lys Glu Asp Phe Ala Lys Thr Ile Gly Glu Leu Gly Ala
        35                  40                  45

Gly Pro Lys Thr Ser Lys Ala Val Val Gly Glu Gly Lys Glu Ile
    50                  55                  60

Pro Leu Gly Pro Gly Lys Ser Tyr Pro
65                  70

<210> SEQ ID NO 17
<211> LENGTH: 65
<212> TYPE: PRT
<213> ORGANISM: Artificial Sequence
<220> FEATURE:
<223> OTHER INFORMATION: synthetic construct; amyloid beta binding
      protein

<400> SEQUENCE: 17

Ser Ser Ser Leu Phe Gln Leu Pro Thr Asp Gly Lys Leu Val Gln Ala
1               5                   10                  15

Leu Ile Thr Asn Leu Tyr Gly Ser Ala Leu Asp Gly Tyr Glu Val Arg
            20                  25                  30

Asp Leu Glu Leu Ile Met Glu Lys Arg Leu Val Ile Ser Ile Asn Gly
        35                  40                  45

Arg Ile Pro Ala Glu Phe Asn Gln Asp Leu Gly Leu Arg Leu Leu Leu
    50                  55                  60

Thr
65

<210> SEQ ID NO 18
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 18

Pro Ala Glu Cys Asp Trp Gly Lys Gly Gly Arg Trp Arg Leu Trp Pro
1               5                   10                  15

Ser Ala Ser Gly Lys Thr Glu Ala Cys Gly Pro Pro Tyr
            20                  25

<210> SEQ ID NO 19
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 19

Pro Ala Glu Cys Asp Trp Gly Lys Gly Gly Arg Trp Arg Asp Trp Pro
1               5                   10                  15

Gly Ala Ser Gly Lys Thr Glu Ala Cys Gly Pro Pro Tyr
            20                  25

<210> SEQ ID NO 20
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 20

Pro Ala Glu Cys Asp Trp Gly Lys Gly Gly Arg Trp Arg Leu Trp Pro
1               5                   10                  15

Gly Ser Ser Gly Lys Thr Glu Ala Cys Gly Pro Pro Tyr
            20                  25

<210> SEQ ID NO 21
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 21

Pro Ala Glu Cys Asp Trp Lys Lys Gly Gly Arg Trp Arg Leu Trp Pro
1               5                   10                  15

Gly Ala Ser Gly Lys Thr Glu Ala Cys Gly Pro Pro Tyr
            20                  25

<210> SEQ ID NO 22
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 22

Pro Ala Glu Cys Asp Trp Gly Lys Gly Gly Leu Trp Arg Leu Trp Pro
1               5                   10                  15

Gly Ala Ser Gly Lys Thr Glu Ala Cys Gly Pro Pro Tyr
            20                  25

<210> SEQ ID NO 23
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 23

Pro Ala Glu Cys Asp Trp Gly Lys Gly Arg Arg Trp Arg Ser Trp Pro
1               5                   10                  15

Gly Ala Ser Gly Lys Thr Glu Ala Cys Gly Pro Pro Tyr
            20                  25

<210> SEQ ID NO 24
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 24

Pro Ala Glu Cys Asp Trp Gly Lys Gly Gly Arg Trp Arg Leu Trp Pro
1               5                   10                  15

Gly Ala Ser Gly Lys Thr Asp Ala Cys Gly Pro Pro Tyr
            20                  25

<210> SEQ ID NO 25
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 25

Pro Ala Glu Cys Asp Trp Gly Lys Gly Gly Arg Trp Arg Leu Arg Pro
1               5                   10                  15

Gly Ala Ser Gly Lys Thr Glu Ala Cys Gly Pro Pro Tyr
            20                  25

<210> SEQ ID NO 26
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 26

Pro Ala Glu Cys Asp Trp Gly Lys Gly Gly Arg Trp Arg Leu Trp Pro
1               5                   10                  15

Gly Ala Ser Leu Lys Thr Glu Ala Cys Gly Pro Pro Tyr
            20                  25

<210> SEQ ID NO 27
<211> LENGTH: 29
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 27

Pro Ala Glu Cys Asp Trp Gly Lys Lys Gly Arg Trp Arg Leu Trp Pro
1               5                   10                  15

Gly Ala Ser Gly Lys Thr Glu Ala Cys Gly Pro Pro Tyr
            20                  25

<210> SEQ ID NO 28
<211> LENGTH: 24
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 28

Leu Asp Leu Ser Asn Arg Gly Ser Gly Ser Leu Asn Gly Thr Ser
1               5                   10                  15

Asp Lys Thr Leu Lys Gln Pro Leu
            20

<210> SEQ ID NO 29

```
<211> LENGTH: 24
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 29

Leu Asp Leu Ser Asn Arg Gly Ser Ser Gly Ser Ser Asn Gly Thr Leu
1               5                   10                  15

Asp Lys Thr Leu Lys Gln Pro Leu
            20

<210> SEQ ID NO 30
<211> LENGTH: 24
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 30

Leu Asp Leu Ser Asn Glu Gly Ser Ser Gly Ser Ser Ser Gly Thr Leu
1               5                   10                  15

Asp Lys Thr Leu Lys Gln Pro Leu
            20

<210> SEQ ID NO 31
<211> LENGTH: 24
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 31

Leu Asp Leu Ser Asn Glu Gly Arg Ser Gly Ser Ser Asn Gly Thr Ser
1               5                   10                  15

Asp Lys Thr Leu Lys Gln Pro Leu
            20

<210> SEQ ID NO 32
<211> LENGTH: 24
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 32

Leu Asp Leu Ser Asn Glu Ser Ser Ser Gly Ser Leu Ser Gly Thr Ser
1               5                   10                  15

Asp Lys Thr Leu Lys Gln Pro Leu
            20

<210> SEQ ID NO 33
<211> LENGTH: 24
<212> TYPE: PRT
<213> ORGANISM: Artificial Sequence
<220> FEATURE:
<223> OTHER INFORMATION: synthetic construct; mutant amyloid beta
      binding protein

<400> SEQUENCE: 33

Leu Asp Leu Ser Asn Glu Gly Leu Ser Gly Ser Ser Gly Ser Ser
1               5                   10                  15
```

Asp Lys Thr Leu Lys Gln Pro Leu
            20

<210> SEQ ID NO 34
<211> LENGTH: 105
<212> TYPE: PRT
<213> ORGANISM: Artificial Sequence
<220> FEATURE:
<223> OTHER INFORMATION: synthetic construct; amyloid beta binding
      protein and MerTK ligand conjugate

<400> SEQUENCE: 34

Lys Arg Arg Lys Lys Lys Gly Ser Gly Lys Arg Arg Lys Lys Lys Gly
1               5                   10                  15

Ser Gly Lys Arg Arg Lys Lys Lys Gly Ser Gly Leu Asp Leu Ser Asn
            20                  25                  30

Glu Gly Leu Ser Gly Ser Leu Asn Gly Thr Leu Asp Lys Thr Leu Lys
        35                  40                  45

Gln Pro Leu Gly Ser Gly Leu Asp Leu Ser Asn Glu Gly Leu Ser Gly
    50                  55                  60

Ser Leu Asn Gly Thr Leu Asp Lys Thr Leu Lys Gln Pro Leu Gly Ser
65                  70                  75                  80

Gly Leu Asp Leu Ser Asn Glu Gly Leu Ser Gly Ser Leu Asn Gly Thr
                85                  90                  95

Leu Asp Lys Thr Leu Lys Gln Pro Leu
            100                 105

<210> SEQ ID NO 35
<211> LENGTH: 105
<212> TYPE: PRT
<213> ORGANISM: Artificial Sequence
<220> FEATURE:
<223> OTHER INFORMATION: synthetic construct; amyloid beta binding
      protein and MerTK ligand conjugate

<400> SEQUENCE: 35

Lys Arg Arg Lys Lys Lys Gly Ser Gly Lys Arg Arg Lys Lys Lys Gly
1               5                   10                  15

Ser Gly Lys Arg Arg Lys Lys Lys Gly Ser Gly Leu Asp Leu Ser Asn
            20                  25                  30

Glu Gly Leu Ser Gly Ser Ser Gly Ser Ser Asp Lys Thr Leu Lys
        35                  40                  45

Gln Pro Leu Gly Ser Gly Leu Asp Leu Ser Asn Glu Gly Leu Ser Gly
    50                  55                  60

Ser Ser Ser Gly Ser Ser Asp Lys Thr Leu Lys Gln Pro Leu Gly Ser
65                  70                  75                  80

Gly Leu Asp Leu Ser Asn Glu Gly Leu Ser Gly Ser Ser Ser Gly Ser
                85                  90                  95

Ser Asp Lys Thr Leu Lys Gln Pro Leu
            100                 105

<210> SEQ ID NO 36
<211> LENGTH: 6
<212> TYPE: PRT
<213> ORGANISM: Artificial Sequence
<220> FEATURE:
<223> OTHER INFORMATION: synthetic construct; MerTK ligand

<400> SEQUENCE: 36

Lys Arg Arg Lys Lys Lys

```
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic construct; MerTK ligand

<400> SEQUENCE: 37

Lys Gln Lys Lys Lys
1               5
```